United States Patent [19]
Nakamura et al.

[11] Patent Number: 5,262,309
[45] Date of Patent: Nov. 16, 1993

[54] TERMINAL MODIFICATIONS OF TUMOR NECROSIS FACTOR

[75] Inventors: Satoshi Nakamura; Masami Fukuoka; Tsukio Masegi; Kazuo Kitai, all of Hino; Arata Kato, Koshigaya; Yataro Ichikawa, Tokorozawa, all of Japan

[73] Assignee: Teijin Limited, Osaka, Japan

[21] Appl. No.: 668,517

[22] PCT Filed: Sep. 22, 1989

[86] PCT No.: PCT/JP89/00966
§ 371 Date: Mar. 22, 1991
§ 102(e) Date: Mar. 22, 1991

[87] PCT Pub. No.: WO90/03395
PCT Pub. Date: Apr. 5, 1990

[30] Foreign Application Priority Data

Sep. 22, 1988 [JP] Japan .................. 63-236497
Nov. 25, 1988 [JP] Japan .................. 63-296305
Nov. 25, 1988 [JP] Japan .................. 63-296307
Dec. 16, 1988 [JP] Japan .................. 63-316453

[51] Int. Cl.$^5$ .............. C12P 21/06; C07K 13/00; C12N 15/00
[52] U.S. Cl. .................. 435/69.5; 530/351; 435/172.3
[58] Field of Search .............. 435/69.1; 530/351, 69.5, 530/172.3

[56] References Cited

U.S. PATENT DOCUMENTS 4,736,020 4/1988 Hillen et al. .

OTHER PUBLICATIONS

Stryer 1981, *Biochemistry*, W. H. Freeman & Co., San Francisco, Chap. 2, pp. 18-20.
Creasey et al. 1987 Cancer Res. 47:145-149.
Kamijo et al. 1989 Biochem. Biophys. Res. Commun. 160(2):80-827.
Gase et al. 1990 Immunology 71:368-371.
Nakamura et al. 1991 Int. J. Cancer 48:744-748.
Somura et al., "Cancer and Chemotherapy", 12 160-162 (1985).

Primary Examiner—Robert J. Hill, Jr.
Assistant Examiner—K. Cochrane Carlson
Attorney, Agent, or Firm—Wenderoth, Lind & Ponack

[57] ABSTRACT

This invention relates to a novel physiologically active polypeptide containing modified amino acids on both terminals at the amino-terminus and the carboxy-terminus in the amino acid sequence of the human tumor neclosis factor (human TNF), a recombinant plasmid containing a DNA region encoding the polypeptide, a recombinant microorganism cell transformed with the recombinant plasmid, a method of producing the polypeptide by cultivating the microorganism cell, a pharmaceutical composition containing the polypeptide and a method of purifying and recovering the polypeptide. The polypeptide in this invention has excellent antitumor activity compared to the human TNF and can be utilized as an active ingredient of a pharmaceutical composition having antitumor activity.

7 Claims, 31 Drawing Sheets

Fig. 1

```
Cla I
 ↓
TCG.ATA.ATG.GTC.AGG.TCA.TCT.TCA.CGA.ACC.CCG.AGT.GAC.AAG.CCT.GTA.GCC.CAT.GTT.GTA
    MET-Val-Arg-Ser-Ser-Ser-Arg-Thr-Pro-Ser-Asp-Lys-Pro-Val-Ala-His-Val-Val
    0  1                                          10

GCA.AAC.CCT.CAA.GCT.GAG.GGG.CAG.CTC.CAG.TGG.CTG.AAC.CGG.GCC.CGG.AAT.GCC.CTG.CTG
Ala-Asn-Pro-Gln-Ala-Glu-Gly-Gln-Leu-Gln-Trp-Leu-Asn-Arg-Ala-Arg-Asn-Ala-Leu-Leu
              20                                30

GCC.AAT.GGC.GTG.GAG.CTG.AGA.GAT.AAC.CAG.CTG.GTA.CCA.TCA.GAG.GGC.TTG.TAC.CTC.TCC
Ala-Asn-Gly-Val-Glu-Leu-Arg-Asp-Asn-Gln-Leu-Val-Pro-Ser-Glu-Gly-Leu-Tyr-Leu
        40                                50

ATT.TAC.TCC.CAG.GTC.CTC.TTC.AAG.GGC.CAA.GGC.TGC.CCG.TCG.ACC.CAT.GTG.CTC.CTC.ACC
Ile-Tyr-Ser-Gln-Val-Leu-Phe-Lys-Gly-Gln-Gly-Cys-Pro-Ser-Thr-His-Val-Leu-Leu-Thr
            60                                70

CAC.ACC.ATC.AGC.CGC.ATC.GCC.GTC.TCC.TAC.CAG.ACC.AAG.GTC.AAC.CTC.CTC.TCT.GCG.ATC
His-Thr-Ile-Ser-Arg-Ile-Ala-Val-Ser-Tyr-Gln-Thr-Lys-Val-Asn-Leu-Leu-Ser-Ala-Ile
                80                                90

AAG.AGC.CCC.TGC.CAG.AGG.GAG.ACC.CCA.GAG.GGG.GCT.GAG.GCC.AAG.CCA.TGG.TAT.GAG.CCC
Lys-Ser-Pro-Cys-Gln-Arg-Glu-Thr-Pro-Glu-Gly-Ala-Glu-Ala-Lys-Pro-Trp-Tyr-Glu-Pro
                    100                               110

ATC.TAT.CTG.GGA.GGG.GTC.TTC.CAG.CTG.GAG.AAG.GGT.GAC.CGA.CTC.AGC.GCT.GAA.ATC.AAT
Ile-Tyr-Leu-Gly-Gly-Val-Phe-Gln-Leu-Glu-Lys-Gly-Asp-Arg-Leu-Ser-Ala-Glu-Ile-Asn
                        120                               130

CGG.CCC.GAC.TAT.CTC.GAC.TTT.GCC.GAG.TCT.GGG.CAG.GTC.TAC.TTT.GGG.ATT.ATT.GCC.CTG
Arg-Pro-Asp-Tyr-Leu-Asp-Phe-Ala-Glu-Ser-Gly-Gln-Val-Tyr-Phe-Gly-Ile-Ile-Ala-Leu
                            140                               150
     Hind III
        ↓
TGA.TAA.GCT
***-***
```

Fig. 2

```
          |---------TNF-1---------|
CGATAATGGTCAGGTCATCTTCACGAAGTGACAGTGACAAGCCTGTAGCCCATGTTGTAG
TATTACCAGTCCAGTAGAAGTGCTTCACTGTTCGGACATCGGGTACAACATC
                     |---------TNF-2---------|
                                      |---------TNF-3---------|
CAAACCCTCAAGCTGAGGGGCAGCTCCAGTGGCTGAACCGGCCGGCCAATGCCCTGCTGG
GTTTGGGAGTTCGACTCCCCGTCGAGGTCACCGACTTGGCCGGCCGGTTACGGGACGACC
                        |---------TNF-4---------|
                                     |---------TNF-6---------|
CCAATGGGCGTGGAGCTGAGAGATAACCAGCTGGTTGGTACCATCAGAGGGCTTGTACCTCA
GGTTACCCGCACCTCGACTCTCTATTGGTCGACCAACCATGGTAGTCTCCCGAACATGGAGT
                        |---------TNF-5---------|
TTTACTCCCAGGTCCTCTCTTCAAGGGCCAAGGCTGCCCGTCGACCCATGTGCTCCTCACCC
AAATGAGGGTCCAGGAGAAGTTCCCGGTTCCGACGGGCAGCTGGGTACACGAGGAGTGGGG
           |---------TNF-7---------|
                        |---------TNF-8---------|
                                   |---------TNF-12---------|
ACACCATCAGCGGCATCGCGGCTGTCTCCTACCAGAGACCAAGGTCAACCTCCTCTGCGATCA
TGTGGTAGTCGGGCGTAGCGCCGACAGAGGATGGTCTGGTTCCAGTTGGAGAGACGCTAGT
            |---------TNF-10---------|
                        |---------TNF-9---------|
                                   |---------TNF-13---------|
AGAGCCCCTGCCAGGAGGAGACCCCAGAGGGGTCTGAGGCCAAGCCATGGTATGAGCCCA
TCTCGGGGACGGTCCTCCTCTGGGGTCTCCCCAGACTCCGGTTCGGTACCATACTCGGGT
            |---------TNF-11---------|
                                   |---------TNF-14---------|
                                              |---------TNF-15---------|
TCTATCTGGGAGGGGTCTTCCAGCTGGAAGGGTGACCGACTCAGCGGCTGAAATCAATC
AGATAGACCCTCCCCAGAAGGTCGACCTTCCCACTGGCTGAGTCGCCGACTTTAGTTAG
            |---------TNF-16---------|
                        |---------TNF-17---------|
GGCCCGACTATCTCGACTTTGCCGAGTCTGGGCAGGTCTACTTTGGGATTATTGCCCTGT
CCGGGCTGATAGAGCTGAAACGGCTCAGACCCGTCCAGATGAAACCCTAATAACGGGACA
  |------|
   GATA
   CTATTCGA
  |------|
```

Fig. 7-A
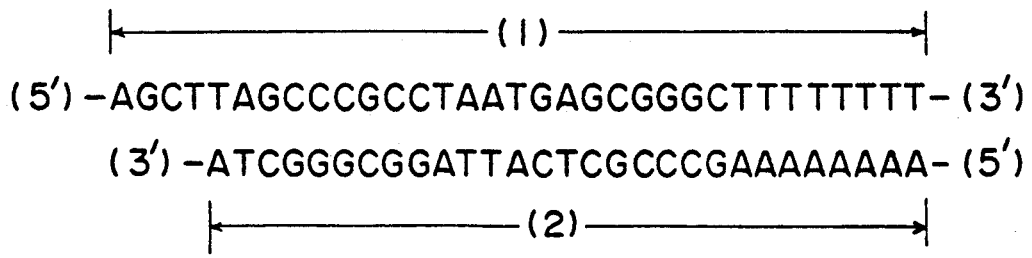
Fig. 7-B
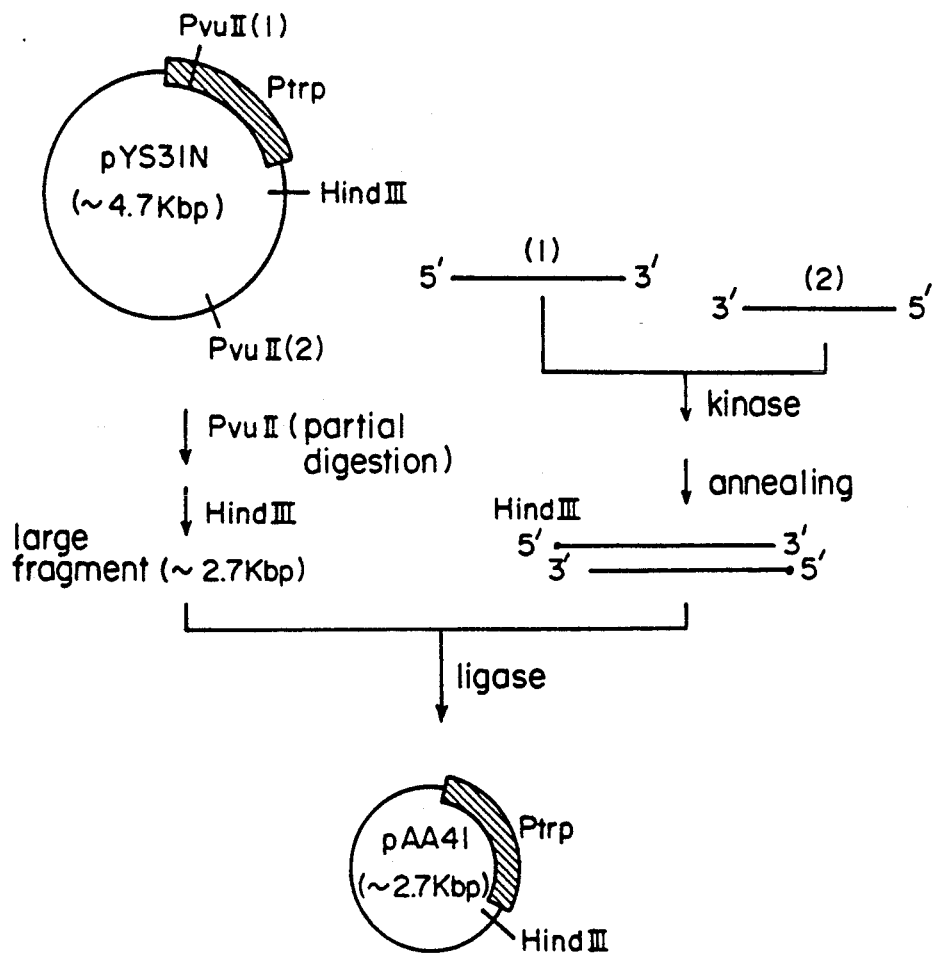

Fig. 8
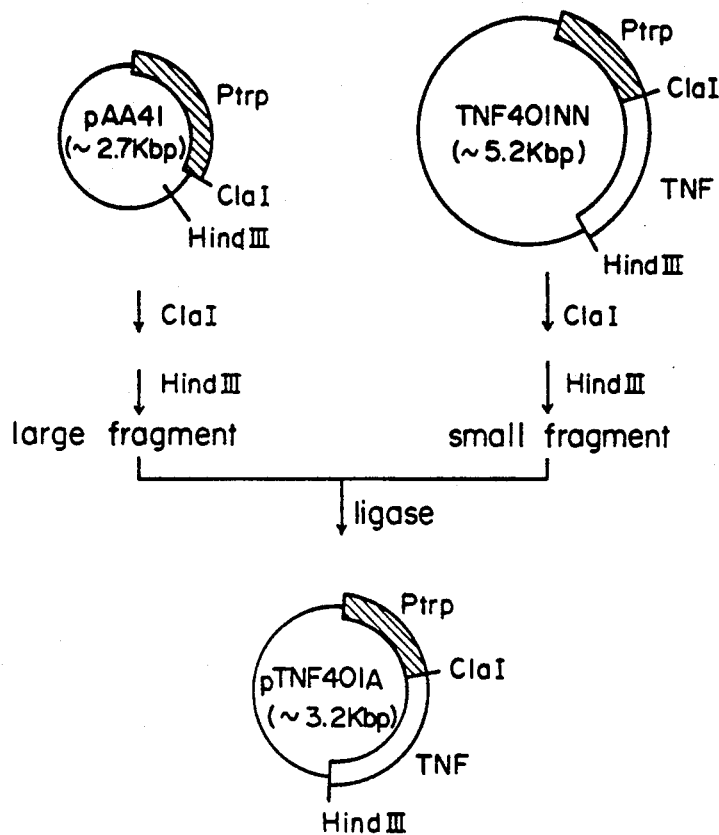
Fig. 9-A
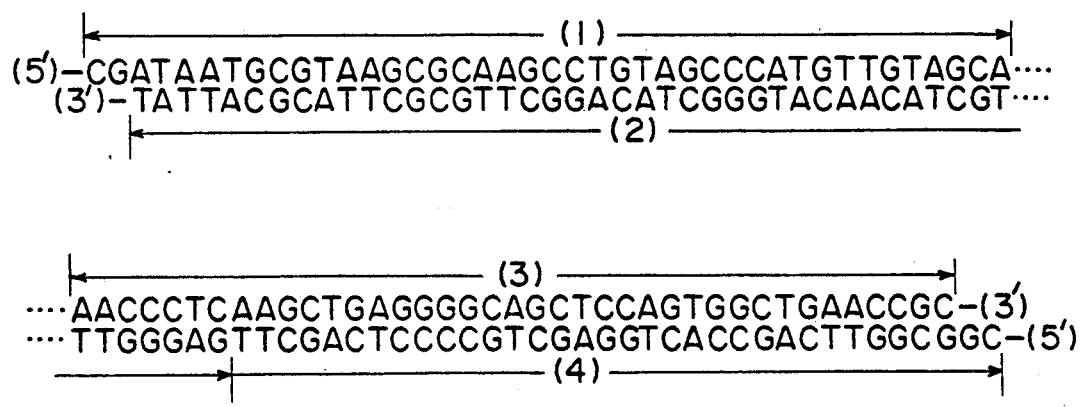

Fig. 9-B
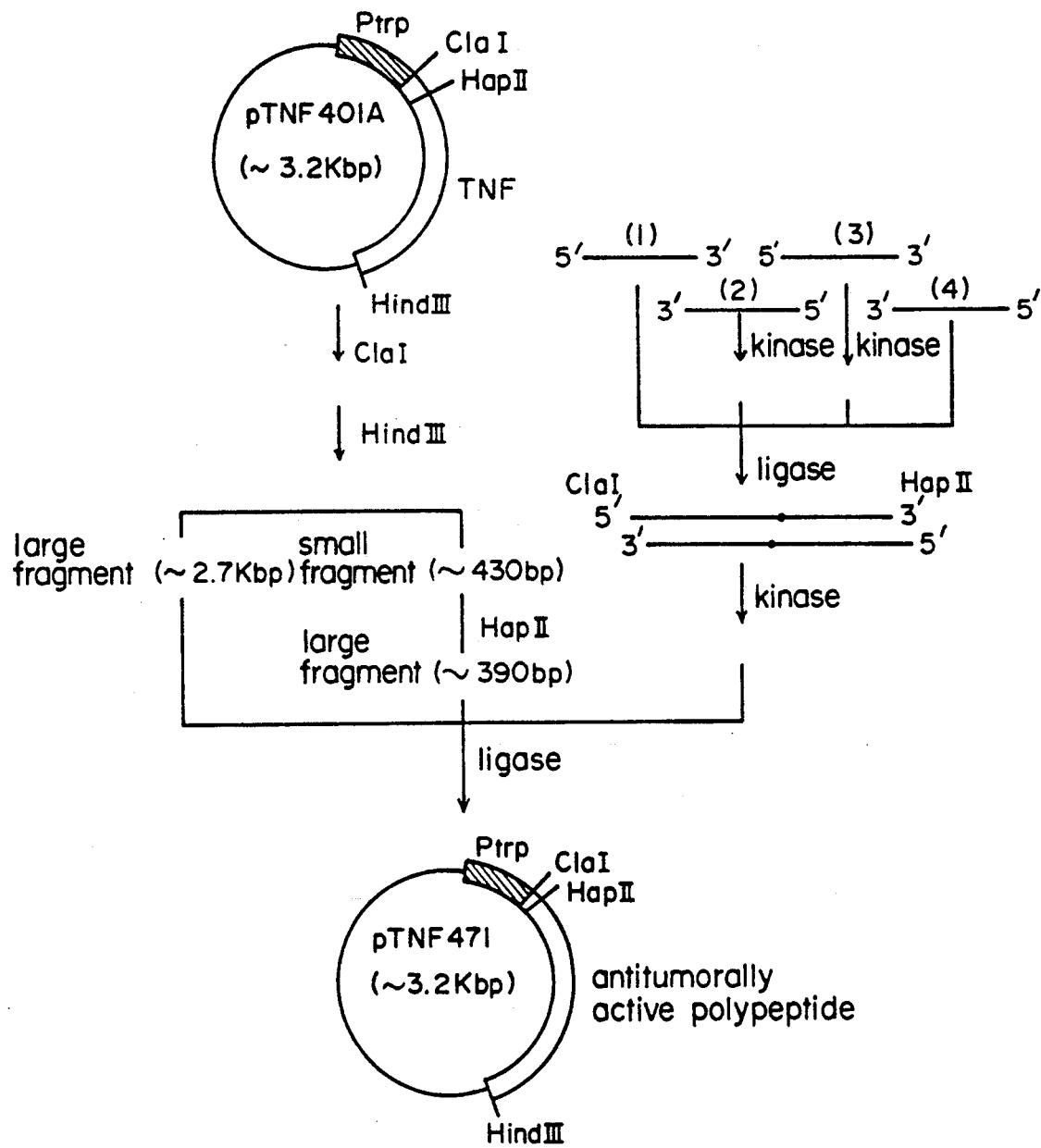

Fig. 10-A(1)
NO. 616
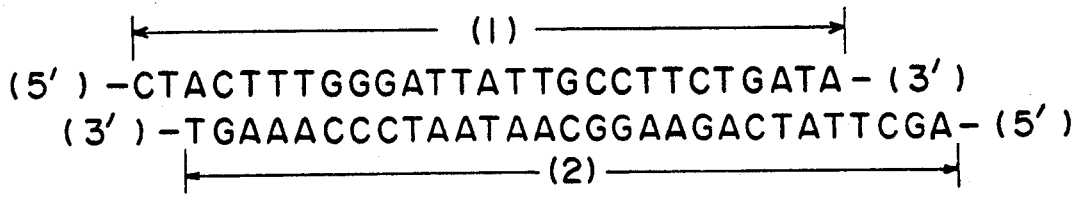
NO. 617
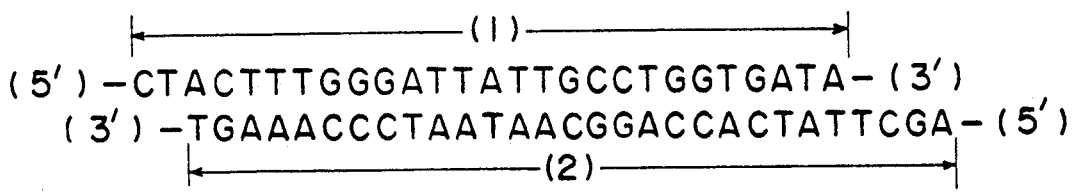
NO. 618
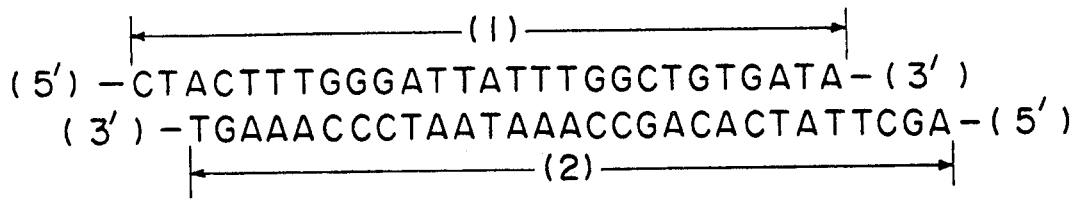
NO. 619
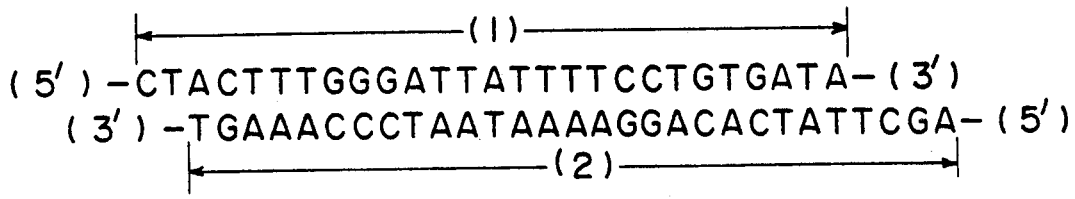

Fig. 10-A(2)
NO. 620
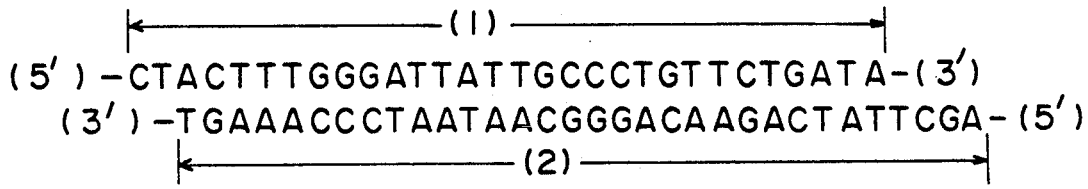
NO. 633
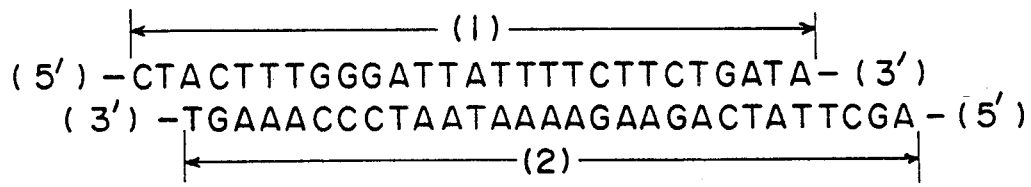
NO. 634
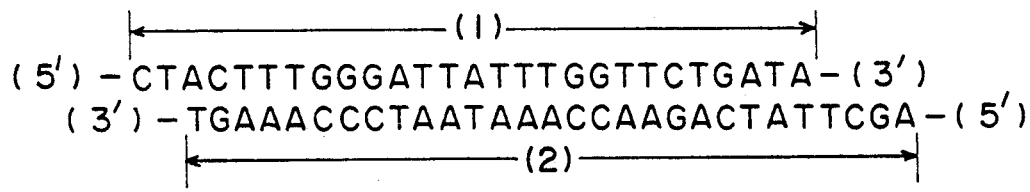
NO. 642
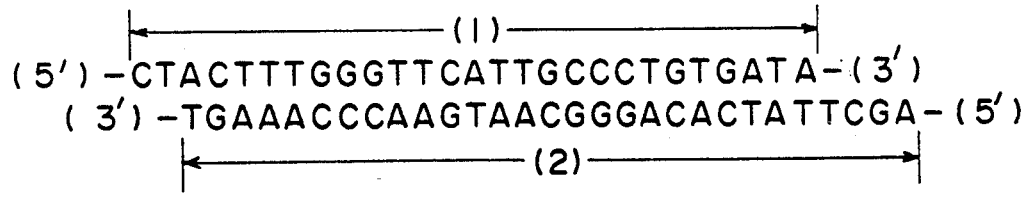
NO. 643
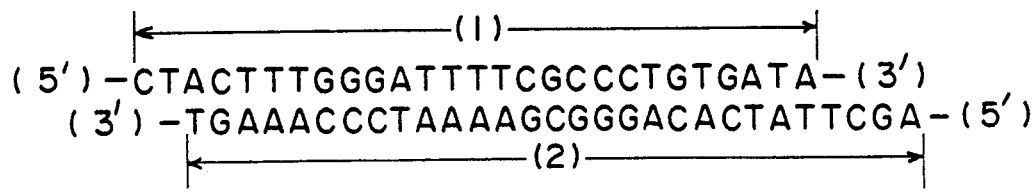

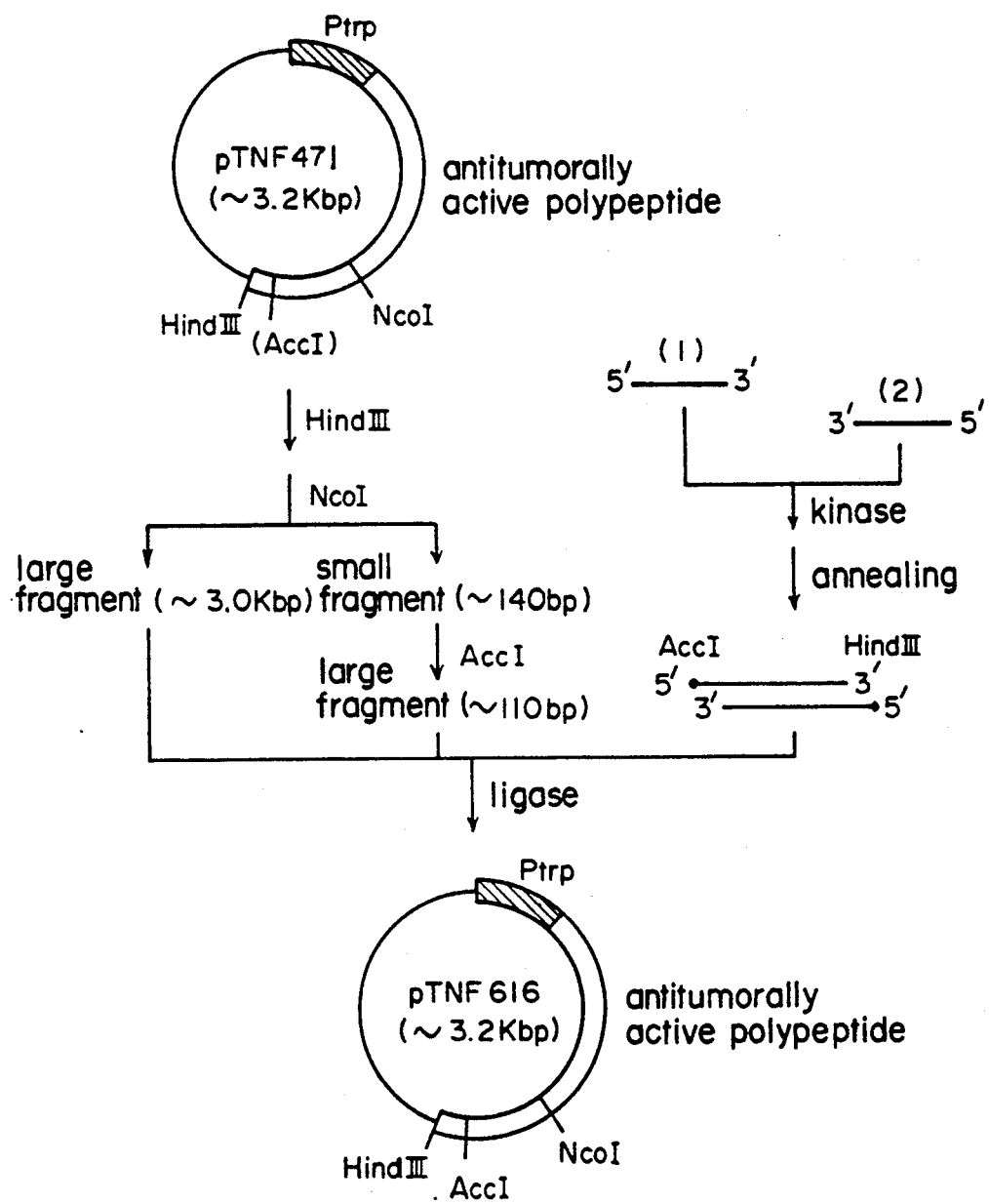
Fig. 10-B

Fig. 12-A
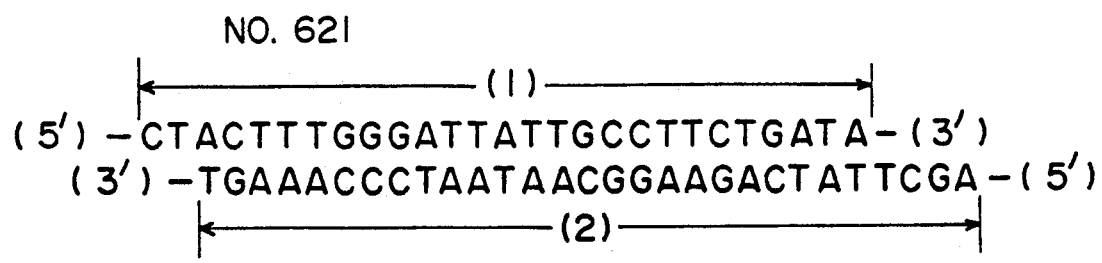
Fig. 12-B
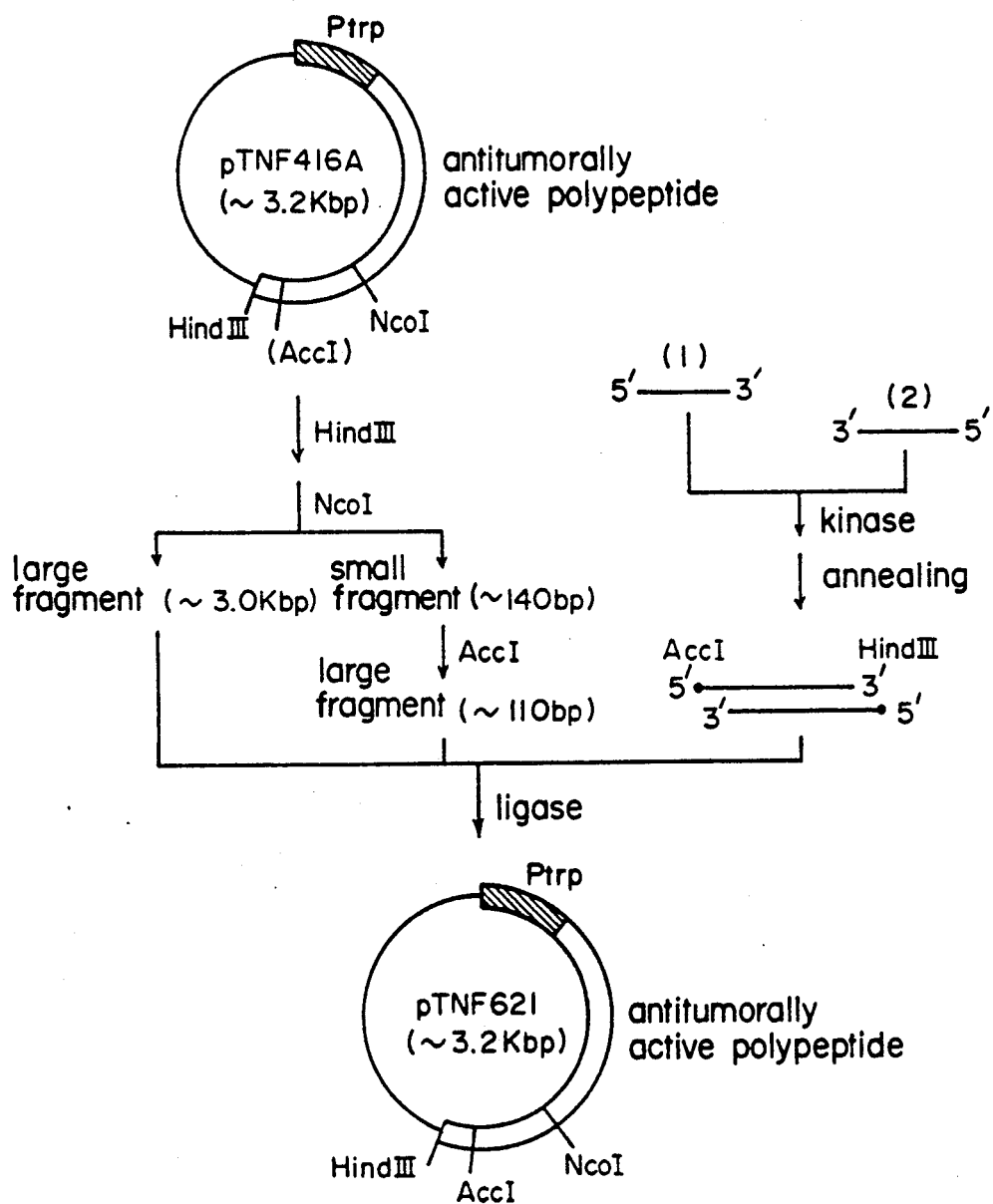

Fig. 13
NO. 622
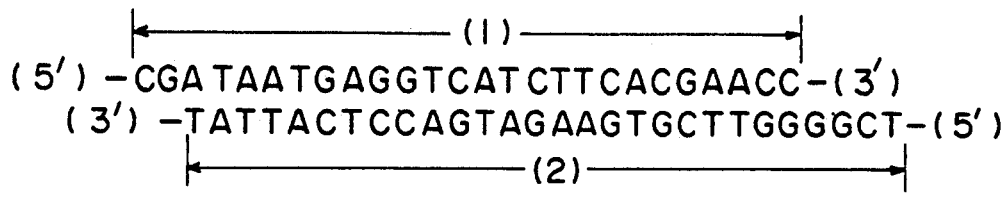
NO. 623
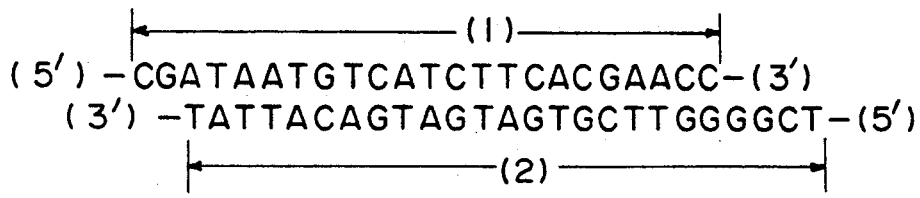
NO. 624
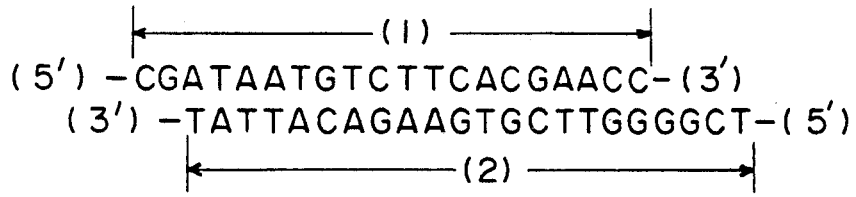
NO. 625
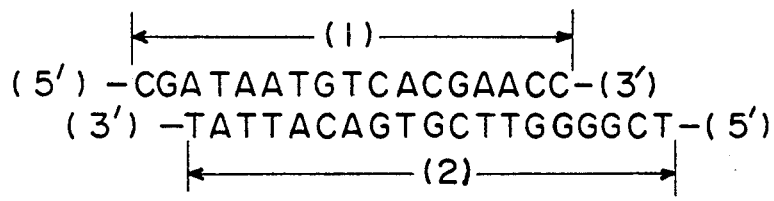
NO. 626
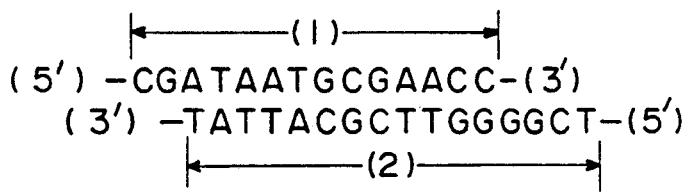
NO. 627
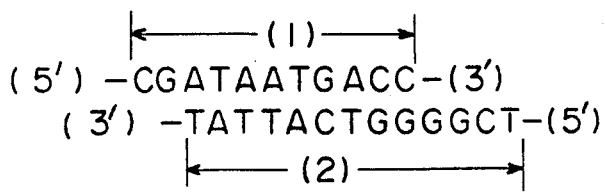

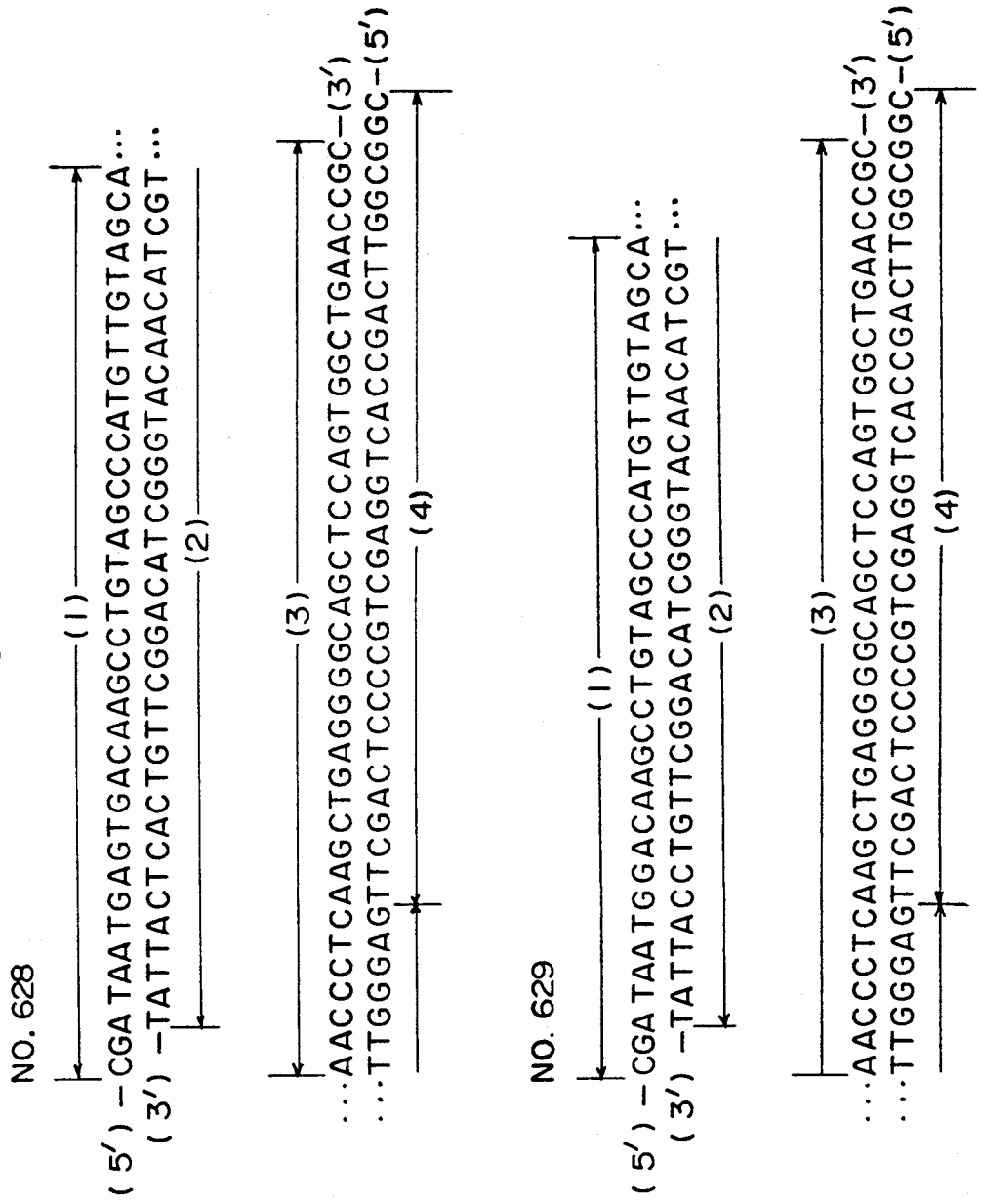

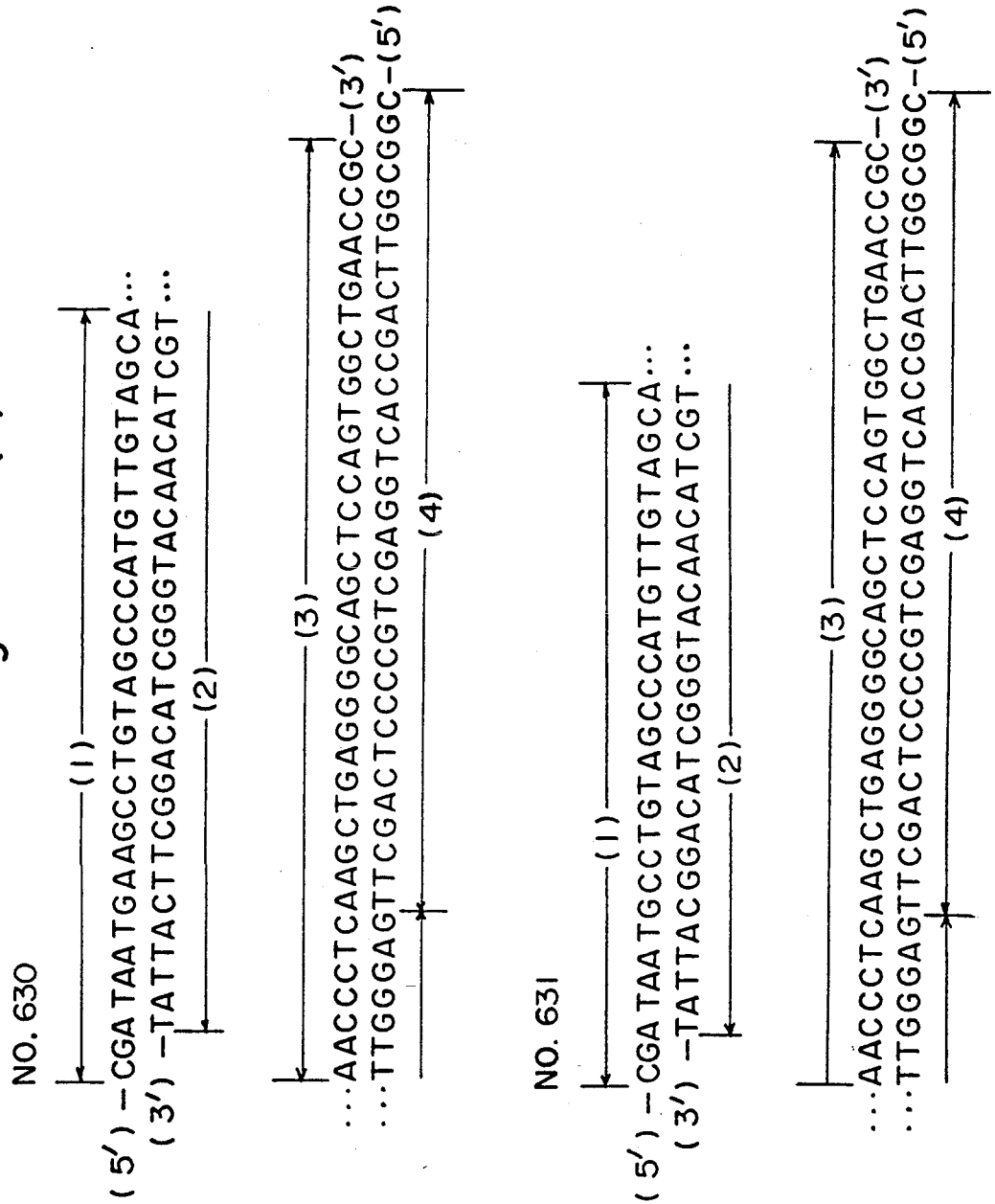
Fig. 14-A(2)

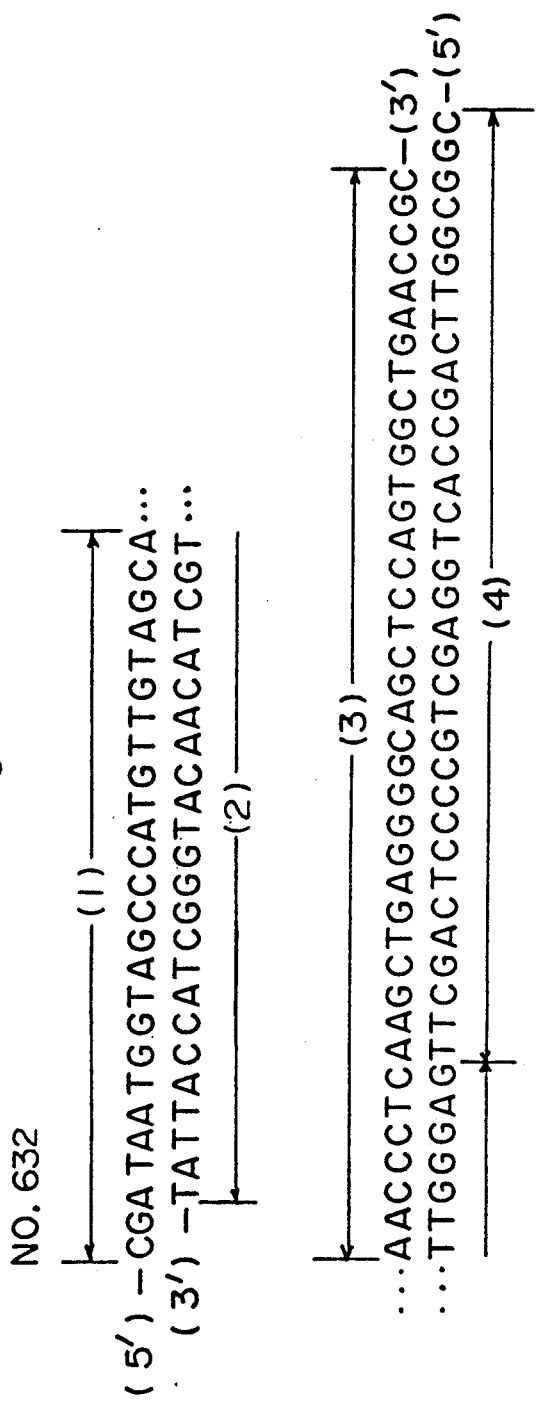
Fig. 14-A(3)

Fig. 14-B
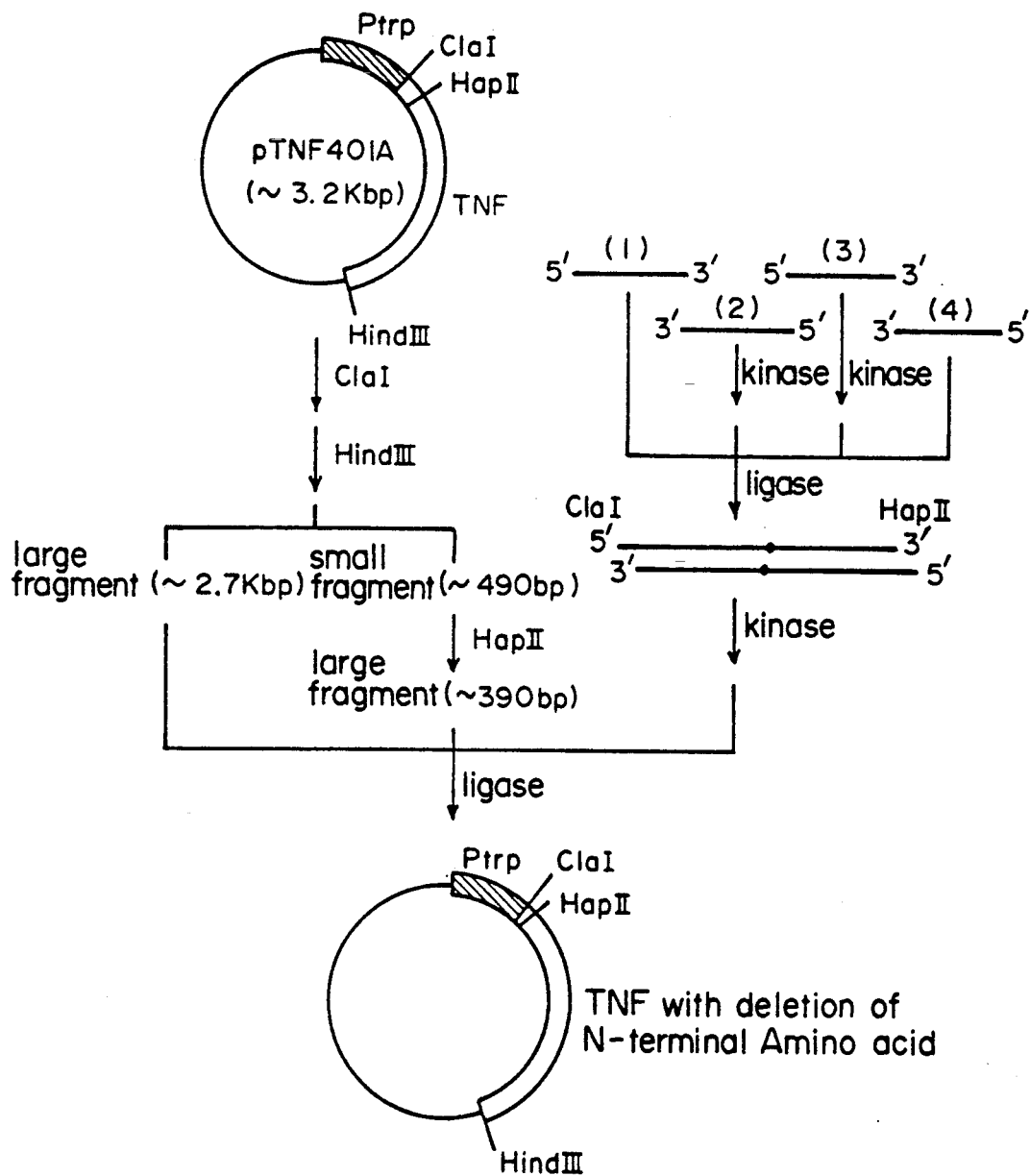

Fig. 15-A
KpnI (5')-CATCAGAGGACCTGTACCTCATCTACT⋯
     (3')-CATGGTAGTCTCCTGGACATGGAGTAGATGA⋯
⋯CCCAGGTCCTCTTCAAGGGCCAAGGCTGCCCG-(3')
⋯GGGTCCAGGAGAAGTTCCCGGTTCCGACGGGCAGCT-(5') SalI
Fig. 15-B
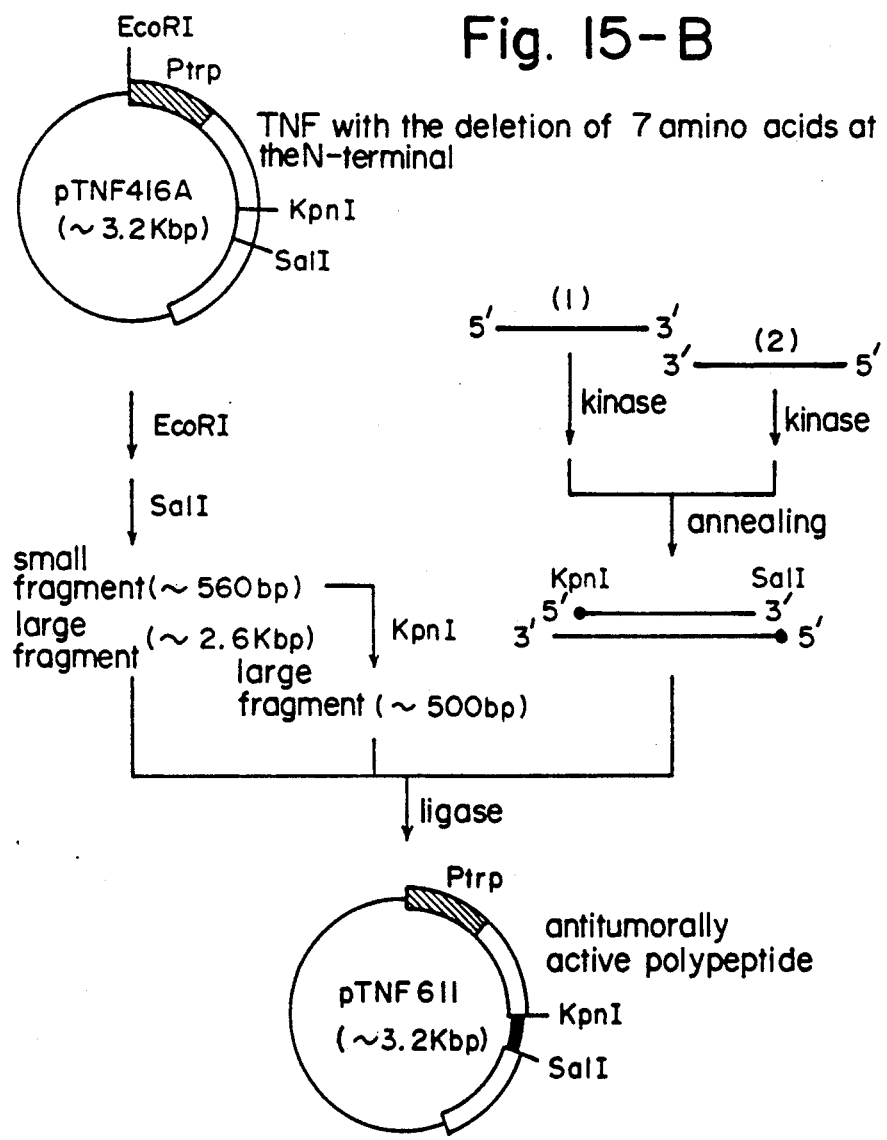

Fig. 16-A
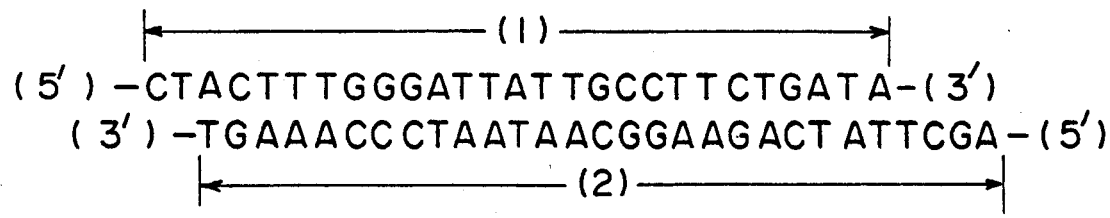
Fig. 16-B
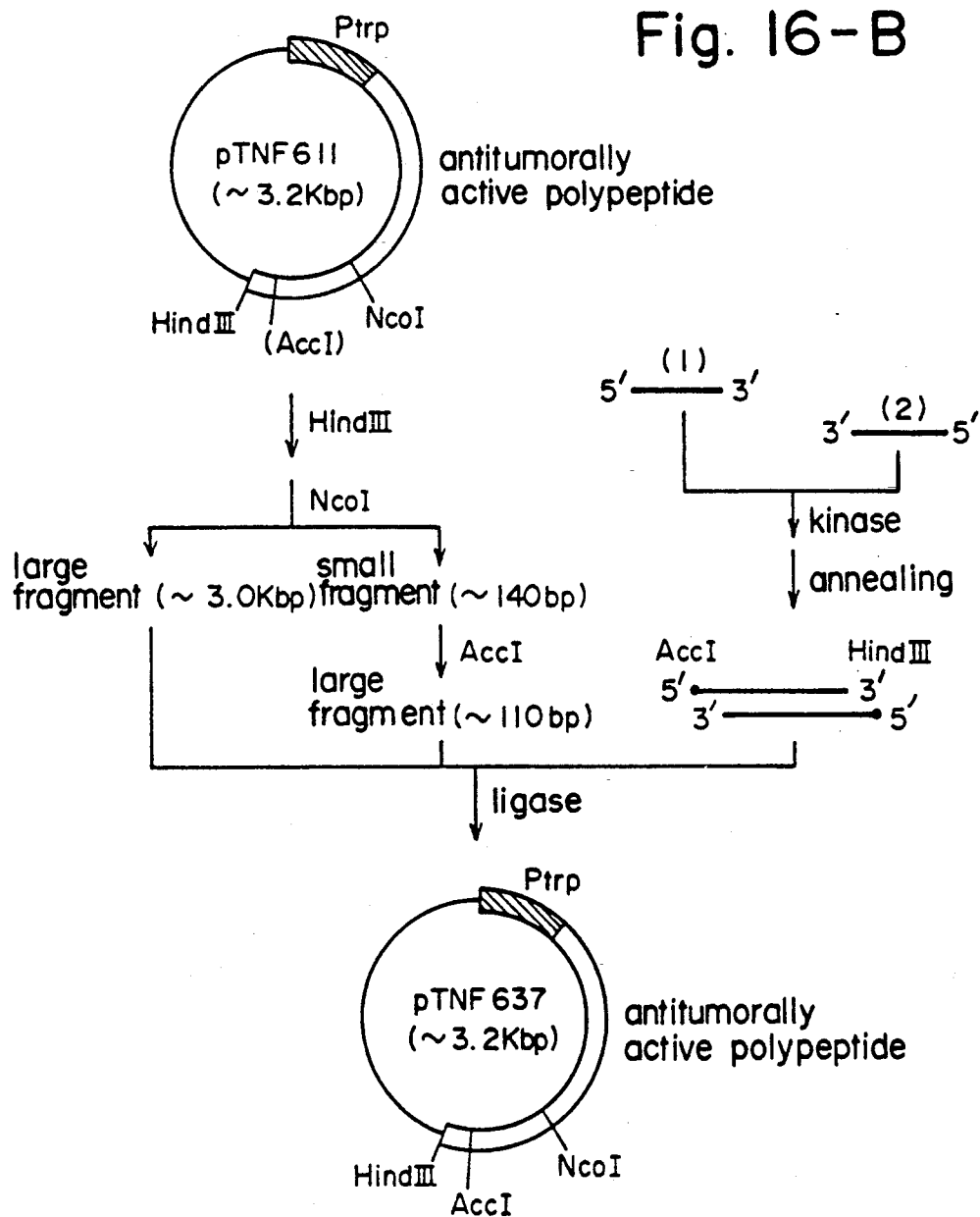

Fig. 17-A
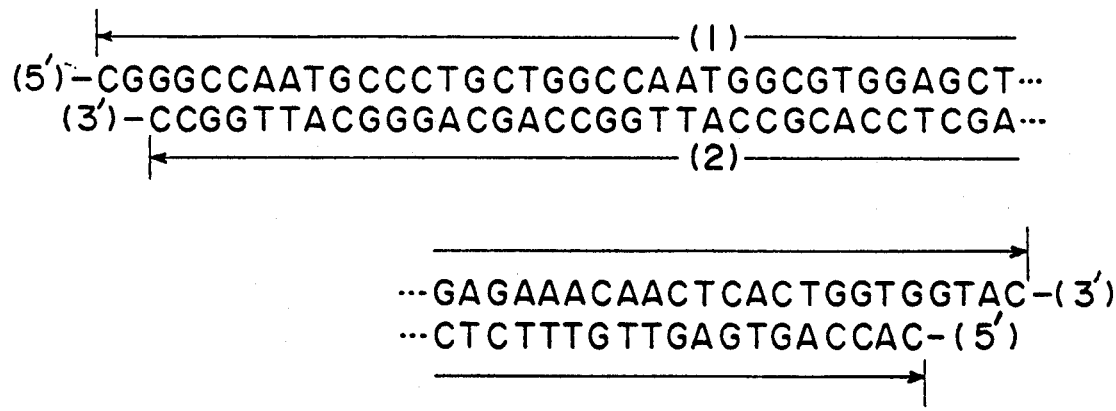
Fig. 17-B
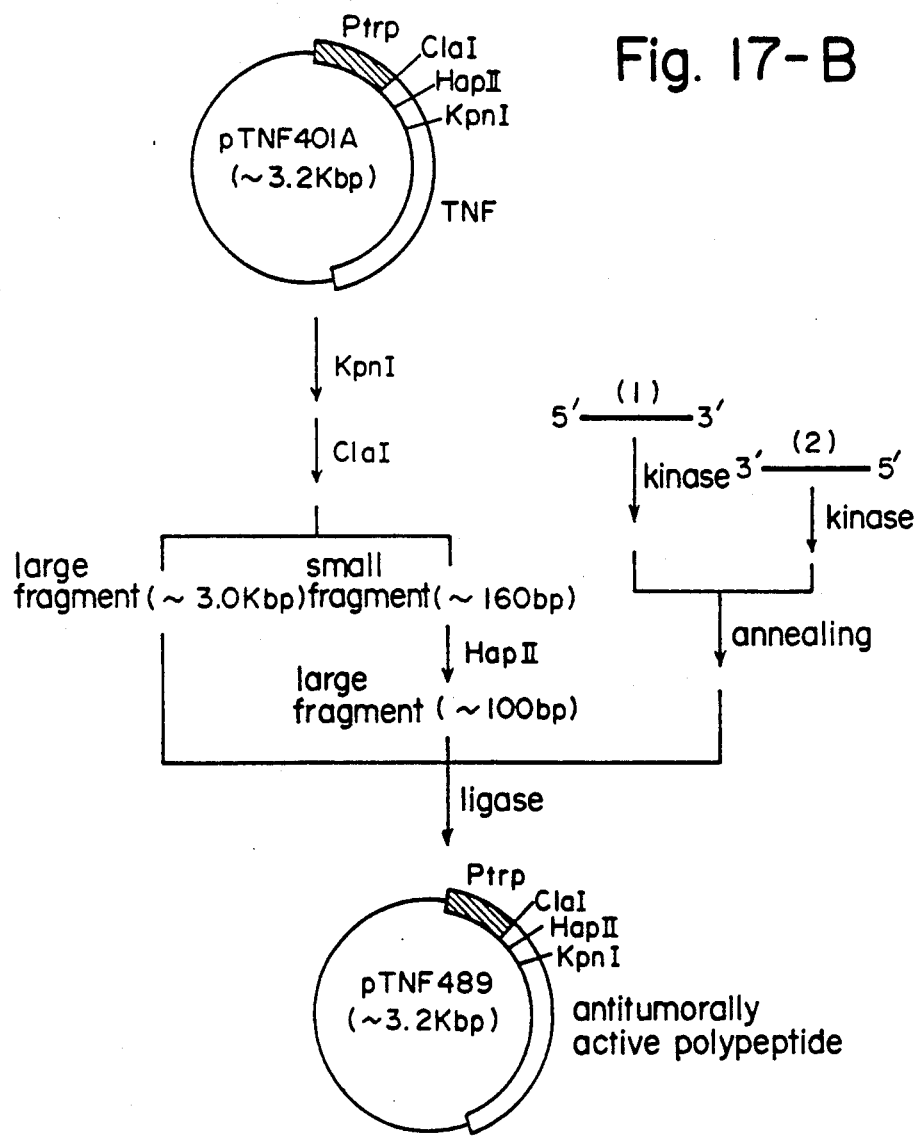

Fig. 19-A
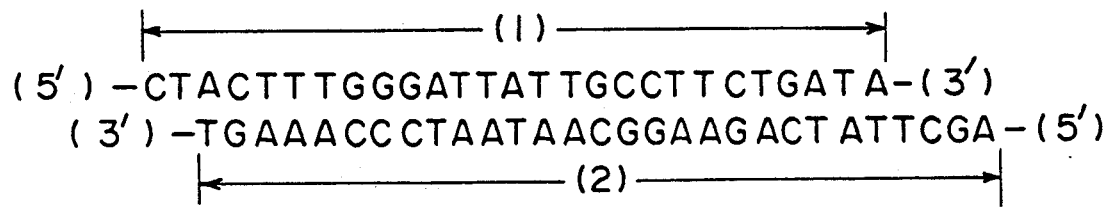
Fig. 19-B
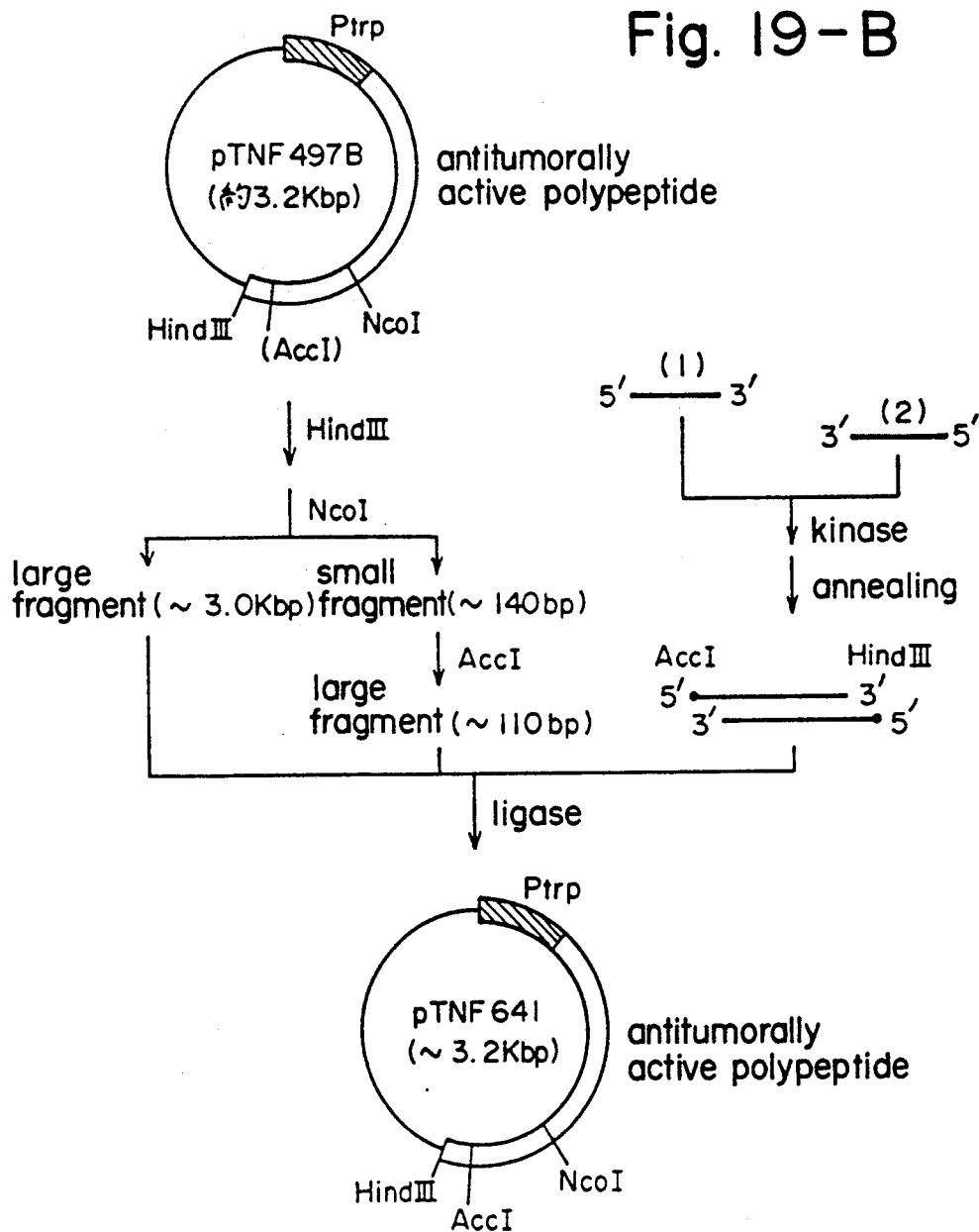

TERMINAL MODIFICATIONS OF TUMOR NECROSIS FACTOR

TECHNOLOGICAL FIELD

This invention relates to a novel physiologically active polypeptide, a recombinant plasmid containing a DNA region encoding the polypeptide, a recombinant microorganism transformed with the plasmid, a method of producing the polypeptide using the microorganism cell, use of the polypeptide and a method of recovering the purified polypeptide.

More specifically, it relates to a series of technologies in regard to a novel antitumorally active polypeptide.

In the present specification, an amino acid and a polypeptide will be described abbreviatingly by the method accepted by Committee on Biochemical Nomenclature (CBN) of IUPAC-IUB, and for example, the following abbreviations are used.
Ala: L-alanine
Arg: L-arginine
Asn: L-asparagine
Asp L-aspartic acid
Cys: L-cysteine
Gln: L-glutamine
Glu: L-glutamic acid
Gly: glycine
His: L-histidine
Ile: L-isoleucine
Leu: L-leucine
Lys: L-lysine
Met: L-methionine
Phe L-phenylalanine
Pro: L-proline
Ser: L-serine
Thr: L-threonine
Trp: L-tryptophan
Tyr: L-tyrosine
Val: L-valine A DNA sequence will be expressed by the bases contained in deoxyribonucleotides constituting it, and for example, the following abbreviations are used.
A: adenine (representing deoxyadenylic acid)
C: cytosine (representing deoxycytidylic acid)
G: guanine (representing deoxyguanylic acid)
T: thymine (representing deoxythymidylic acid)

($H_2N$)- and -(COOH) respectively show the amino-terminus and carboxy-terminus of an amino acid sequence, 5 and (5')- and (3')- respectively show the 5'-terminus and the 3'-terminus of a DNA sequence.

TECHNOLOGICAL BACKGROUND

Carswell et al. found that a serum sample taken from a mouse stimulated with Bacillus Calmette-Guerin (BCG) and then given an endotoxin contains a substance which bleeds and necrotizes a solid tumor caused by a transplanted Meth A sarcoma; and named this substance tumor necrosis factor (abbreviated as "TNF") (E. A. Carswell et al., Proc. Natl. Acad. Sci., U. S. A. 72, 3666 (1975)). TNF is found in many animals such as mice, rabbits and humans. Since it acts specifically on tumor cells of any species, it is expected to be used as an antitumor agent.

Recently, Pennica et al. disclosed the primary structure of a human TNF protein by cloning cDNA of human TNF, and reported on the expression of the human TNF gene in *Escherichia coli* (D. Pennica et al.: Nature, 312, 724 (1984)). Later, Shirai et al. (T. Shirai et al.: Nature, 313, 803 (1985)), Somura et al. [Somura et al.: Cancer and Chemotherapy, 12, 160 (1985)), Wang et al. (A. M. Wang et al.: Science, 228, 149 (1985)), and Marmenout et al. (A. Marmenout et al.: Eur. J. Biochem., 152, 515 (1985)) reported the expression of human TNF genes in *E. coli*.

Thus, large quantities of pure human TNF proteins have become available by using the genetic manipulation technology, and physiological activities of TNF other than the antitumor activity have been elucidated in more detail. For example, it was suggested that cachectin, a substance which is one cause of inducing cachexia in patients in the terminal stage of cancer or patients with serious infections, is very similar to TNF (B. Beulter et al.: "Nature", 316, 552 (1985)), and since cachectin has lipoprotein lipase inhibitory activity, the administration of TNF increases the amount of triglycerides in the blood, and may possibly induce side-effects such as hyperlipemia. Elsewhere, the influence of TNF on vascular endothelial cells (J. R. Gamble et al.: J. Exp. Med., 162, 2163 (1985)), and its bone absorbing action (D. R. Beltolini et al.: "Nature", 319, 516 (1986)) have been reported.

On the other hand, the recent advance in genetic manipulation technology has enabled gene recombination to substitute an amino acid in a useful protein by another amino acid, to add an amino acid or to delete an amino acid from it. A number of research works have been conducted for modifying a naturally occurring protein and creating proteins which meet a specific purpose.

On the other hand, with regard to the modification of human TNF proteins, a number of research works have been made; there have been reported substitution of either or both of amino acid residues of $CYs^{69}$ and $Cys^{101}$ by other amino acid residues in the amino acid sequence of human TNF proteins shown in FIG. 1 ( see PCT Application Laid-Open Specification W086/04606 and Japanese Laid-Open Patent Publication No. 263199/1987), substitution of $Gly^{122}$ by another amino acid residue (Japanese Laid-Open Patent Publication Nos. 263199/1987 and 93799/1988), and substitution of $Ala^{18}$ by another amino acid (Japanese Laid-open Patent Publication No. 87996/1988). Moreover, regarding the deletion of amino acids on the amino-terminus side, it has been reported that TNF in which amino acids Nos. 1 to 6 are deleted has antitumor activity (Japanese Laid-Open Patent Publication No. 50923/1986), that TNF in which amino acids Nos. 1 to 7 are deleted has antitumor activity (Japanese Patent Application No. 90087/1986), that TNF in which amino acids Nos. 1 to 10 are deleted has antitumor activity and the specific activity is highest in TNF's in which animo acids Nos. 1 to 6, 1 to 7 and 1 to 8 are deleted (PCT Application Laid-Open Specification W086/02381), that TNF in which amino acid Nos. 1 to 10 are deleted has antitumor activity (Japanese Laid-Open Patent Publication No. 272991/1987), that TNF in which amino acids Nos. 1 to 11 are deleted has cytotoxicity (Japanese Laid-Open Patent Publication No. 32486/1988), and that regarding TNF in which amino acids Nos. 1 to 7 are deleted, TNF with -Pro-Ser-Asp- amino acids Nos. 8 to 10 substituted by -Arg-Lys-Arg amino acids are much increased in the specific activity (Japanese Laid-Open Patent Publication No. 188396/1988).

Accordingly, the present inventors have made research works to produce novel modified human TNF proteins with a view to improving specific activity and stability, broadening a zone of a reaction spectrum and reducing side effects, and consequently arrived at the present invention.

OBJECTS OF THE INVENTION

A first object of this invention is to provide a novel polypeptide having antitumor activity.

A second object of this invention is to provide a polypeptide having increased antitumor activity.

Another object of this invention is to provide a recombinant plasmid containing a DNA region encoding the novel polypeptide of this invention.

Still another object of this invention is to provide a recombinant microorganism cell transformed with the recombinant plasmid, and a method of producing the polypeptide by cultivating the recombinant microorganism cell.

Yet another object of this invention is to provide a pharmaceutical composition containing the polypeptide.

A further object of this invention is to provide a method of recovering the purified polypeptide.

The other objects of this invention will be clarified from the following description.

DISCLOSURE OF THE INVENTION

According to the present inventors' research works, the objects and advantages of this invention can be achieved by providing a novel physiologically active polypeptide represented by formula (I) (SEQ ID NOS. 1-13 and 15-27)

$$(NH_2\text{-}(Met)_n\text{-}A\text{-}X\text{-}B\text{-}COOH) \ldots (I)$$

wherein
n is 0 or 1,
A denotes a bonding site, -Asp-, -Ser-Asp-, -Pro-Ser-Asp- or -Arg-Lys-Arg-,
B denotes -Ile-Ile-Ala-Phe-, -Ile-Ile-Ala-Trp-, -Ile-Ile-Ala-Leu-Phe-, -Ile-Ile-Trp-Leu-, Ile-Ile-Phe-Leu-, -Ile-Ile-Phe-Phe-, -Ile-Ile-Trp-Phe-, -Ile-Phe-Ala-Leu- or -Phe-Ile-Ala-Leu-, provided when A is a bonding site, -Asp-, -Ser-Asp- or -Pro-Ser-Asp-, B is -Ile-Ile-Ala-Phe, and
X denotes -Lys-Pro-Val-Ala-His-Val-Val-Ala-Asn-Pro-Gln-Ala-Glu-Gly-Gln-Leu-Gln-Trp-Leu-Asn-Arg-Arg-Ala-Asn-Ala-Leu-Leu-Ala-Asn-Gly-Val-Glu-Leu-Arg-Asp-Asn-Gln-Leu-Val-Val-Pro-Ser-Glu-Gly-Leu-Tyr-Leu-Ile-Tyr-Ser-Gln-Val-Leu- Phe-Lys-Gly-Gln-Gly-Cys-Pro-Ser-Thr-His-Val-Leu-Leu-Thr-His-Thr-Ile-Ser-Arg-Ile-Ala-Val-Ser-Tyr-Gln-Thr-Lys-Val-Asn-Leu-Leu-Ser-Ala-Ile-Lys-Ser-Pro-Cys-Gln-Arg-Glu-Thr-Pro-Glu-Gly-Ala-Glu-Ala-Lys-Pro-Trp-Tyr-Glu-Pro-Ile-Tyr-Leu-Gly- Gly-Val-Phe-Gln-Leu-Glu-Lys-Gly-Asp-Arg-Leu-Ser-Ala-Glu-Ile-Asn-Arg-Pro-Asp-Tyr-Leu-Asp-Phe-Ala-Glu-Ser-Gly-Gln-Val-Tyr-Phe-Gly-.

and a recombinant plasmid containing a DNA region encoding the polypeptide, as well as a recombinant microorganism cell transformed with the thus obtained recombinant plasmid, a method of producing the polypeptide of formula (I) by cultivating the microorganism cell, a pharmaceutical composition containing the polypeptide and a method of purifying and recovering the aforesaid polypeptide.

This invention will be described in more detail below.

The novel polypeptide represented by formula (I)

$$(NH_2)\text{-}(Met)_n\text{-}A\text{-}X\text{-}B\text{-}(COOH) \quad (I)$$

wherein n, A, X and B are as defined above, in this invention is characterized in that both the amino-terminus and the carboxy-terminus in human TNF having a sequence of 157 amino acids Nos. 1 to 157 as shown in FIG. 1 are modified.

This point will be more specifically described. In formula (I), the unit -X- agrees with the amino acid sequence from No. 11 Lys to No. 153 Gly in the amino acid sequence of human TNF in FIG. 1. However, said polypeptide features that the $(Met)_n$-A- unit is bound to the amino-terminus and the -B- unit to the carboxy-terminus in the amino acid sequence of this -X- and the amino acid sequences of both the terminus are not the same as those of both the terminus in the amino acid sequence of human TNF in FIG. 1.

Thus, the polypeptide of formula (I) in this invention specifically contains the following amino acid sequences (i) to (xiii) wherein n and x are as defined in formula [I].

(i)—$(Met)_n$—X—Ile—Ile—Ala—Phe—(SEQ ID NOS. 1 and 15)
(ii)—$Met)_n$—Asp—X—Ile—Ile—Ala—Phe—(SEQ ID NOS. 2 and 16)
(iii)—$(Met)_n$—Ser—Asp—X—Ile—Ile—Ala—Phe—(SEQ ID NOS. 3 and 17)
(iv)—$(Met)_n$—Pro—Ser—Asp—X—Ile—Ile—Ala—Phe—(SEQ ID NOS. 4 and 18)
(v)—$(Met)_n$—Arg—Lys—Arg—X—Ile—Ile—Ala—Phe—(SEQ ID NOS. 5 and 19)
(vi)—$(Met)_n$—Arg—Lys—Arg—X—Ile—Ile—Ala—Trp—(SEQ ID NOS. 6 and 20)
(vii)—$(Met)_n$—Arg—Lys—Arg—X—Ile—Ile—Ala—Leu—Phe—(SEQ ID NOS. 7 and 21)
(viii)—$(Met)_n$—Arg—Lys—Arg—X—Ile—Ile—Trp—Leu—(SEQ ID NOS. 8 and 22)
(ix)—$(Met)_n$—Arg—Lys—Arg—X—Ile—Ile—Phe—Leu—(SEQ ID NOS. 9 and 23)
(x)—$(Met)_n$—Arg—Lys—Arg—X—Ile—Ile—Phe—Phe—(SEQ ID NOS. 10 and 24)
(xi)—$(Met)_n$—Arg—Lys—Arg—X—Ile—Ile—Trp—Phe—(SEQ ID NOS. 11 and 25)
(xii)—$(Met)_n$—Arg—Lys—Arg—X—Ile—Phe—Ala—Leu—(SEQ ID NOS. 12 and 26)
(xiii)—$(Met)_n$—Arg—Lys—Arg—X—Phe—Ile—Ala—Leu—(SEQ ID NOS. 13 and 27)

The amino acid sequences (i) to (xiii) are roughly divided into (1) a group consisting of (v) to (xiii) in which the amino-terminus [$(Met)_n$-A-] is -$(Met)_n$-Arg-Lys-Arg- and (2) a group consisting of (i) to (iv) in which the amino-terminus is different from -$(Met)_n$-Arg-Lys-Arg- and the carboxy terminus [-B-] is -Ile-Ile-Ala-Phe-.

Of the polypeptides represented by formula [I] in this invention, a polypeptide comprising a group of (v) to (xiii) in which the amino acid sequence of the amino-terminus is -$(Met)_n$-Arg-Lys-Arg- is preferable to that comprising the other group. Moreover, a polypeptide of (v), (vi), (viii) or (ix) in which the amino acid sequence of the amino-terminus is -$(Met)_n$-Arg-Lys-Arg and the amino acid sequence of the carboxy-terminus is
-Ile-Ile-Ala-Phe-,
-Ile-Ile-Ala-Trp-,
-Ile-Ile-Trp-Leu- or
-Ile-Ile-Phe-Leuis most preferable because of its highest antitumor activity.

The polypeptide of this invention is, as shown above, represented by formula (I) wherein -X- is not modified in comparison to the amino acid sequence of from No. 11 Lys to No. 153 Gly in the amino acid sequence of human TNF (see FIG. 1). In the polypeptide of this invention, however, the amino acid sequence of this -X- permits some modification (e.g. substitution, deletion or addition) unless impairing the objects of this invention. For example, a polypeptide in which No. 45 Asp is substitued by Asn and No. 47 Gly by Ser or No. 54 Gly by Asp in the amino acid sequence (iv) still has the same activity as a polypeptide with unsubstituted -X-.

Moreover, according to this invention, there is provided a plasmid that has a DNA sequence encoding the polypeptide of formula [I].

The plasmid of this invention is such that the intended polypeptide of formula (I) is produced by a microorganism cell obtained by transforming it in a host. Said plasmid contains not only the DNA sequence encoding the poly peptide of formula (I) but also varied signal sequences used to express performance of vectors and control sequences of transcription and translation (e.g. an initiation codon, a termination codon, an initiator, a terminator, an enhancer and a promotor).

According to this invention, there is thus provided a plasmid containing double-stranded DNA comprising single-stranded DNA and supplemental single-stranded DNA as represented by formula (II):

$$(5')\text{-}(Yc)_p\text{-}Ac\text{-}Xc\text{-}Bc\text{-}(Zc)_q\text{-}(3') \quad \text{(II)}$$

In the DNA sequence of formula (II), -Ac-, -Xc- and -Bc- correspond respectively to DNA sequence portions encoding the amino acid sequences -A-, -X- and -B- in the polypeptide of formula (I). Yc and Zc mean signal sequences and/or control sequences of transcription and translation.

Thus, p or q in formula [II] is an optimum number for one gene expression with good efficiency and is independently selected from 0, 1, 2 and 3. DNA sequences -Yc-, -Ac-, -Xc-, -Bc- and -Zc- are concretely shown below. However, they are one examples, and the DNA sequences introduced into the plasmid of this invention are not limited thereto.

First of all, as -Ac- and -Bc- in formula (II) are encoded in the amino acid sequences -A- and -B- in formula (I), the DNA sequences are shown to correspond to same.

| —A— | —Ac— |
|---|---|
| —(bonding site) | — |
| —Asp— | —GAC— |
| —Ser—Asp— | —AGTGAC— |
| —Pro—Ser—Asp— | —CCGAGTGAC— |
| —Arg—Lys—Arg— | —CGTAAGCGC— |

| —B— | —Bc— |
|---|---|
| —Ile—Ile—Ala—Phe— | —ATTATTGCCTTC—(SEQ ID NO. 39) |
| —Ile—Ile—Ala—Trp— | —ATTATTGCCTGG—(SEQ ID NO. 40) |
| —Ile—Ile—Ala—Leu—Phe— | —ATTATTGCCCTGTTC—(SEQ ID NO. 41) |
| —Ile—Ile—Trp—Leu— | —ATTATTTGGCTG—(SEQ ID NO. 42) |
| —Ile—Ile—Phe—Leu— | —ATTATTTTCCTG—(SEQ ID NO. 43) |
| —Ile—Ile—Phe—Phe— | —ATTATTTTCTTC—(SEQ ID NO. 44) |
| —Ile—Ile—Trp—Phe— | —ATTATTTGGTTC—(SEQ ID NO. 45) |
| —Ile—Phe—Ala—Leu— | —ATTTTCGCCCTG—(SEQ ID NO. 46) |
| —Phe—Ile—Ala—Leu— | —TTCATTGCCCTG—(SEQ ID NO. 47) |

The DNA sequence of -Xc- encodes the amino acid sequence of -X- in formula (I) as shown below.

—Xc— (SEQ ID. NO. 48)

—A A G C C T G T A G C C C A T G T T G T A G C A A A C C

C T C A A G C T G A G G G G C A G C T C C A G T G G C T G

A A C C G C C G G G C C A A T G C C C T G C T G G C C A A

T G G C G T G G A G C T G A G A G A T A A C C A G C T G G

T G G T A C C A T C A G A G G G C C T G T A C C T C A T C

T A C T C C C A G G T C C T C T T C A A G G G C C A A G G

C T G C C C G T C G A C C C A T G T G C T C C T C A C C C

A C A C C A T C A G C C G C A T C G C C G T C T C C T A C

C A G A C C A A G G T C A A C C T C C T C T C T G C G A T

C A A G A G C C C C T G C C A G A G G G A G A C C C C A G

A G G G G G C T G A G G C C A A G C C A T G G T A T G A G

C C C A T C T A T C T G G G A G G G G T C T T C C A G C T

G G A G A A G G G T G A C C G A C T C A G C G C T G A A A

T C A A T C G G C C C G A C T A T C T C G A C T T T G C C

GAGTCTGGGCAGGTCTACTTTGGG—

-Yc- and -Zc- in formula [II] can be the following DNA sequences.

$$-\underset{-Xc-}{CATCATAACGGTTCTGGCAAATATTCTG}$$
AAATGAGCTGTTGACAATTAATCATCGAA
CTAGTTAACTAGTACGCAAGTTCACGTAA
AAAGGGTATCGATAATG—

(SEQ ID. NO. 49)

$$-\underset{-Zc-}{TGATAAGCTTAGCCCGCCT}AATGAGCGG$$
GCTTTTTTTT—

(SEQ. ID NO. 50)

The unit -Ac-Xc-Bc- in formula (II) is at least a DNA sequence encoding the polypeptide of formula (I) in this invention.

According to this invention, the DNA sequence of formula (II) is introduced into a vector plasmid to obtain a recombinant plasmid. Examples of the vector plasmid used in that case are a vector for *Escherichia coli*, a vector for *Bacillus subtilis*, and a vector for yeast. Above all, the vector for *Eschericia coli* is in general advantageously utilized. Examples of the vectors available to produce the plasmid are shown below. The parenthesized descriptions of the following vectors show depositories and numbers, makers or literature's names.

Vectors (i) Vectors for *Escherichia coli* pBR322(ATCC 31344), pBR329(ATCC 37264), pACYC184(ATCC 37033), pDR540(ATCC 37282), pMB9(ATCC 37019), pDR720(Pharmacia), pUC9(ATCC 37252), pUC19(ATCC 37254), pUC13(Pharmacia), pPL-lambda(-Pharmacia), pKK223-3(Pharmacia), pYS31N(S.-Nakamura et al., J. Biotechnol., 8, 14 (1988)), pAA41(T. Masegi et al., Argic. Biol. Chem., 52, 1609 (1988))

Of these, pYS31N or pAA41 is preferable.

(ii) Vectors for *Bacillus subtilis*

For example, pBS7(ATCC 37280), pC194(ATCC 37034), pE194(ATCC 37128).

(iii) Vectors for yeast

For example, YEp13(ATCC 31125), YCp19(ATCC 37364), YRp7(ATCC 37060), YIp32(ATCC 37052), YRp17(ATCC 37078).

As is clear from the following description and Examples, this invention produces 13 recombinant plasmids that contain DNA sequences encoding the concrete amino acid sequences of the polypeptide of formula [I]. A relationship between numbers of the resulting recombinant plasmids and numbers of the amino acid sequences is shown below.

| Amino acid sequence No. | Recombinant plasmid No. |
|---|---|
| (i) | pTNF630 |
| (ii) | pTNF629 |
| (iii) | pTNF628 |
| (iv) | pTNF621 |
| (v) | pTNF616 |
| (vi) | pTNF617 |
| (vii) | pTNF620 |
| (viii) | pTNF618 |
| (ix) | pTNF619 |
| (x) | pTNF633 |
| (xi) | pTNF634 |
| (xii) | pTNF643 |
| (xiii) | pTNF642 |

Among the recombinant plasmids of this invention, (v) to (viii) are preferable, and (v) pTNF616, (vi) pTNF617, (viii) pTNF618 and pTNF619 are especially preferable.

The microorganism cell transformed with the recombinant plasmid in this invention may be that which can produce the polypeptide of formula (I) by the DNA sequence of formula (II) introduced into the plasmid. Examples thereof are *Escherichia coli*, *Bacillus subtilis* and yeast. Of there, *Escherichia coli* is preferable. Concrete examples of *Escherichia coli* include C600r-m-(ATCC 33525), HB101 (ATCC 33694), W3110 (ATCC 27325), DH1(ATCC 33849), JA221 (ATCC 33875), JM101 (ATCC 33876), (ATCC 31244), RR1 (ATCC 31343) and LE392 (ATCC 33573).

Further, according to this invention, there is provided a method of recovering a purified polypeptide from an aqueous solution containing a polypeptide represented by formula (III) (SEQ ID NOS. 5-14 and 19-28)

$$(NH_2)\text{-}(Met)_n\text{-}A'\text{-}X\text{-}B'\text{-}(COOH) \qquad (III)$$

wherein n is 0 or 1,

A' denotes -Arg-Lys-Arg-,

B' denotes -Ile-Ile-Ala-Phe-, Ile-Ile-Ala-Trp-, -Ile-Ile-Ala-Leu-Phe-, -Ile-Ile-Trp-Leu-, -Ile-Ile-Phe-Leu-, -Ile-Ile-Phe-Phe-, -Ile-Ile-Trp-Phe-, -Ile-Phe-Ala-Leu-, -Phe-Ile-Ala-Leu or -Ile-Ile-Ala-Leu-, and X denotes the same amino acid sequence as in formula (I).

That is, the purified polypeptide of formula (III) can be recovered by easy, simple operation which comprises cultivating an aqueous solution containing the polypeptide of formula (III), e.g. a culture supernatant or a microorganism cell producing this polypeptide, then subjecting it to cell sonication, and subjecting the resulting lysate to the steps of (1) contacting it with a cation exchange resin and adsorbing the polypeptide to the cation exchange resin, (2) rinsing the cation exchange resin to which the polypeptide is adsorbed with a solvent containing a salt in such concentration that the polypeptide is substantially not eluted, and (3) then eluting the cation exchange resin to which the polypeptide is adsorbed with a solvent containing a salt in such concentration that the polypeptide can be eluted.

It is thought that such purifying and recovering method of this invention can be achieved because the amino acid sequence of the amino-terminus is -Arg-Lys-Arg- as is the case with the polypeptide of formula (III). Even if the aqueous solution containing the polypeptide of human TNF shown in FIG. 1 attached hereto is subjected to the treating steps (1) to (3), a purified polypeptide cannot be obtained.

To explain briefly, the method of purifying and recovering the polypeptide in this invention comprises adsorbing the polypeptide of formula (III) to the cation exchange resin, rinsing it with a solvent containing a salt in such relatively low concentration that the adsorbed polypeptide is substantially not eluted and then eluting the adsorbed polypeptide upon increasing the salt concentration.

That the cation exchange resin can be used as a cation exchange column chromatography in the method of purifying and recovering the polypeptide is excellent in conducting purification on an industrial scale in that it is easy to make the polypeptide pyrogen-free and adsorption capacity is high.

The aqueous solution containing the polypeptide of formula (III), which is subjected to the purifying and recovering method in this invention is a lysate obtained by collecting recombinant microorganism cells producing the polypeptide by centrifugation, suspending them in a suitable buffer, rupturing the cells with an ultrasonic generator and conducting centrifugation, or a sample formed by solubilizing an insoluble fraction obtained in the same manner via a suitable method. Or an aqueous solution formed by dialyzing a culture solution of a recombinant microorganism cell secreting and producing the polypeptide against a suitable buffer.

As the cation exchange resin used in the step (1), a strongly acidic or weakly acidic cation exchange resin can be taken. Concrete examples thereof are sulfopropyl cephalose, carboxymethyl cephalose and phosphocephalose.

The cation exchange resin can be used in an ordinary particulate, fibrous or membraneous form. Actually it is preferably used as a cation exchange column chromatography.

The polypeptide is adsorbed on the surface of the cation exchange resin by contacting the solution containing the polypeptide with the cation exchange resin. Since impurities other than the final polypeptide are adsorbed or adhered to the resulting adsorbed cation exchange resin, it is rinsed with a solvent containing a salt in such concentration that the adsorbed final polypeptide is substantially not eluted.

As the salt-containing solvent used in the rinsing of step (2), a buffer with a salt concentration adjusted by a salt such as sodium chloride is employed. The buffer can be a phosphate or tris-hydrochloride buffer with pH adjusted to the vicinity of neutrality. Concrete examples thereof are a 20 mM phosphate buffer (pH 7.4) and a 20 mM tris-hydrochloride buffer (pH 7.4).

The salt concentration is preferably at least 0.1 M but less than 0.15 M. When it is less than 0.1 M, it is difficult to completely rinse impurities except the final polypeptide. When it exceeds 0.15 M, there is a possibility of eluting the final polypepride.

After rinsing, the final polypeptide is eluted from the cation exchange resin to which the final polypeptide is adsorbed using a solvent containing a salt in such concentration as to elute the final polypeptide.

The salt-containing solvent used in the elution of step (3) is used in the form of a buffer in which the salt concentration is more increased than in the rinsing solution by a salt such as sodium chloride. Such buffer can be a phosphate or tris-hydrochloride buffer with pH adjusted to the vicinity of neutrality. Preferably, a 20 mN phosphate buffer (pH 7.4) and a 20 mN tris-hydrochloride buffer (pH 7.4) are taken.

The salt concentration of the salt-containing solution as an eluting solution varies with the final polypeptide, but at least 0.15 M is acceptable, and 0.18 M to 0.5 M is preferable. With the salt concentration of 0.18 M to 0.5 M, the final polypeptide is obtained at high purity. However, when it is higher than 0.5 M, impurities tend to be eluted though in small amounts.

Thus, according to the aforesaid purifying and recovering method, the pyrogen-free high-purity polypeptide can be afforded by simple means, and the resulting polypeptide is available as an active ingredient of an antitumor pharmaceutical composition.

Embodiments to work this invention will be described in more detail below.

(A) Cloning of human TNF gene

Human TNF gene can be obtained by selecting several codons specifying the amino acids (D. Pennica et al. cited above) constituting the human TNF protein, and chemically synthesizing the human TNF protein. In designing the human TNF gene, it is desired to select codons most suited for a host cell used, and to provide sites of cleavage with suitable restriction endonucleases so as to permit easy coloning and gene modification later. Preferably, a DNA region encoding the human TNF protein has a translation initiation codon (ATG) with the reading frame coinciding with its upstream, and a translation termination codon (TGA, TAG or TAA) with the reading frame coinciding with its downstream. Preferably in order to increase the expression efficiency, two or more translation termination codons are linked in tandem. Furthermore, by using cleavage sites of endonucleases acting on its upstream and downstream sides, this human TNF gene can be cloned into a suitable vector. An example of the base sequence of this human TNF gene is shown in FIG. 1.

Desirably, the human TNF gene designed as above is produced by dividing it into a plurality of oligonucleotides as shown in FIG. 2 with respect to each of the upper and lower chains, chemically synthesizing these oligonucleotides, and then linking them with each other. Synthesis methods for the individual oligonucleotides include, for example, the diester method (H. G. Khorana, "Some Recent Developments in Chemistry of Phosphate Esters of Biological Interest", John Wiley and Sons, Inc., New York (1961)), the triester method (R. L. Letsinger et al., J. Am. Chem. Soc., 89, 4801 (1967)) and the phosphite method (M. D. Matteucci et al., Tetrahedron Lett., 21, 7190 (1980)). Synthesis by the phosphite method using an entirely automated DNA synthesizing machine is preferred from the view point of the synthesizing time, the yield and the simplicity of the operation. The synthesized oligonucleotides may be purified by, for example, gel filtration, ion exchange chromatography, gel electrophoresis, and high-performance liquid chromatography on a reverse-phase column.

The hydroxyl groups of the 5'-teminus of the synthesized oligonucleotides are phosphorylated with T4-tripolynucleotide kinase, for example. Then, the oligonucleotides are annealed, and linked with T4-DNA ligase, for example. To synthesize the human TNF gene by linking the synthetic oligonucleotides, it is preferred to divide the oligonucleotides into some blocks, linking them in each block, clone the linked oligonucleotide blocks into a vector such as pBR322, and then linking the DNA fragments in these blocks. pTNF1BR, pTNF2N and pTNF3 are preferably used as plasmids containing the DNA fragment blocks constituting the human TNF gene.

After the cloned DNA fragments in the blocks constituting the human TNF gene are linked, the ligated DNA fragments may be joined to the downstream end of the promoter SD sequence to produce an expression gene. Usable promoters are, for example, trp promoter, lac promoter, trp promoter, $P_L$ promoter and lpp promoter. The trp promoter is especially preferred. Preferred plasmids having trp promoter are pYS31N and pAA41. To increase the efficiency of expression, a terminater which functions efficiently in E. coli can be attached downstream of the human TNF gene. Examples of the terminater are an lpp gene terminater and a trp gene terminater. The trp A terminater is especially preferred. Preferably, pAA41 is used as a plasmid having the trp A terminater. By cloning this human TNF gene into a vector derived, for example, from pBR322, an expression plasmid can be prepared. Preferably, pTNF401NN and pTNF401A are used as a plasmid expressing the human TNF gene.

(B) Cloning of a novel polypeptide gene having antitumor activity

The resulting plasmid expressing the human TNF gene is digested with a suitable restriction endonuclease to remove a specific region of the human TNF gene and then by using synthetic oligonucleotides having the suitable base sequence, the gene is repaired. This technique permits preparation of an expression plasmid containing a DNA encoding a polypeptide resulting from replacing a particular amino acid in the human TNF protein by another amino acid, deleting it, or adding another amino acid. Preferred plasmids expressing the novel antitumorally active polypeptide gene are the 13 types of plasmids described above.

(C) Determination of the expression and evaluation of the activity

E. coli, B. subtilis and yeasts are, for example, used as microorganism hosts for expressing the human TNF gene and the intended polypeptide genes. E. coli is especially preferred. The above plasmid expressing the human TNF gene and the plasmid expressing the novel antitumorally active polypeptide can be introduced into microorganism hosts such as E. coli C600r-m- strain (ATCC 33525) by a known method (M. V. Norgard et al., Gene, 3, 279 (1978)).

The resulting recombinant microorganism cells are cultivated by methods known per se. M9 medium containing glucose and casamino acids may, for example, be used as the culture medium [see T. Maniatis, et al., "Molecular Cloning", p.440, Cold Spring Harbor Laboratory, New York (1982)]. As required, ampicillin, for example, is desirably added. The cultivation is carried out under conditions suitable for the recombinant microorganism, for example, with aeration and stirring at 37° C. for 2 to 36 hours. At the start of, or during, the cultivation, a chemical such as 3-beta-indoleacrylic acid may be added in order to cause the promoter to function efficiently.

After the cultivation, the recombinant microorganism cells are harvested by, for example, centrifugal separation, and suspended in, for example, a phosphate buffer, and subjected to, for example, sonication to rupture the recombinant microorganism cells. Subsequent centrifugal separation gives a lysate of the recombinant microorganism cells. The protein in the lysate is separated by electrophoresis using a polyacrylamide gel containing sodium lauryl sulfate (SDS for short), and the protein in the gel is stained by a suitable method. By comparing the electrophoretic patterns using the lysate of the microorganism cells not containing the expression plasmid as a control, the expression of the human TNF gene or the novel antitumorally active polypeptide gene is determined.

The antitumor activities of the resulting human TNF protein and novel antitumorally active polypeptide are evaluated by, for example the in vivo activity measuring method by which the effect of necrotizing Meth A sarcoma transplanted in a mouse is examined (Carswell et al., cited hereinabove), or the in vitro activity measuring method by which cytotoxicity on mouse L cells is examined (Ruff, J., Immunol., 126, 235 (1981)). The in vitro activity measuring method is especially advantageous in the aspect of simplicity.

The separation and purification of the human TNF protein and the novel antitumorally active polypeptide from the E. coli lysates may be carried out in accordance with usually known protein separation and purification methods. Affinity column chromatography using antibody to the human TNF protein is available. An example is affinity column chromatography using a mouse monoclonal antibody to the human TNF protein.

Since the pyrogen-free high-purity polypeptide of this invention can easily be obtained also by the above purifying and recovering method using the cation exchange resin, the aforesaid purifying and recovering method in this invention is desirable.

The in vitro antitumor activity (as cited earlier) can directly be calculated by using the human TNF protein and antitumorally active polypeptide purified products obtained by the abovementioned methods.

Thus, in accordance with this invention, the antitumorally active polypeptide different from the known human TNF protein can be obtained, and the pharmaceutical composition having excellent antitumor activity can be provided using this antitumorally active polypeptide.

(D) Preparation of a pharmaceutical composition

The polypeptides obtained as above in this invention are much higher in antitumor activity than the human TNF, and some have low side effects, especially low toxicity; they are therefore used as an antitumor agent. The pharmaceutical composition for this may be one containing the polypeptide of formula (I) in this invention as an active ingredient and a pharmaceutically acceptable carrier.

When the pharmaceutical composition is prepared, the polypeptide used as the active ingredient can be modified too with a known polymer such as polyethylene glycol (PEG), dextran or poly-DL-alanine in order to reduce antigenicity of the polypeptide or enhance physiological activity thereof.

The pharmaceutical composition takes a form of an injection composition or a suppository. As the injection composition, an intravenous injection composition is especially preferable.

The injection composition is a mixture of a pharmaceutically acceptable amount of the polypeptide of formula (I) and a pharmaceutically acceptable carrier and can also contain an excipient which is commonly added to the injection composition, such as amino acids, carbohydrates, cellulose derivatives, polyvinyl pyrrolidone and inorganic compounds. Examples of the amino acids are glycine, alginine, alanine and their pharmaceutically acceptable salts. Examples of the carbohydrates are manitol, inositol, xylitol, lactol and glucose. Examples of the cellulose derivatives are sodium carboxymethylcellulose and methyl cellulose. An example of the polyvinyl pyrrolidone is polyvinyl pyrrolidone having a molecular weight of 10,000 to 1,000,000.

Examples of the organic acids are ascorbic acid, citric acid and their salts. Examples of the inorganic compounds are sodium hydrogenphosphate, sodium hydrogencarbonate and sodium acetate.

Examples of a solution that dissolves these excipients are distilled water, physiological saline and Ringer's solution for injection.

The injection solution may contain, as required, a stabilizer, a surface active agent, an isotonating agent, a soothing agent, an antiseptic and a buffer. Concrete examples thereof are antioxidants such as sodium pyrosulfite and -ascorbic acid, and chelating agents such as EDTA and thioglycol as the stabilizer; nonionic surface active agents such as polysolbate and polyoxyethylene derivatives as the surface active agent; sodium chloride as the isotonating agent; benzyl alcohol, xylocaine and procaine as the soothing agent; parabens, chlorobutanol, benzalconium chloride and thimerosal as the antiseptic; and sodium salts of citric acid, nitric acid and phosphoric acid as the buffer.

BRIEF DESCRIPTION OF THE ACCOMPANYING DRAWINGS

FIG. 1 shows the base sequence of a designed human TNF gene;

FIG. 2 shows the base sequences of chemically synthesized oligonucleotides;

Figure 3:
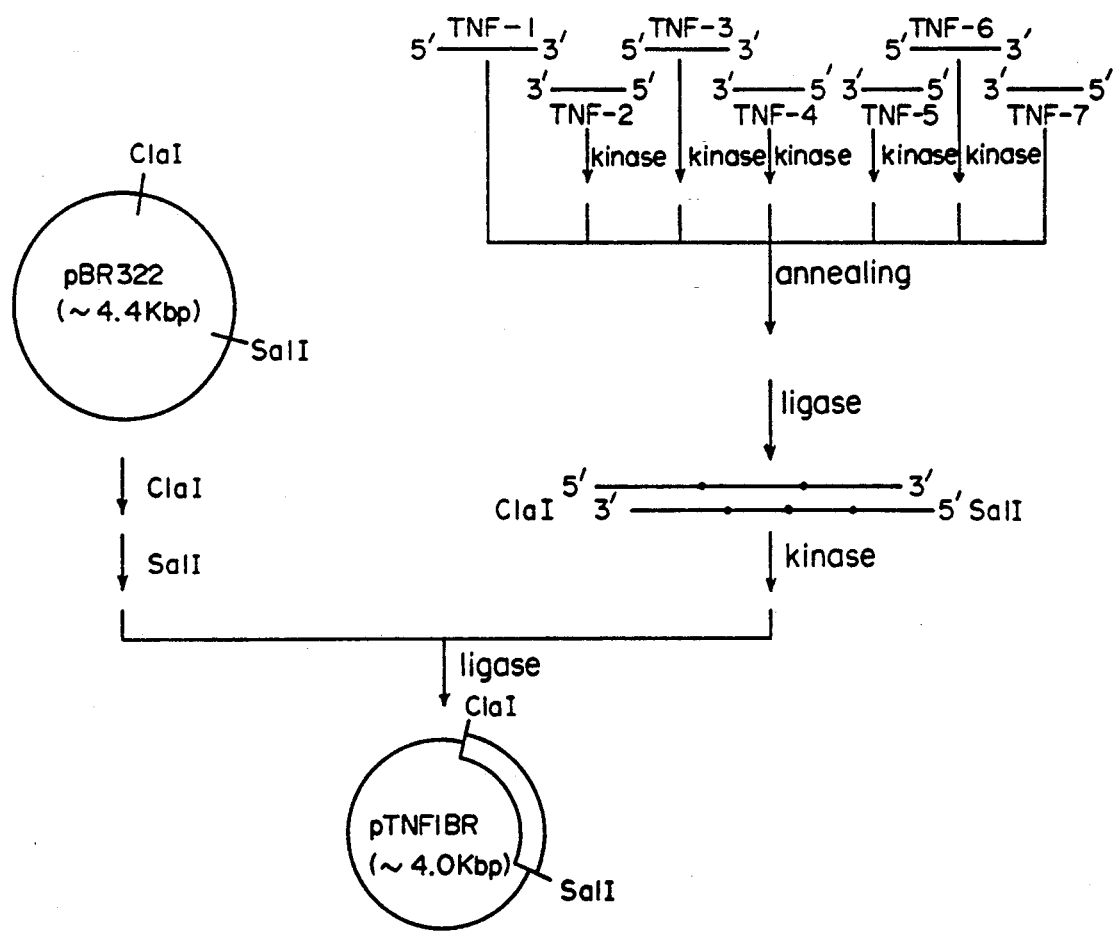
Figure 4:
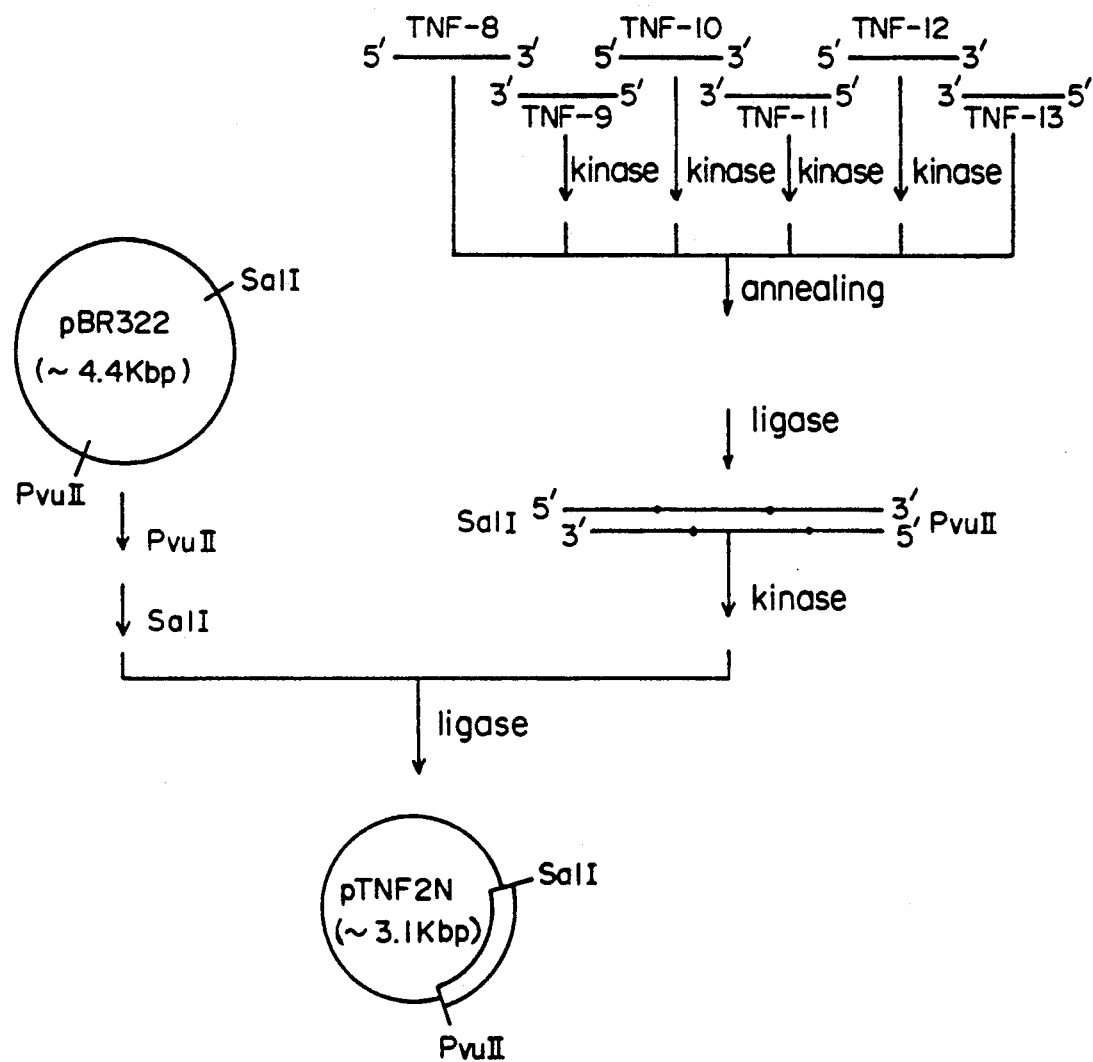
Figure 5:
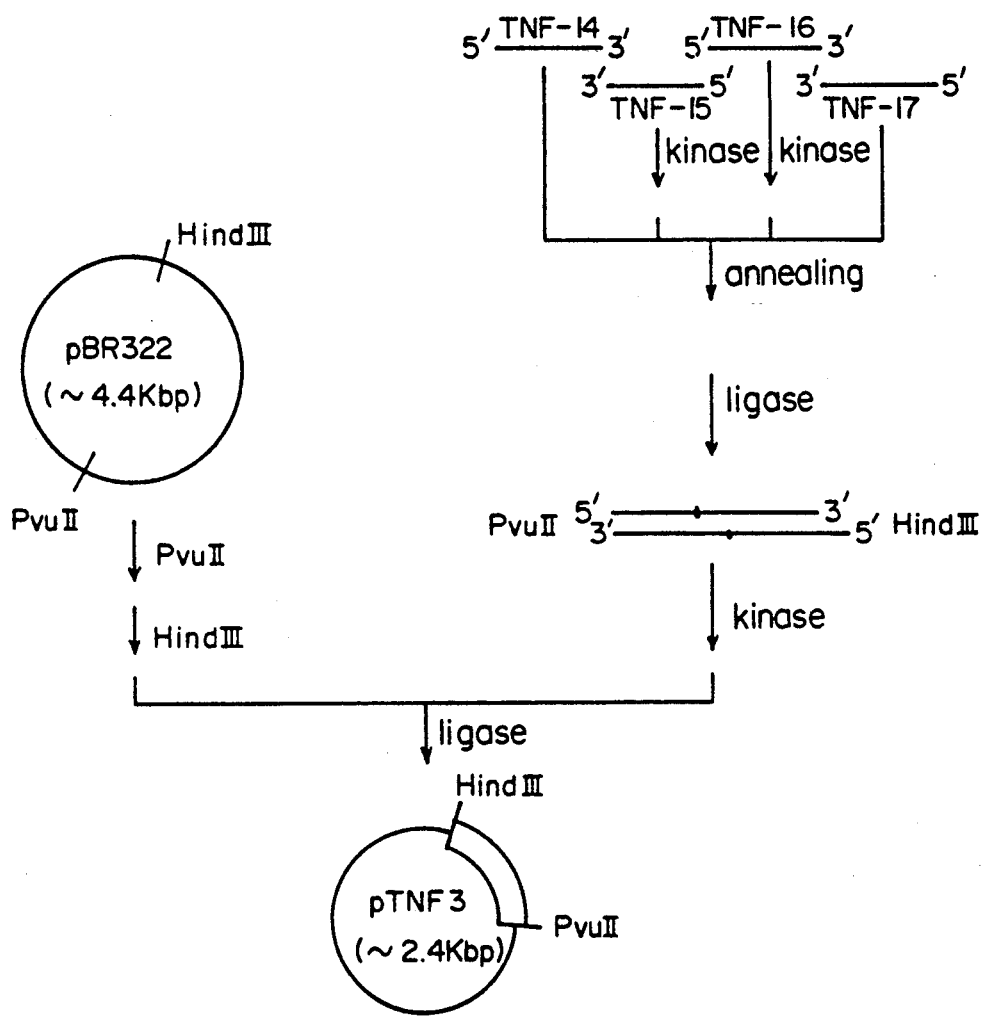
Figure 6:
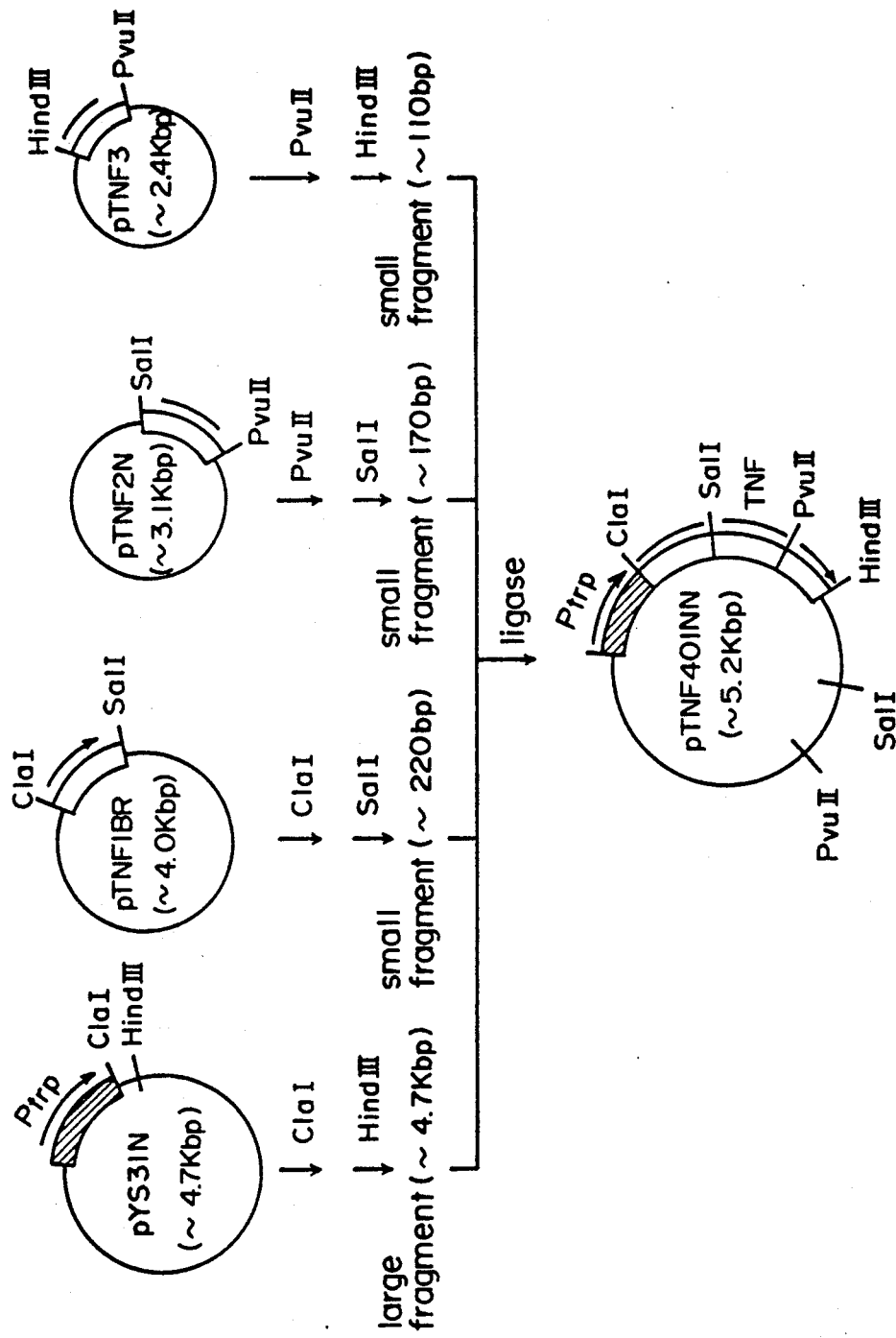
Figure 11:
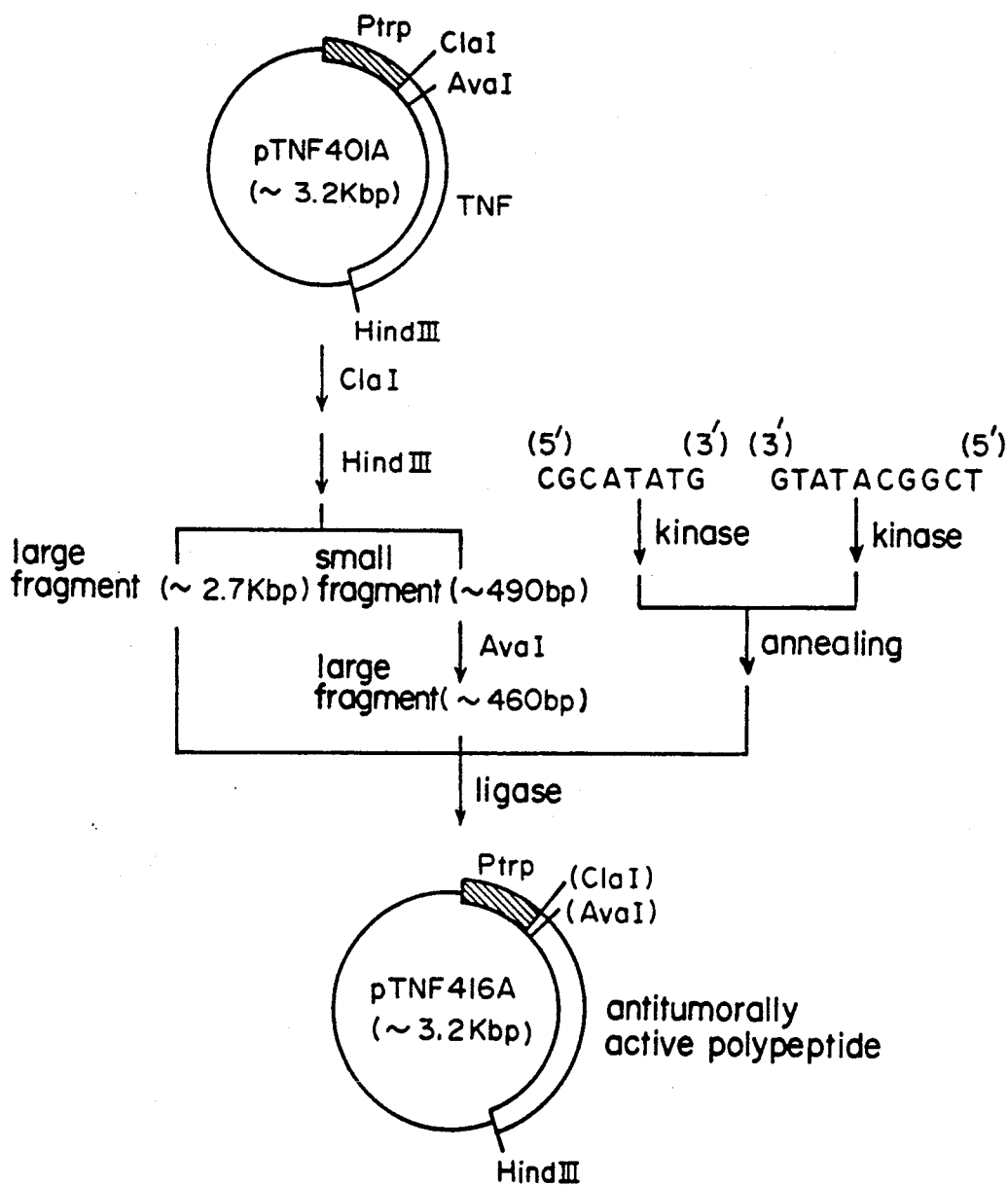
Figure 20:
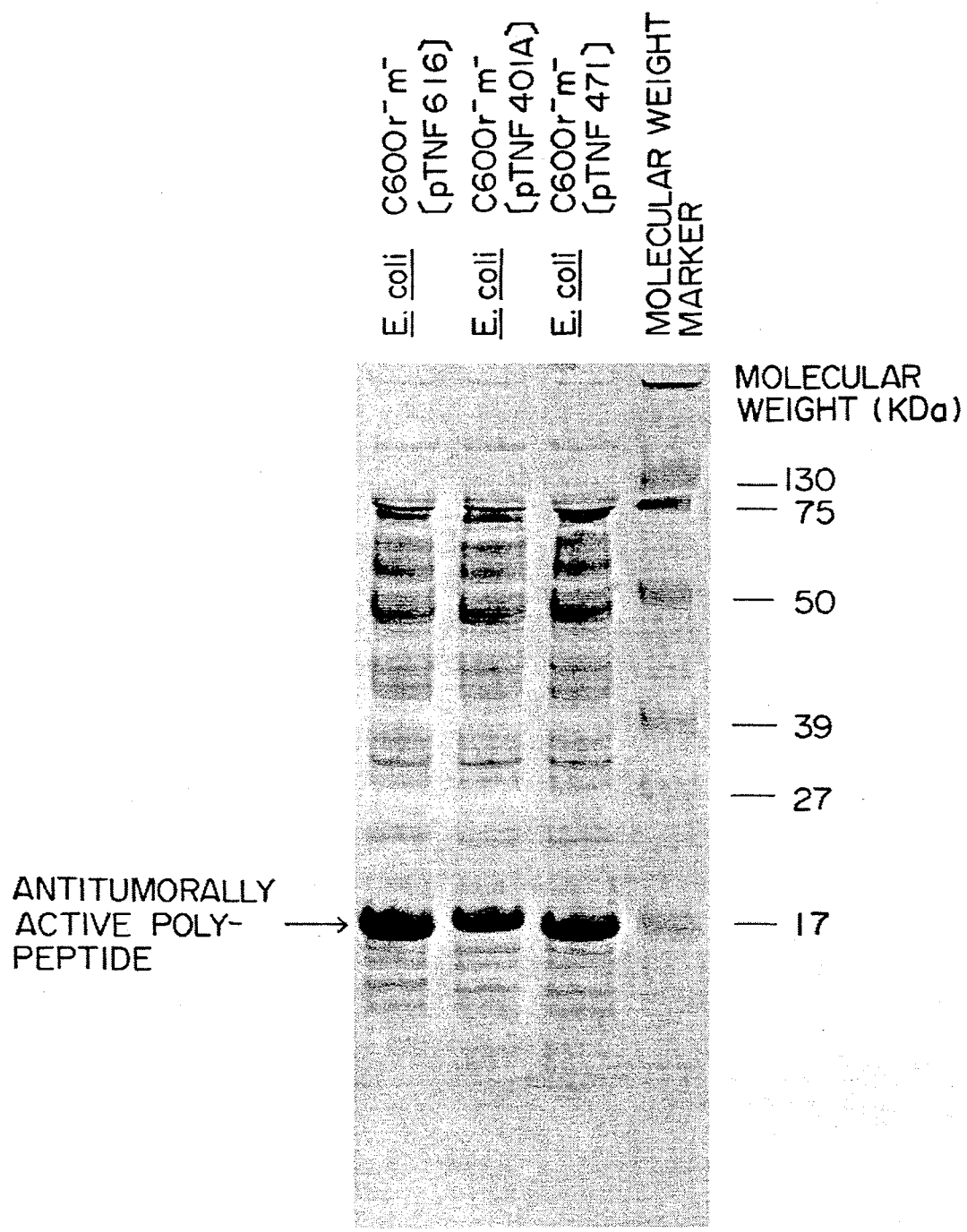
Figure 21:
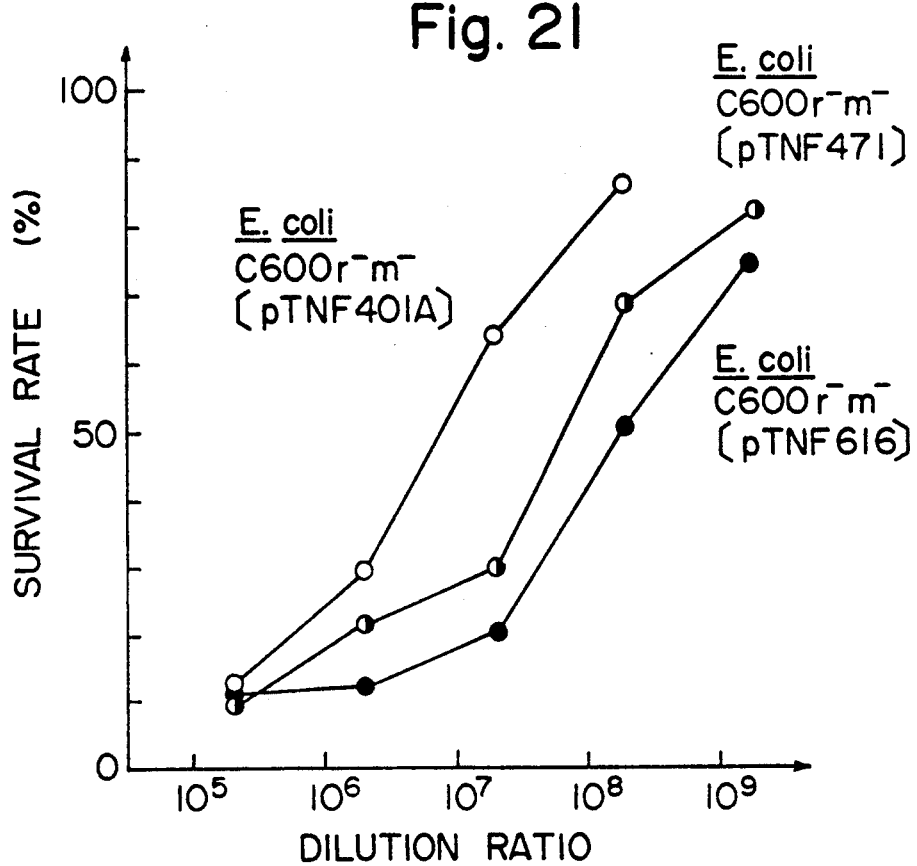
Figure 22:
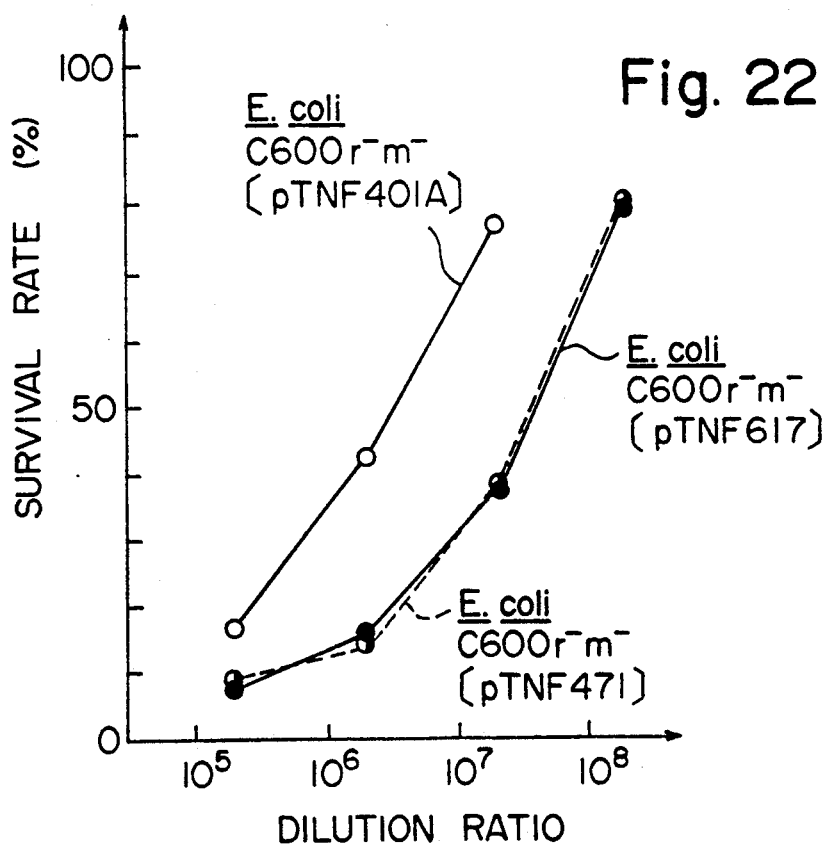
Figure 23:
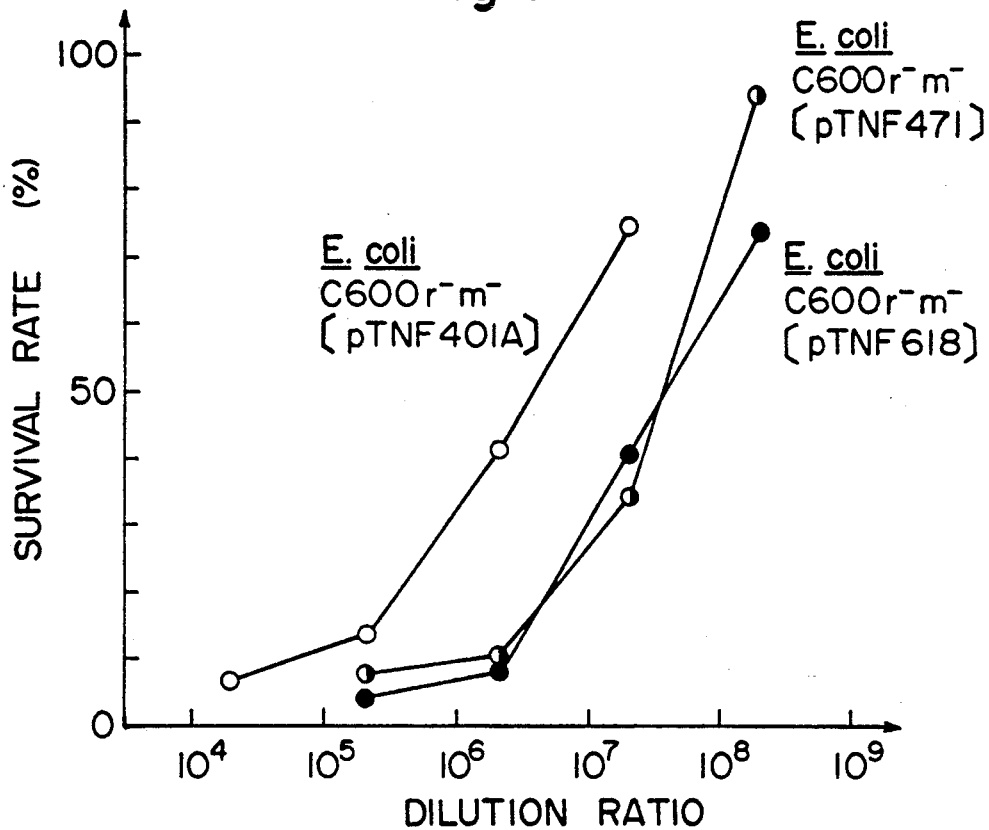
Figure 24:
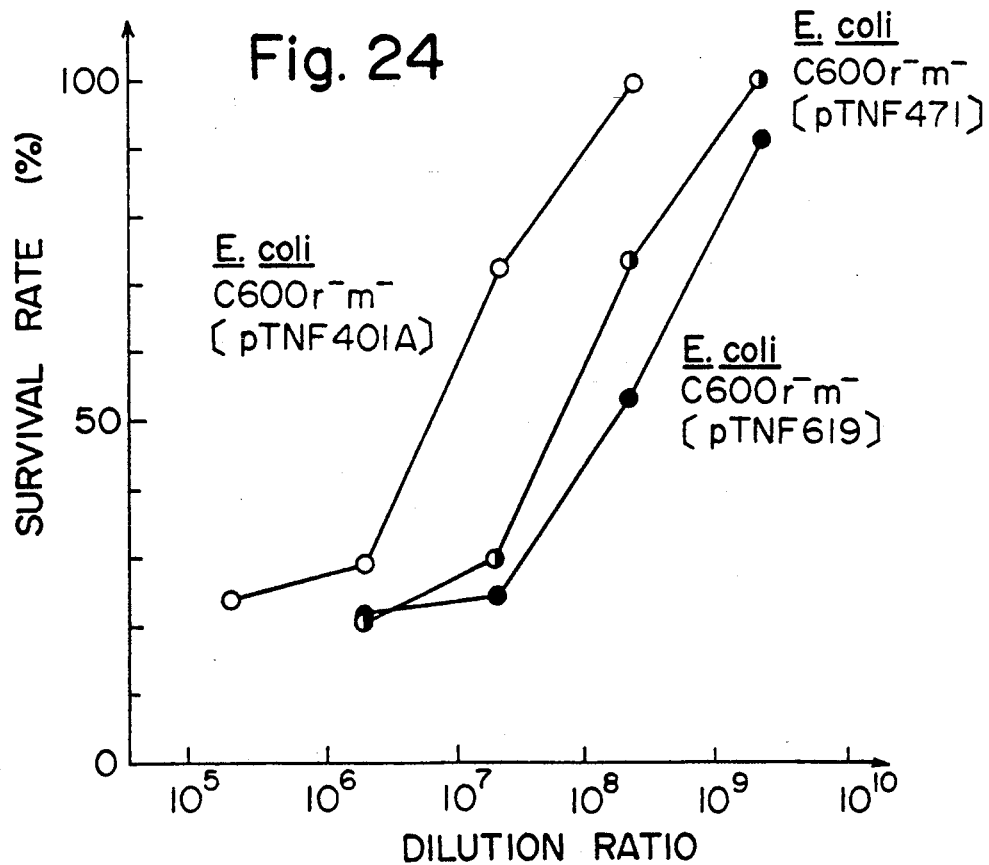
Figure 25:
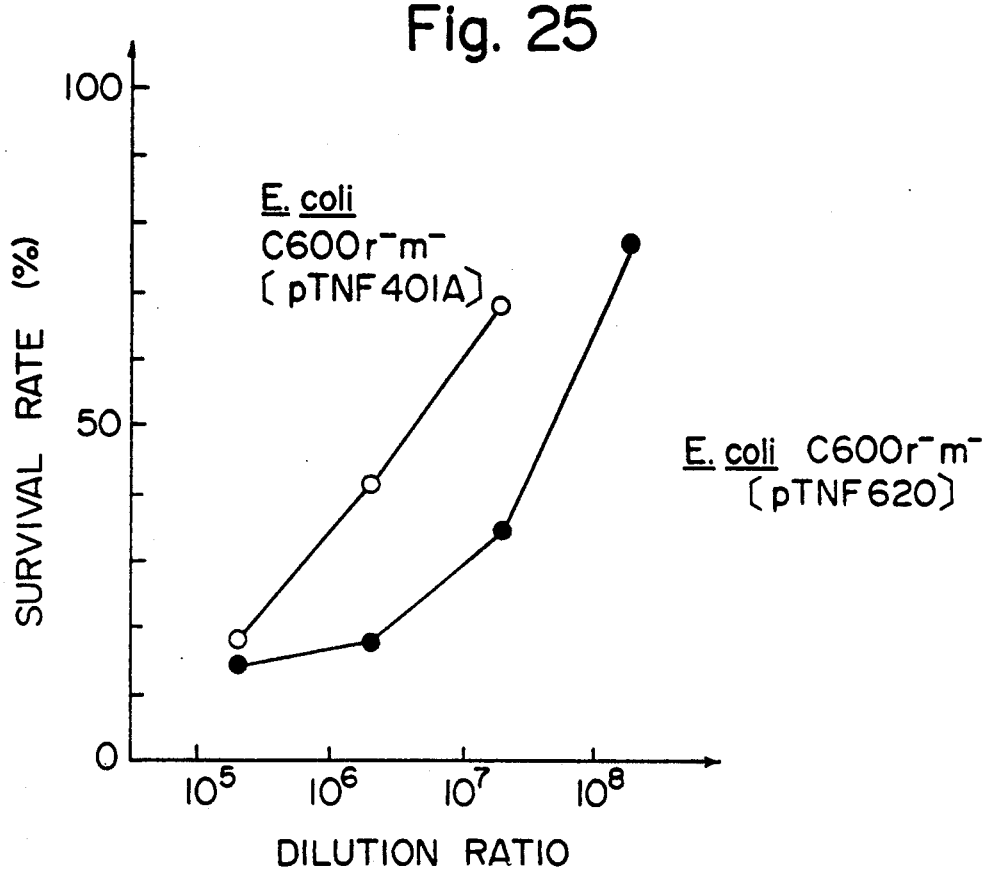
Figure 26:
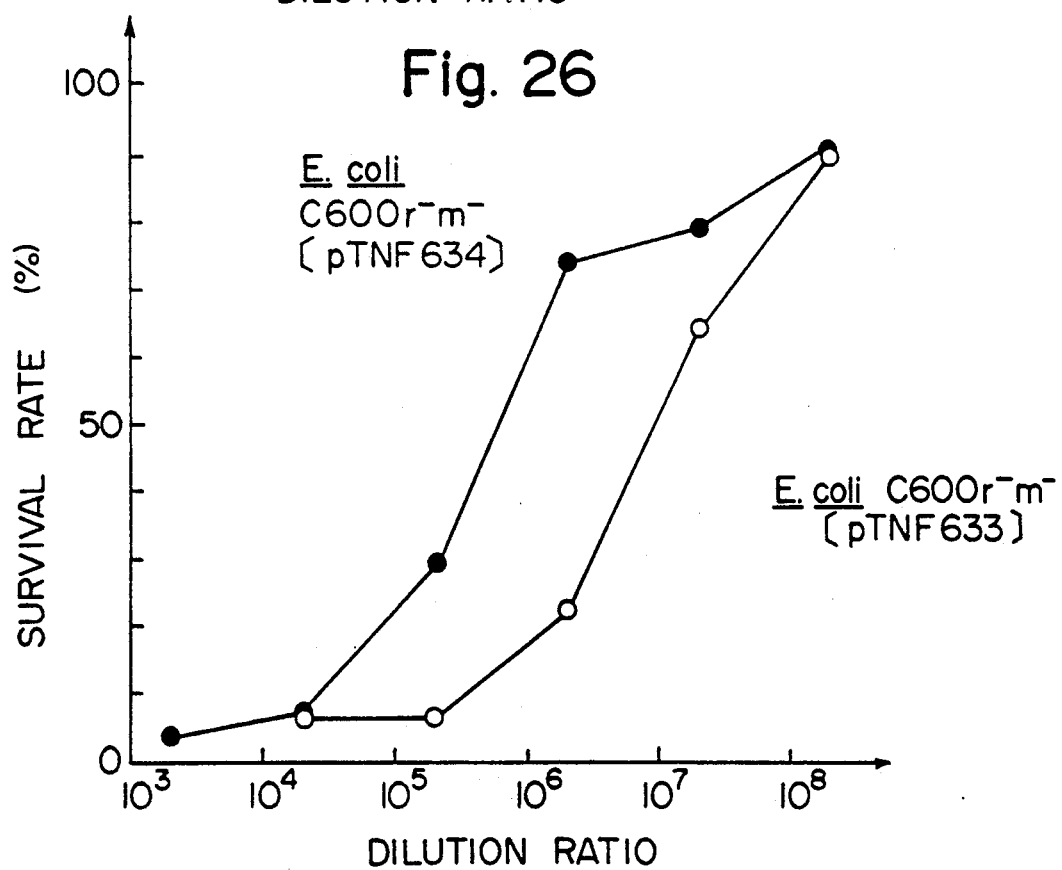
Figure 27:
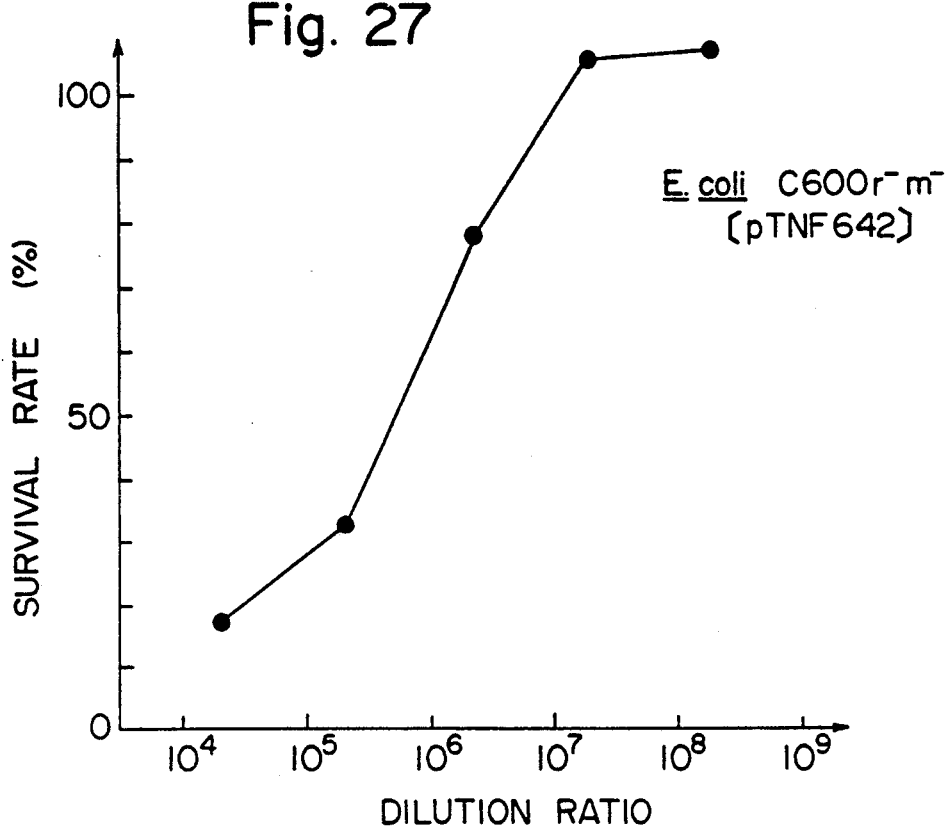
Figure 28:
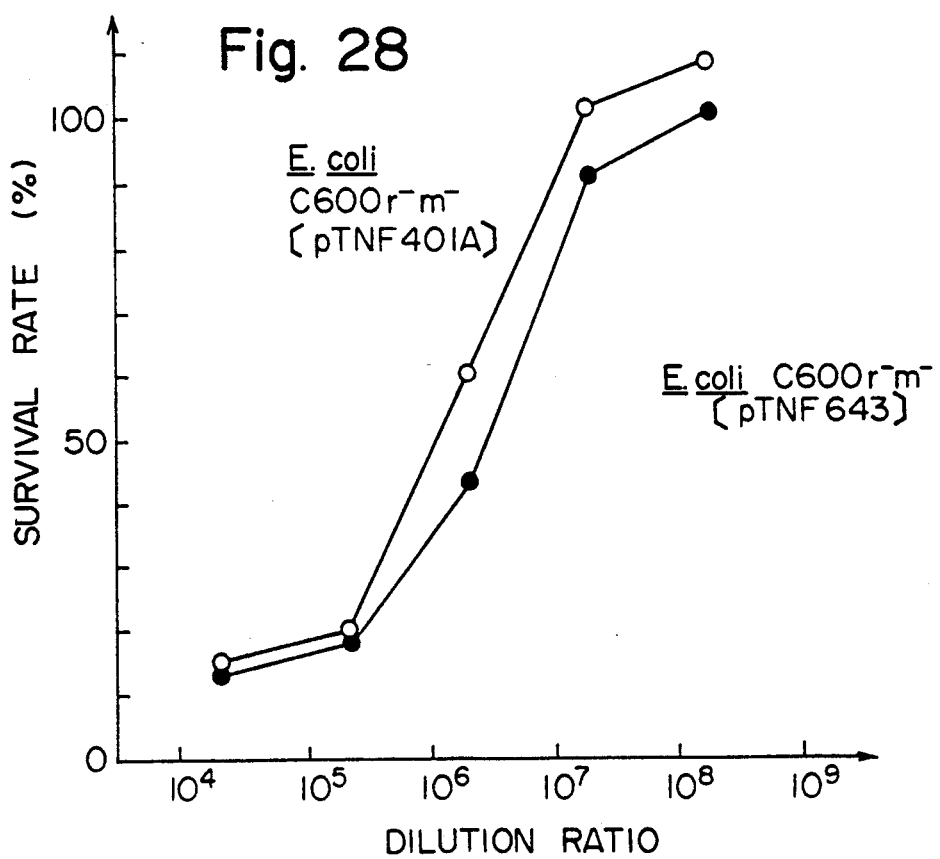
Figure 29:
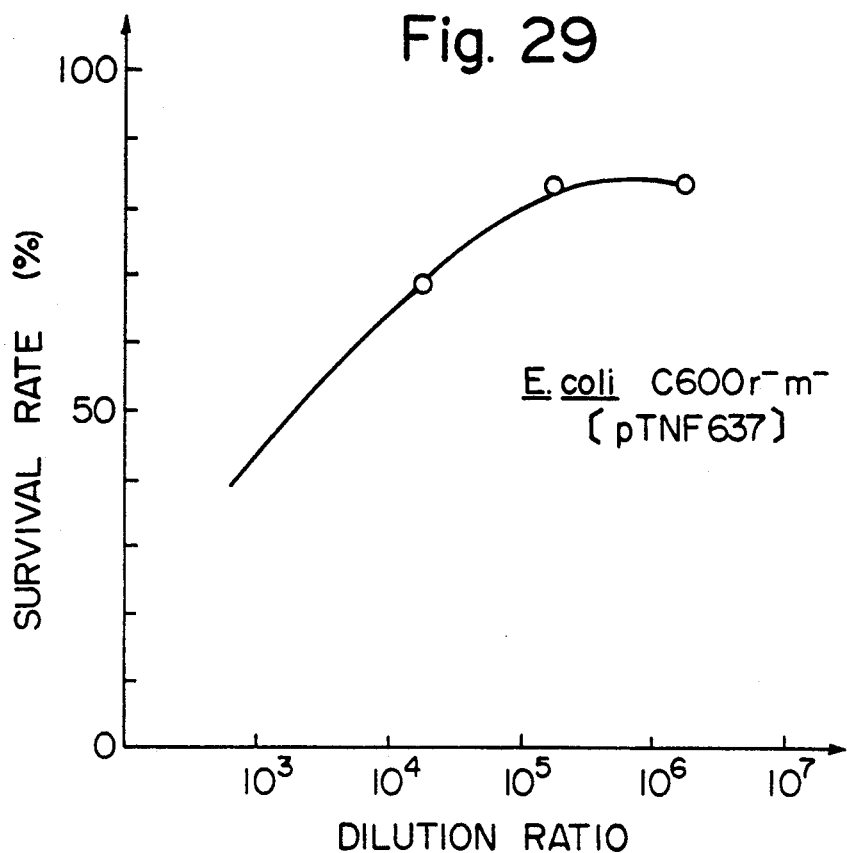
Figure 30:
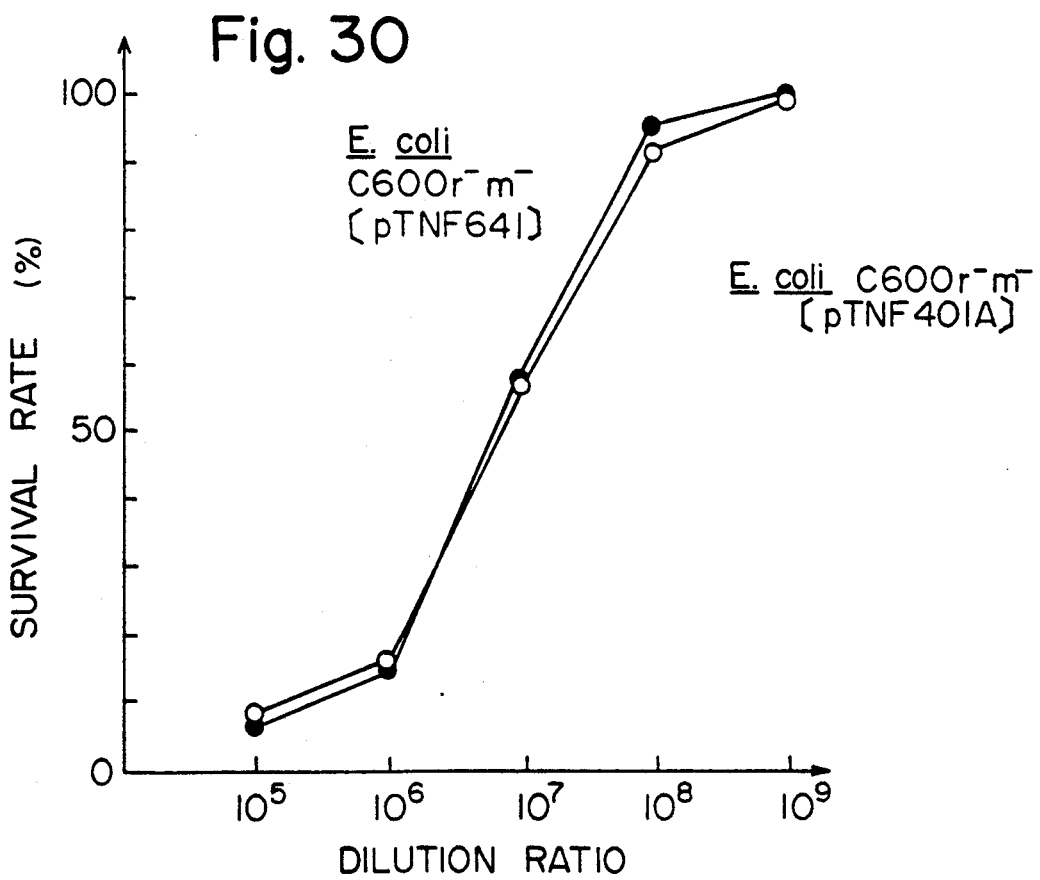
Figure 31:
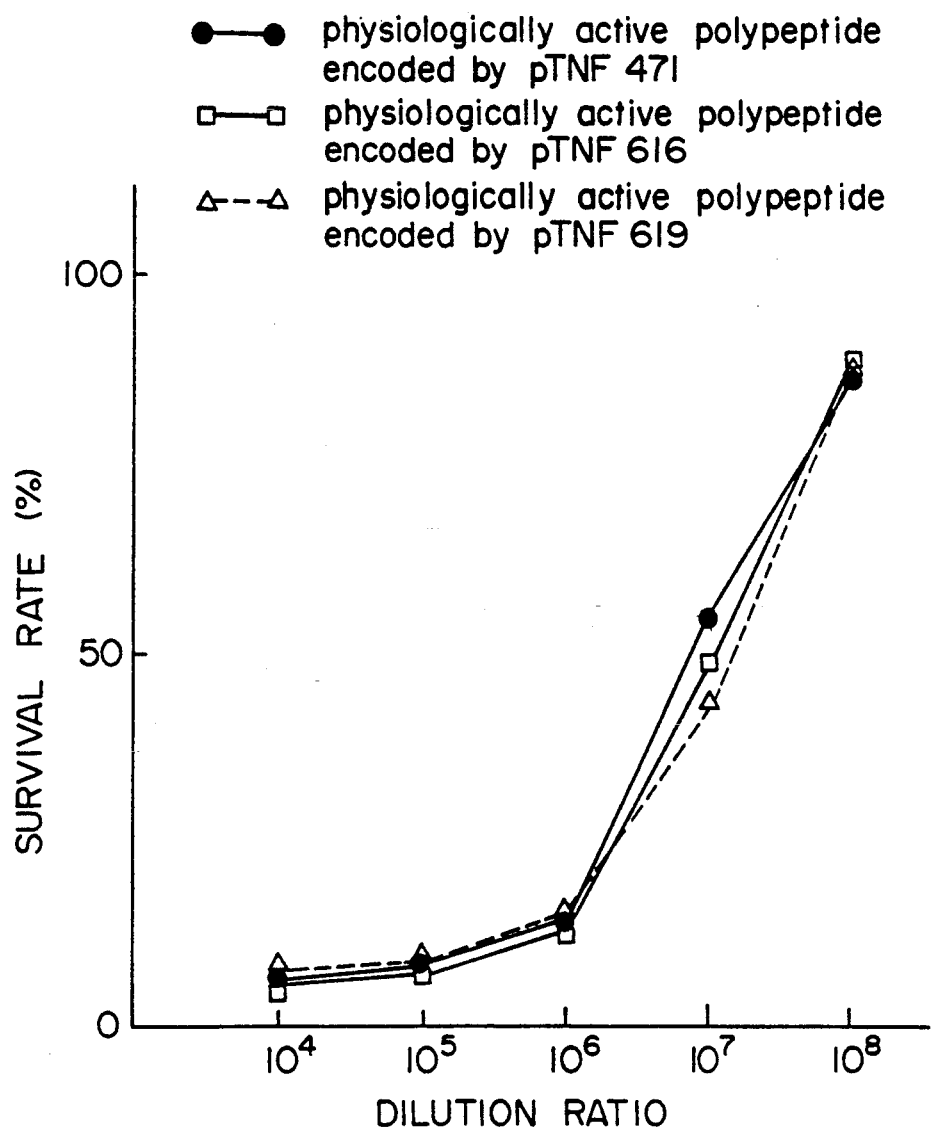

FIGS. 3, 4 and 5 respectively show methods of preparing plasmids pTNF1BR, pTNF2N and pTNF3 having part of human TNF gene;

FIG. 6 shows a method of preparing plasmid pTNF401NN capable of expressing the human TNF gene;

FIG. 7-B shows a method of preparing a plasmid pAA41 using the oligonucleotide of FIG. 7-A;

FIG. 8 shows a method of preparing a plasmid pTNF401A capable of expressing the human TNF gene;

FIG. 9A and 9B show a method of preparing a plasmid pTNF471 capable of expressing the antitumorally active polypeptide gene;

FIGS. 10A(1), 10-A(2), and 10-B show a method of preparing plasmids capable of expressing the antitumorally active polypeptide genes, pTNF616, pTNF617, pTNF618, pTNF619, pTNF620, pTNF633, pTNF634, pTNF642 and pTNF643;

FIG. 11 shows a method of preparing pTNF416A;

FIGS. 12A and 12B and 13 show a method of preparing pTNF621 to pTNF627;

FIGS. 14-A(1), 14-A(2), 14A-(3), and 14-B show a method of preparing pTNF628 to pTNF632;

FIGS. 15-A, 15-B, 16-A and 16-B show a method of preparing pTNF637;

FIGS. 17-A, 17-B, 18, 19-A and 19-B show a method of preparing pTNF641;

FIG. 20 shows the results of expression of pTNF616;

FIG. 21 shows the results of measuring the in vitro antitumor activity of the antitumorally active polypeptide encoded by pTNF616;

FIG. 22 shows the results of measuring the in vitro antitumor activity of the antitumorally active polypeptide encoded by pTNF617;

FIG. 23 shows the results of measuring the in vitro antitumor activity of the antitumorally active polypeptide encoded by pTNF618;

FIG. 24 shows the results of measuring the in vitro antitumor activity of the antitumorally active polypeptide encoded by pTNF619;

FIG. 25 shows the results of measuring the in vitro antitumor activity of the antitumorally active polypeptide encoded by pTNF620;

FIG. 26 shows the results of measuring the in vitro antitumor activity of the antitumorally active polypeptide encoded by pTNF633 and pTNF634;

FIG. 27 shows the results of measuring the in vitro antitumor activity of the antitumorally active polypeptide encoded by pTNF642;

FIG. 28 shows the results of measuring the in vitro antitumor activity of the antitumorally active polypeptide encoded by pTNF643;

FIG. 29 shows the results of measuring the in vitro antitumor activity of the antitumorally active polypeptide encoded by pTNF637;

FIG. 30 shows the results of measuring the in vitro antitumor activity of the antitumorally active polypeptide encoded by pTNF641;

FIG. 31 shows the in vitro antitumor activity of the purified polypeptide obtained in Example 9.

The following examples illustrate the present invention in greater detail. It should be understood however that the invention is not limited to these examples.

EXAMPLE 1

Designing of a human TNF gene

A human TNF gene having the base sequence shown in FIG. 1 was designed. The base sequence of the structural gene portion of the human TNF precursor cDNA reported by Pennica et al. (D. Pennica et al. Nature, 312, 724 (1984)) was used as a basis. A cleavage site by a suitable restriction endonuclease was provided at a suitable position. A translation initiation codon (ATG) was attached to the 5'-side and two translation termination codons (TGA and TAA), to the 3'-side of the human TNF gene respectively. A cleavage site by restriction endonuclease ClaI was provided upstream of the 5'-side translation initiation codon to maintain a proper distance between the translation initiation codon and the SD sequence in a suitable condition to permit joining of a promoter. A site of cleavage with restriction endonuclease HindIII was provided downstream of the 3'-side termination codons to permit easy joining of a vector plasmid.

EXAMPLE 2

Chemical synthesis of oligonucleotides

The human TNF gene designed in Example 1 was divided into 17 oligonucleotides as shown in FIG. 2. These oligonucleotides were synthesized by the phosphite method using an entirely automated DNA synthesizer (Model 380A made by Applied Biosystems). The synthesized oligonucleotides were purified in accordance with the Manual of Applied Biosystems, Inc.

Specifically, an aqueous ammonia solution containing the synthetic oligonucleotides was maintained overnight at 55° C. to remove the protective groups of the DNA bases, and by gel filtration using a Sephadex G-50 fine gel (Pharmacia), high-molecular-weight synthetic oligonucleotide fractions were recovered. The oligonucleotide fractions were electrophoresed on a polyacrylamide gel containing 7M urea (gel concentration 20 %), and the electrophoretic patterns were observed by the ultraviolet shadowing method. Bands having the desired size were cut out. The polyacrylamide gel fragments were crushed finely, and 2 to 5 ml of a dissolving buffer (500 mM NH$_4$OAc - 1 mM EDTA—0.1% SDS (pH 7.5)) was added. The mixture was shaken overnight at 37° C. The aqueous layer containing the desired DNA was recovered by centrifugal separation. Finally, the solution containing the synthetic oligonucleotides was charged onto a gel filtration column (Sephadex G-50) to give purified products of the synthetic oligonucleotides. As required, the polyacrylamide gel electrophoresis was repeated to increase the purity of the synthetic oligonucleotides.

EXAMPLE 3

Cloning of chemically synthesized human TNF gene

Using the 17 synthetic oligonucleotides (TNF-1 to TNF-17) prepared in Example 2, the human TNF gene was divided into three blocks and cloned.

The 5'-terminus of 0.1 to 1.0 microgram of each of the synthetic oligonucleotides TNF-2 to TNF-6 was phosphorylated with 5 to 15 units of T4-polynucleotide kinase (E. coli B type, produced by Takara Shuzo Co., Ltd.). The phosphorylation reaction was carried out in 10 to 20 microliters of an aqueous solution of 50 mM Tris-HCl (pH 9.5), 10 mM MgCl$_2$, 5 mM dithiothreitol and 10 mM ATP at 37° C. for 30 minutes. After the reaction, all aqueous solutions of synthetic oligonucleotides were mixed, and extracted with phenol and ether to deactivate and remove T4-polynucleotide kinase. Newly, 0.1 to 1.0 microgram of synthetic oligonucleotides TNF-1 and TNF-7 were added to the synthetic oligonucleotide mixture obtained. The mixture was heated to 90° C. and then gradually cooled to room temperature to perform annealing. The mixture was dried under reduced pressure and dissolved in 30 microliters of an aqueous solution of 66 mM Tris-HCl (pH 7.6), 6.6 mM MgCl$_2$, 10 mM dithiothreitol and 1 mM ATP, and 300 units of T4-DNA ligase (a product of Takara Shuzo) was added. The ligating reaction was carried out at 11° C. for 15 hours. After the reaction, the reaction mixture was electrophoresed on a polyacrylamide gel (gel concentration 5%), and the electrophoretic patterns were observed by the ethidium bromide staining method. Bands having the desired size (about 220 bp) were cut out, and by the method of Example 2, DNA was recovered from the polyacrylamide gel.

In the meantime, 3 micrograms of plasmid pBR 322 (about 4.4 kbp) for E. coli was dissolved in 30 microliters of an aqueous solution containing 10 mM Tris-HCl (pH 7.5), 60 mM NaCl and 7 mM MgCl$_2$. Ten units of restriction endonuclease ClaI (a product of New England Bio-Rad) was added, and the digestion reaction was carried out at 30° C. for 1 hour. After the digestion, the reaction mixture was extracted with phenol and then ether, and precipitated from ethanol to recover DNA. The DNA was dissolved in 30 microliters of an aqueous solution containing 50 mM Tris-HCl (pH 7.4), 100 mM NaCl and 10 mM MgSO$_4$, 10 units of restriction enzyme SalI (a product of Takara Shuzo) was added, and the digestion reaction was carried out at 37° C. for 1 hour. After the reaction, the reaction mixture was electrophoresed on an agarose gel (gel concentration 0.8%), and the cleavage patterns were observed by the ethidium bromide staining method. A band corresponding to a DNA portion having a size of 3.7 kbp and containing most of the plasmid pBR 322 was cut out, and the agarose gel slice was dissolved in 3 times its amount (vol/wet) of an 8M aqueous solution of NaClO$_4$. A DNA fragment (ClaI—SalI) having a size of about 3.7 kbp was recovered from the agarose gel by the glass filter method of Chen et al. (C. W. Chen et al. Anal, Biochem., 101, 3339 (1980)).

The terminals of the DNA fragment having a size of about 220 bp and containing part of the human TNF gene, which has been obtained previously, was phosphorylated in accordance with the method described hereinabove, and the product was mixed with an aqueous solution of DNA having a size of about 3.7 kbp and containing most of the plasmid pBR 322. After precipitation from ethanol, the two DNA fragments were ligated by the method described above.

Transformation of E. coli C600r-m- strain was carried out by an improved method of the ordinary CaCl$_2$ method (the method of M. V. Norgard et al.). Specifically, a culture medium in which E. coli C600r-m- strain had been cultivated for 18 hours was inoculated in 5 ml of L medium (1% tryptone, 0.5% yeast extract, 0.5% NaCl, pH 7.2), and grown until the turbidity at 600 nm (OD$_{600}$) of the culture liquid containing the cells reached 0.3. The cells were washed twice in a cold magnesium buffer (0.1 M NaCl, 5 mM MgCl$_2$, 5 mM Tris-HCl (pH 7.0, 0° C.)], re-suspended in 2 ml of a cold calcium buffer 100 mM CaCl$_2$, 250 mM KCl, 5 mM MgCl$_2$, 5 mM Tris-HCl (pH 7.6, 0° C.)], and left to stand at 0° C. for 25 minutes. The cells were concentrated to 1/10 of this volume in the calcium buffer, and mixed with the aqueous DNA solution after the ligation in a ratio of 2:1 (vol:vol). The mixture was maintained at 0° C. for 60 minutes, 1 ml of LBG medium (1% tryptone, 0.5% yeast extract, 1% NaCl, 0.08% glucose, pH 7.2) was then added, and the resulting mixture was cultivated with shaking at 37° C. for 1 hour. The culture broth was inoculated in selective media (L-basal plates containing 30 micrograms/ml of ampicillin (Sigma)) at a rate of 100 microliters/plate. The plates were cultivated at 30° C. overnight to grow the transformants. DNA was prepared from the resulting ampicillin-resistant colonies by a known method. By agarose gel electrophoresis, the production of the desired plasmid pTNF1BR (about 4.0 kbp) was determined. FIG. 3 shows the method of preparing the plasmid pTNF1BR.

By the same procedure as above, plasmid pTNF2N (about 3.1 kbp) was prepared by using synthetic oligonucleotides TNF-8 to TNF-13, and plasmid pTNF3 (about 2.4 kbp) by using synthetic oligonucleotides TNF-14 to TNF-17. FIGS. 4 and 5 show methods of preparing the plasmids pTNF2N and pTNF3.

It was determined by the method of Maxam and Gilbert (A. M. Maxam et al.: Methods in Enzymol., 65, 499 (1980)) that the synthetic oligonucleotide portions of the plasmids pTNF1BR, pTNF2N and pTNF3 containing part of the human TNF gene obtained as above had the base sequences exactly as designed.

EXAMPLE 4

Preparation of a plasmid capable of expressing the human TNF gene

Ten micrograms of the plasmid pTNF1BR obtained in Example 3 was digested with restriction endonucleases ClaI and SalI as in Example 3. The digestion product was electrophoresed on a polyacrylamide gel (gel concentration 5%). Then, in accordance with the method of Example 2, a DNA fragment (ClaI - SalI) having a size of about 220 bp and containing part of the human TNF gene was recovered from the polyacrylamide gel.

Then, 10 micrograms of the plasmid pTNF2 obtained in Example 3 was dissolved in 10 microliters of an aqueous solution containing 10 mM Tris-HCl (pH 7.5), 60 mM NaCl, and 7 mM $MgCl_2$, and 40 units of restriction endonuclease PvuII (a product of Takara Shuzo) was added. The digestion reaction was carried out at 37° C. for 1 hour. Then, in accordance with the method of Example 3, digestion with restriction endonuclease SalI and polyacrylamide gel electrophoresis (gel concentration 5%) were carried out. Thereafter, in accordance with the method of Example 2, a DNA fragment (SalI - PvuII) having a size of about 170 bp and containing part of the human TNF gene was recovered from the polyacrylamide gel.

Ten micrograms of the plasmid pTNF3 obtained in Example 3 was dissolved in 100 microliters of an aqueous solution containing 10 mM Tris-HCl (pH 7.5), 60 mM NaCl, and 7 mM $MgCl_2$, and 40 units of restriction endonuclease PvuII and 40 units of restriction endonuclease HindIII (a product of Takara Shuzo) were added, and the digestion reaction was carried out at 37° C. for 1 hour. After polyacrylamide gel electrophoresis (gel concentration 5%), a DNA fragment (PvuII - HindIII) having a size of about 110 bp and containing part of the human TNF gene was recovered from the polyacrylamide gel in accordance with the method of Example 2.

On the other hand, 5 micrograms of the plasmid pYS31N (about 4.7 kbp) containing *E. coli* trp promoter was digested as above with restriction endonucleases ClaI and HindIII. After agarose gel electrophoresis (gel concentration 0.8%), a DNA fragment (ClaI - HindIII) having a size of about 4.7 kbp and containing most of the plasmid pYS31N was recovered from the agarose gel.

The resulting three DNA fragments having a size of about 220 bp, about 170 bp and about 110 bp and containing part of the human TNF gene which were obtained as above were mixed with the DNA fragment (about 4.7 kbp) containing most of the plasmid pYS31N. After precipitation with ethanol, the mixture was subjected to ligating reaction with T4-DNA ligase. After the reaction, in accordance with the method of Example 3, the ligation product was introduced into *E. coli* C600r-m- strain, and from the transformants, clones having the desired plasmid pTNF401NN (about 6.2 kbp) capable of expressing the human TNF gene were selected. FIG. 6 shows a method of preparing the plasmid pTNF401NN.

Five micrograms of the plasmid pYS31N was partially digested with restriction endonuclease PvuII and then digested with restriction endonuclease HindIII. The digestion product was electrophoresed on an agarose gel (gel concentration 0.8%), and in accordance with the method of Example 3, a DNA fragment (PvuII (2) - HindIII) having a size of about 2.7 kbp and containing trp promoter was recovered from the agarose gel.

Oligonucleotides having the base sequence shown in FIG. 7-A were synthesized and purified in accordance with the method of Example 2. The terminal of 0.5 microgram of each of the resulting two synthetic oligonucleotides was phosphorylated in accordance with the method of Example 3. After annealing, the synthetic oligonucleotides were mixed with the DNA fragment (PvuII (2) - HindIII) having a size of about 2.7 kbp obtained previously. After precipitation with ethanol, the mixture was subjected to a ligation reaction with T4-DNA ligase. After the reaction, the ligation product was introduced into *E. coli* C600r-m- strain in accordance with the method of Example 3. Clones having the desired plasmid pAA41 (about 2.7 kbp) were selected from the transformants. This plasmid is a high copy high efficient expression vector resulting from removing the copy number control region from the plasmid pYS31N and joining *E. coli* trp A terminater to the downstream of the cloning site existing downstream of trp promoter. The method of its preparation is shown in FIG. 7-B.

Two micrograms of the plasmid pAA41 was digested with restriction endonucleases ClaI and HindIII in the same way as above, and after agarose gel electrophoresis (gel concentration 0.8%), a DNA fragment (ClaI - HindIII) having a size of about 2.7 kbp and containing most of the pAA41 was recovered from the agarose gel.

Furthermore, 5 micrograms of the plasmid pTNF401NN capable of expressing the human TNF gene, which had been obtained as above, was digested with restriction endonucleases ClaI and HindIII in the same way as above. After polyacrylamide gel electrophoresis (gel concentration 5%), a DNA fragment (ClaI - HindIII) having a size of about 490 bp and containing the entire region of the human TNF gene was recovered from the polyacrylamide gel in accordance with the method of Example 2.

The DNA fragment (about 2.7 kbp) containing most of the plasmid pAA41 and the DNA fragment (about 490 bp) containing the entire region of the human TNF gene obtained above were mixed, and after precipitation with ethanol, subjected to a ligating reaction with T4-DNA ligase in accordance with the method of Example 3. After the reaction, the ligation product was introduced into *E. coli* C600r-m- strain, clones having the desired plasmid pTNF401A (about 3.2 kbp) were selected from the transformants, in accordance with the method of Example 3. This plasmid has the ability to express the human TNF gene with good efficiency, and FIG. 8 shows a method of its preparation.

EXAMPLE 5

Preparation of a plasmid capable of expressing the antitumorally active polypeptide Twenty micrograms of the plasmid pTNF401A capable of expressing the human TNF gene obtained in Example 4 was digested with restriction endonucleases ClaI and HindIII in accordance with the method of Example 4. The digestion product was subjected to polyacrylamide gel electrophoresis (gel concentration 5%) and agarose gel electrophoresis (gel concentration 0.8%). The resulting two DNA fragments (about 490 bp and about 2.7 kbp; both ClaI - HindIII) were recovered from the gels.

The DNA fragment (about 490 bp) containing the entire region of the human TNF gene was dissolved in 50 microliters of an aqueous solution containing 10 mM Tris-HCl (pH 7.4), 10 mM $MgSO_4$ and 1 mM dithiothreitol, and 10 units of restriction endonuclease HapII (a product of Takara Shuzo) was added. The digestion reaction was carried out at 37° C. for 1 hour. After the reaction, the reaction mixture was electrophoresed on a polyacrylamide gel (gel concentration 5%), and in accordance with the method of Example 2, a DNA fragment (HapII - HindIII) having a size of about 390 bp and containing most of the human TNF gene was recovered from the polyacrylamide gel.

Oligonucleotides having the base sequences shown in FIG. 9 were synthesized and purified in accordance with the method of Example 2. The terminals of the resulting four synthetic oligonucleotides in an amount of 0.5 microgram each were phosphorylated by the method of of Example 3, and after annealing, they were ligated by using T4-DNA ligase.

After the reaction, the resulting doublestranded oligonucleotide was mixed with the DNA fragment (ClaI - HindIII) having a size of about 2.7 kbp and the DNA fragment (HapII - HindIII) having a size of about 390 bp which were obtained above, and after precipitation with ethanol, the mixture was subjected to ligation with T4-DNA ligase in accordance with the method of Example 3. After the reaction, the ligation product was introduced into E. coli C600r-m- strain in accordance with the method of Example 3, and clones having the desired plasmid pTNF471 (about 3.2 kbp) were selected from the transformants. This plasmid is a plasmid encoding the antitumorally active polypeptide having the following amino acid sequence

[NH₂]-Arg-Lys-Arg-X-Ile-Ile-Ala-Leu-[COOH]-
(SEQ ID NO. 14)

wherein X is as defined above, or a plasmid with Met bound to the amino-terminus (SEQ ID NO. 28). The method of its preparation is shown in FIG. 9.

Meanwhile, 20 micrograms of the above obtained human TNF gene expressing plasmid pTNF471 was digested with restriction endonuclease HindIII in accordance with the method of Example 4. Subsequently, the digestion product was subjected to a digestion reaction with restriction endonuclease NcoI (a product of Takara Shuzo) in an aqueous solution containing 50 mM Tris-HCl (pH 7.4), 100 mM NaCl and 10 mM $MgSo_4$ at 37° C. for 1 hour. After the reaction, the resulting digestion product was subjected to agarose gel electrophoresis (gel concentration 0.7%) and polyacrylamide gel electrophoresis (gel concentration 5%). According to the method in Example 2, the DNA fragment (NcoI - HindIII) having a size of about 140 bp and containing part of the human TNF gene was recovered from the polyacrylamide gel. According to the method in Example 3, about 3.0 kbp of the DNA fragment (NcoI - HindIII) containing most of pTNF471 was recovered from the agarose gel.

Moreover, the above obtained DNA fragment (NcoI - HindIII) having a size of about 140 bp was dissolved in 50 microliters of an aqueous solution containing 10 mM of Tris-HCl (pH 7.4), 10 mM $MgSO_4$ and 1 mM dithiothreitol, and 10 units of restriction endonuclease AccI (a product of Takara Shuzo) was added. The digestion reaction was conducted at 37° C. for 1 hour. After the reaction, polyacrylamide gel electrophoresis (gel concentration 8%) was carried out. In accordance with the method in Example 2, a DNA fragment (NcoI - AccI) having a size of about 110 bp and containing part of the human TNF gene was recovered from the polyacrylamide gel.

Oligonucleotide having the base sequence No. 616 shown in FIG. 10A was synthesized and purified according to the method in Example 2. The terminals of the resulting two synthetic oligonucleotides in an amount of 0.5 microgram each were phosphorylated by the method in Example 3, followed by annealing.

After the annealing, the resulting double-stranded fragment (NcoI - HindIII) was mixed with the DNA fragment (NcoI - HindIII) having a size of about 3.0 kbp and and DNA fragment (NcoI - AccI) having a size of about 110 bp and containing part of the human TNF gene, which were obtained above. After the mixture was precipitated with ethanol, the ligation reaction with T4-DNA ligase was run by the method of Example 3. After the reaction, the resulting product was introduced into E. coli C600r-m- strain in accordance with the method of Example 3, clones having the desired plasmid pTNF616 (about 3.2 kbp) were selected from the transformants. This plasmid is a plasmid capable of expressing an antitumorally active polypeptide gene encoding an antitumorally active polypeptide having the following amino acid sequence (H₂N)-Arg-Lys-Arg-X-Ile-Ile-Ala-Phe-(COOH
SEQ ID NO. 5))

wherein X is as defined above, or a polypeptide with Met bound to the amino-terminus (SEQ ID NO. 5). A method of preparing same is shown in FIG. 10 B.

In the above method, oligonucleotides having the following base sequences shown in FIG. 10 A were used instead of the base sequence No. 616 shown in FIG. 10 A. Plasmids of corresponding numbers were obtained:

| Base sequence No. | Plasmid | Amino acid sequence of polypeptide encoded by plasmid |
| --- | --- | --- |
| No. 617 | pTNF617 | (H₂N)—(Met)$_n$—Arg—Lys—Arg—X—Ile—Ile—Ala—Trp—(COOH) (SEQ ID NOS. 6 and 20) |
| No. 618 | pTNF618 | (H₂N)—(Met)$_n$—Arg—Lys—Arg—X—Ile—Ile—Trp—Leu—(COOH) (SEQ ID NOS. 8 and 22) |
| No. 619 | pTNF619 | (H₂N)—(Met)$_n$—Arg—Lys—Arg—X—Ile—Ile—Phe—Leu—(COOH) (SEQ ID NOS. 9 and 23) |
| No. 620 | pTNF620 | (H₂N)—(Met)$_n$—Arg—Lys—Arg—X—Ile—Ile—Ala—Leu—Phe—(COOH) (SEQ ID NOS. 7 and 21) |
| No. 633 | pTNF633 | (H₂N)—(Met)$_n$—Arg—Lys—Arg—X—Ile—Ile—Phe—Phe—(COOH) (SEQ ID NOS. 10 and 24) |

| Base sequence No. | Plasmid | Amino acid sequence of polypeptide encoded by plasmid |
|---|---|---|
| No. 634 | pTNF634 | $(H_2N)$—$(Met)_n$—Arg—Lys—Arg—X—Ile—Ile—Trp—Phe—(COOH) (SEQ ID NOS. 11 and 25) |
| No. 642 | pTNF642 | $(H_2N)$—$(Met)_n$—Arg—Lys—Arg—X—Phe—Ile—Ala—Leu—(COOH) (SEQ ID NOS. 13 and 27) |
| No. 643 | pTNF643 | $(H_2N)$—$(Met)_n$—Arg—Lys—Arg—X—Ile—Phe—Ala—Leu—(COOH) (SEQ ID NOS. 12 and 26) | wherein n and X are as defined above.

Preparation of pTNF621 to pTNF632

Twenty micrograms of the plasmid pTNF401A capable of expressing the human TNF gene obtained in Example 4 was digested with restriction endonucleases ClaI and HindIII in accordance with the method of Example 4. The digestion product was subjected to polyacrylamide gel electrophoresis (gel concentration 5%) and agarose gel electrophoresis (gel concentration 0.8%). In accordance with the methods of Examples 2 and 3, the resulting two DNA fragments (about 490 bp and about 2.7 kbp, ClaI - HindIII in both cases) were recovered from the gels.

The DNA fragment having a size of about 490 bp and containing the entire region of the human TNF gene was dissolved in 50 microliters of an aqueous solution containing 10 mM of Tris-HCl (pH 7.5), 60 mM of NaCl and 7 mM of $MgCl_2$, and 10 units of restriction endonuclease AvaI (a product of Takara Shuzo) was added. The digestion reaction was conducted at 37° C. for 1 hour. After the reaction, polyacrylamide gel electrophoresis (gel concentration 5%) was carried out, and a DNA fragment (AvaI - HindIII) having a size of about 460 bp and containing most of the human TNF gene was recovered from the polyacrylamide gel in accordance with the method of Example 2.

In accordance with the method of Example 2, the double-stranded oligonucleotide having the base sequence shown in FIG. 11 was synthesized by dividing it into the upper and lower strands, and purified. The terminals of the resulting four synthetic oligonucleotides in an amount of 0.5 microgram each were phosphorylated by the method of Example 3, followed by annealing.

After the annealing, the double-stranded oligonucleotide was mixed with the DNA fragment (ClaI - HindIII) having a size of about 2.7 kbp and the DNA fragment (AvaII - HindIII) having a size of about 460 bp and containing most of the human TNF gene, which were obtained above. After the mixture was precipitated with ethanol, the ligation reaction with T4-DNA ligase was carried out in accordance with the method of Example 3. After the reaction, the ligation product was introduced into E. coli C600r-m- strain in accordance with the method of Example 3. Clones having the desired plasmid pTNF416A (about 3.2 kbp) were selected from the transformants. This plasmid is a plasmid capable of expressing the antitumorally active polypeptide gene encoding the antitumorally active polypeptide with No. 7 amino acid in the amino-terminus of TNF deleted. A method of preparing same is shown in FIG. 11.

Meanwhile, 20 micrograms of the above obtained expression plasmid pTNF 416A was digested with restriction endonuclease HindIII in accordance with the method of Example 4. The digestion reaction with restriction endonuclease NcoI (a product of Takara Shuzo) was run at 37° C. for 1 hour in an aqueous solution of 50 mM Tris-HCl (pH 7.4), 100 mN NaCl, 10 mM $MgSO_4$. After the reaction, agarose gel electrophoresis (gel concentration 0.7%) and polyacrylamide gel electrophoresis (gel concentration 5% were conducted. A DNA fragment (NcoI - AccI) having a size of about 140 bp and containing part of the human TNF gene was recovered from the polyacrylamide gel in accordance with the method of Example 2, and a DNA fragment (NcoI - HindIII) having a size of about 3.0 kbp and containing most of pTNF416A was recovered from the agarose gel in accordance with the method of Example 3.

Moreover, the above DNA fragment (NcoI - HindIII) having a size of about 140 bp was dissolved in 50 microliters of an aqueous solution containing 10 mM Tris-HCl (pH 7.4), 10 mM $MgSO_4$ and 1 mM dithiothreitol, and 10 units of restriction endonuclease AccI (a product of Takara Shuzo) was added. The digestion reaction was run at 37° C. for 1 hour. After the reaction, polyacrylamide gel electrophoresis (gel concentration 8%) was carried out. In accordance with the method of Example 2, a DNA fragment (NcoI - AccI) having a size of about 110 bp and containing part of the human TNF gene was recovered from the polyacrylamide gel.

In accordance with the method of Example 2, oleonucleotide having the base sequence shown in FIG. 12 was synthesized and purified. The terminals of the resulting two synthetic oleonucleotides in an amount of 0.5 microgram was phosphorylated by the method of Example 3, and followed by annealing.

After the annealing, the resulting double-stranded oleonucleotide was mixed with the DNA fragment (NcoI - HindIII) having a size of about 3.0 kbp and the DNA fragment (NcoI - AccI) having a size of about 110 kbp and containing part of the human TNF gene which were obtained above. After precipitation with ethanol, the ligation reaction with T4-DNA ligase was run in accordance with the method of Example 3. After the reaction, the ligation product was introduced into E. coli C600r-m-strain. Clones having the desired plasmid pTNF621 (about 3.2 kbp) were selected from the transformants. The plasmid is a plasmid capable of expressing an antitumorally active poly peptide gene encoding an antitumorally active polypeptide having the following amino acid sequence

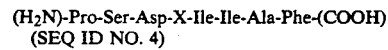
(SEQ ID NO. 4)

or a polypeptide with Met bound to the amino-terminus (SEQ ID NO. 18). A method of preparing same is shown in FIG. 12.

Using synthetic DNA's (Nos. 622 to 627) shown in FIG. 13 instead of the synthetic DNA having the base sequence shown in FIG. 11, there was prepared a plasmid containing a DNA region encoding diluted TNF having such a sequence that amino acid residue No. 1, 2, 3, 4, 5 or 6 at the amino-terminus in the amino acid sequence from No. 1 Val to No. 157 Leu shown in FIG. 1 was diluted. On the other hand, in accordance with the method shown in FIG. 14, there was prepared a plasmid containing a DNA region encoding diluted TNF having such a sequence that amino acid residue No. 8, 9, 10, 11 or 12 in the aminoterminus in the amino acid sequence from No. 1 Val to No. 157 Leu was diluted. Using the thus obtained plasmid of the DNA sequence encoding diluted TNF instead of the plasmid pTNF416A as a starting material in FIG. 12, there could be obtained the plasmid pTNF622, pTNF623, pTNF624, pTNF625, pTNF626, pTNF627, pTNF628, pTNF629, pTNF630, pTNF631 or pTNF632 containing a DNA region encoding a novel physiologically active polypeptide having such a sequence that in the amino acid sequence of from No. 1 Val to No. 157 Leu shown in FIG. 1, amino acid residue No. 1, 2, 3, 4, 5, 6, 8, 9, 10, 11 or 12 at the amino-terminus was diluted and No. 157 Leu was replaced with Phe, or a polypeptide with Met bound to the amino-terminus.

Preparation of pTNF637

In accordance with the method of Example 3, the above obtained expression plasmid pTNF416A was digested with restriction endonucleases EcoRI and SalI. After the digestion product was subjected to polyacrylamide gel electrophoresis (gel concentration 5%) and agarose gel electrophoresis (gel concentration 0.8%), the resulting two DNA fragments (about 560 bp and about 2.6 kbp, SalI - EcoRI in both cases) were recovered from the gels in accordance with the methods of Examples 2 and 3.

The DNA fragment having a size of about 560 bp and containing half of a 5'-site of the antitumorally active polypeptide gene was dissolved in 50 microliters of an aqueous solution containing 10 mM Tris-HCl (pH 7.4), 10 mM $MgSO_4$ and 1 mM dithiothreitol, and 10 units of restriction endonuclease KpnI (a product of Takara Shuzo) was added. The digestion reaction was run at 37° C. for 1 hour. After the reaction, polyacrylamide gel electrophoresis (gel concentration 5%) was conducted, and a DNA fragment (EcoRI - KpnI) having a size of about 500 bp and containing a portion of the 5'-site of the antitumorally active polypeptide gene was recovered from the polyacrylamide gel in accordance with the method of Example 2.

In accordance with the method of Example 2, the oligonucreotide having the base sequence shown in FIG. 15 was synthesized and purified. The terminals of the resulting two synthetic oligonucreotides in an amount of 0.5 microgram each were phosphorylated by the method of Example 3. After annealing, the ligation reaction with T4-DNA ligase was carried out.

After the reaction, the resulting doublestranded oligonucleotide was mixed with the DNA fragment (SalI - EcoRI) having a size of about 2.6 kbp and the DNA fragment (EcoRI - KpnI) having a size of about 500 bp and containing a portion of the 5'-site of the antitumorally active polypeptide gene, which were obtained above. After precipitation with ethanol, the ligation reaction with T4-DNA ligase was conducted in accordance with the method of Example 3. After the reaction, the ligation product was introduced into E. coli C600r-m- strain in accordance with the method of Example 3. Clones having the intended plasmid pTNF611 (about 3.2 kbp) were selected from the transformants. This plasmid is an expression plasmid encoding an antitumorally active polypeptide having the following amino acid sequence ($H_2N$)-Pro-Ser-Asp-$X_{54}$-Ile-Ile-Ala-Leu-(COOH
(SEQ ID NO. 20))

wherein $X_{54}$ is a sequence in which No. 54 (number of the amino acid sequence in FIG. 1) Gly in the above defined X is replaced with Asp,
or a polypeptide with Met bound to the amino-terminus (SEQ. ID NO. 30). A method of preparing same is shown in FIG. 15.

Twenty micrograms of the resulting expression plasmid pTNF611 was digested with restriction endonuclease HindIII in accordance with the method of Example 4. The digestion reaction with restriction endonuclease NcoI (a product of Takara Shuzo) was carried out at 37° C. for 1 hour in an aqueous solution containing 50 mM Tris-HCl (pH 7.4), 100 mM NaCl and 10 mM of $MgSO_4$. After the reaction, agarose gel electrophoresis (gel concentration 0.7%) and polyacrylamide gel electrophoresis (gel concentration 5%) were carried out. A DNA fragment (NcoI - HindIII) having a size of about 140 bp and containing part of the human TNF gene was recovered from the polyacrylamide gel in accordance with the method of Example 2, and a DNA fragment (NcoI - HindIII) having a size of about 3.0 kbp and containing most of pTNF611 was recovered from the agarose gel in accordance with the method of Example 3.

Besides, the DNA fragment (NcoI - HindIII) having the size of about 140 bp was dissolved in 50 microliters of an aqueous solution containing 10 mM Tris-HCl (pH 7.4), 10 mM $MgSO_4$ and 1 mM dithiothreitol, and 10 units of restriction endonuclease AccI (a product of Takara Shuzo) was added. The digestion reaction was run at 37° C. for 1 hour. After the reaction, polyacrylamide gel electrophoresis (gel concentration 8%) was carried out. In accordance with the method of Example 2, a DNA fragment (NcoI - AccI) having a size of about 110 bp and containing part of the human TNF gene was recovered from the polyacrylamide gel.

In accordance with the method of Example 2, oligonucleotide having the base sequence shown in FIG. 16 was synthesized and purified. In accordance with the method of Example 3, the terminals of the resulting two synthetic oligonucleotides in an amount of 0.5 microgram each were phospholylated, followed by annealing.

After the annealing, the resulting double-stranded oligonucleotide was mixed with the DNA fragment (NcoI - HindIII) having a size of about 3.0 kbp and the DNA fragment (NcoI - AccI) having a size of about 110 bp and containing part of the human TNF gene. After precipitation with ethanol, the ligation reaction with T4-DNA ligase was run in accordance with the method of Example 3. After the reaction, the ligation product was introduced into E. coli C600r-m- strain in accordance with the method of Example 3. Clones having the intended plasmid pTNF637 (about 3.2 kbp) were selected from the transformants. This plasmid is a plasmid capable of expressing an antitumorally active polypeptide gene encoding an antitumorally active polypeptide having the following amino acid sequence ($H_2N$)-Pro-Ser-Asp-$X_{54}$-Ile-Ile-Ala-Phe-(COOH
(SEQ ID NO. 31)

wherein $X_{54}$ is as defined above, or a polypeptide with Met bound to the amino-terminus (SEQ ID NO. 32). A method of preparing same is shown in FIG. 16.

Preparation of pTNF641

Twenty micrograms of the plasmid pTNF401A capable of expressing the human TNF gene, which was obtained in Example 4, was dissolved in 100 microliters of an aqueous solution containing 10 mM Tris-HCl (pH 7.4), 10 mM MgSO₄ and 1 mM dithiothreitol, and 40 units of restriction endonuclease KpnI (a product of Takara Shuzo) was added. The digestion reaction was run at 37° C. for 1 hour. Further, digestion with restriction endonuclease ClaI was carried out in accordance with the method of Example 3. After polyacrylamide gel electrophoresis (gel concentration 5%) and agarose gel electrophoresis (gel concentration 0.8%), the resulting two DNA fragments (about 160 bp and about 3.0 kbp, ClaI - KpnI in both cases) were recovered from the gels in accordance with the methods of Examples 2 and 3.

The DNA fragment having a size of about 160 bp and containing the first half of the human TNF gene was dissolved in 50 microliters of an aqueous solution containing 10 mM Tris-HCl (pH 7.4), 10 mM MgSO₄ and 1 mM dithiothreitol, and 10 units of restriction endonuclease HapII (a product of Takara Shuzo) was added. The digestion reaction was run at 37° C. for 1 hour. After the reaction, polyacrylamide gel electrophoresis (gel concentration 5%) was carried out. In accordance with the method of Example 2, a DNA fragment (ClaI - HapII) having a size of about 100 bp and containing the first half of the human TNF gene was recovered from the polyacrylamide gel.

In accordance with the method of Example 2, oligonuclease having the base sequence shown in FIG. 17 was synthesized and purified. In accordance with the method of Example 3, the terminals of the resulting synthetic two oligonucleotides in an amount of 0.5 microgram each were phosphorylated, followed by annealing.

After the reaction, the resulting doublestranded oligonucleotide was mixed with the DNA fragment (ClaI - KpnI) having a size of about 3.0 kbp and the DNA fragment (ClaI-HapII) having a size of about 100 bp and containing the first half of the human TNF gene, which were obtained above. After precipitation with ethanol, the ligation reaction with T4-DNA ligase was run in accordance with the method of Example 3. After the reaction, the ligation product was introduced into *E. coli* C600r-m- strain in accordance with the method of Example 3. Clones having the intended plasmid pTNF489 (about 3.2 kpb) were selected from the transformants. This plasmid is a plasmid capable of expressing an antitumorally active polypeptide encoding an antitumorally active polypeptide having the following amino acid sequence

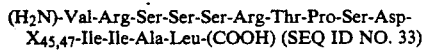
(H₂N)-Val-Arg-Ser-Ser-Ser-Arg-Thr-Pro-Ser-Asp-
X₄₅,₄₇-Ile-Ile-Ala-Leu-(COOH) (SEQ ID NO. 33)

wherein $X_{45,47}$ is a sequence that in the X sequence shown in FIG. 1, No. 45 Asp is replaced with Asn and No. 47 Gln with Ser respectively,
or a polypeptide with Met bound to the amino-terminus (SEQ ID NO. 34). A method of preparing same is shown in FIG. 17.

Subsequently, 5 micrograms of the resulting plasmid pTNF 489 was dissolved in 50 microliters of an aqueous solution containing 10 mM Tris-HCl (pH 7.5), 60 mM NaCl and 7 mM MgSO₄, and 20 units of restriction endonuclease ClaI and 20 units of restriction endonuclease AvaI (a product of Takara Shuzo) were added. The digestion reaction was run at 37° C. for 1 hour. After agarose gel electrophoresis (gel concentration 0.7 %), a DNA fragment (ClaI - AvaI) having a size of about 3.2 kbp and containing most of the plasmid pTNF488 was recovered from the agarose gel in accordance with the method of Example 3.

Figure 18:
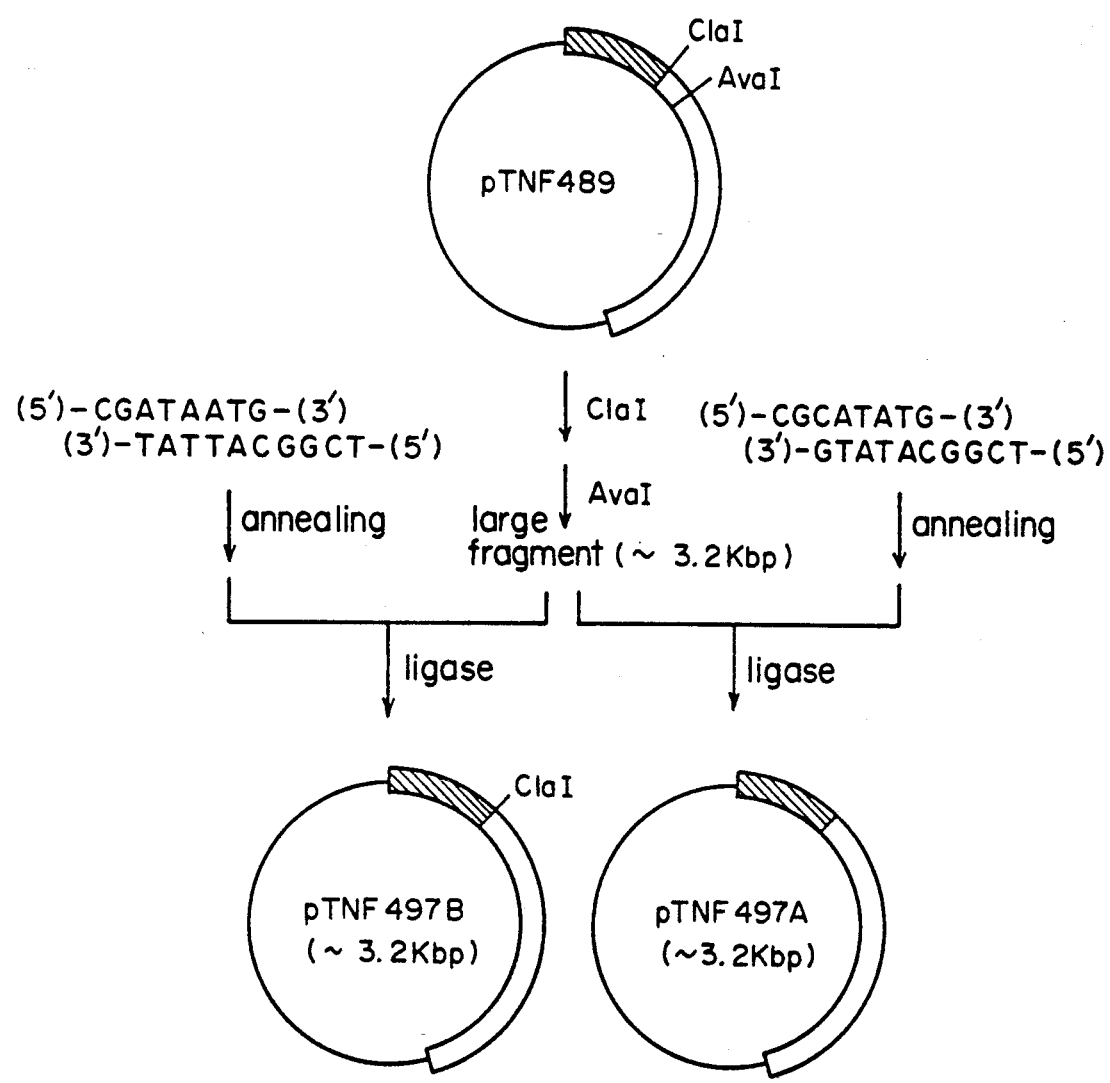

Meanwhile, in accordance with the method of Example 2, oligonucleotide having the base sequence shown in FIG. 18 was synthesized and purified. The resulting four synthetic oligonucreotides in an amount of 0.5 microgram each were mixed in a combination shown in FIG. 18. After annealing, the mixture was mixed with the DNA fragment (ClaI - AvaI) having a size of about 3.2 kbp, which was obtained above. After precipitation with ethanol, the ligation reaction with T4-DNA ligase was conducted in accordance with the method of Example 3. After the reaction, the ligation product was introduced into *E. coli* C600r-m- strain in accordance with the method of Example 3. Crones having the intended plasmids pTNF497A and pTNF497B (about 3.2 kbp in both cases) were selected from the transformants. These plasmids are plasmids capable of expressing an antitumorally active polypeptide gene encoding an antitumorally active polypeptide having the following amino acid sequence

(H₂N)-Pro-Ser-Asp-X₄₅,₄₇-Ile-Ile-Ala-Leu-
(COOH)(SEQ ID NO. 35)

wherein $X_{45,47}$ is as defined above, or a polypeptide with Met bound to the amino-terminus (SEQ. ID NO. 36). A method of preparing same is shown in FIG. 18.

Subsequently, 20 micrograms of the the plasmid pTNF497B capable of expressing the human TNF gene was digested with restriction endonuclease HindIII in accordance with the method of Example 4. The digestion reaction with restriction endonuclease NcoI (a product of Takara Shuzo) was run in an aqueous solution containing 50 mM Tris-HCl (pH 7.4), 100 mM NaCl and 10 mM MgSO₄ at 37° C. for 1 hour. After the reaction, agarose gel electrophoresis (gel concentration 0.7 %) and polyacrylamide gel electrophoresis (gel concentration 5 %) were conducted. A DNA fragment (NcoI - HindIII) having a size of about 140 bp and containing part of the human TNF gene was recovered from the polyacrylamide gel in accordance with the method of Example 2, and a DNA fragment (NcoI - HindIII) having a size of about 3.0 kbp and containing most of pTNF497B was recovered from the agarose gel in accordance with the method of Example 3.

In addition, the above DNA fragment (NcoI - HindIII) having a size of about 140 bp was dissolved in 50 microliters of an aqueous solution containing 10 mM Tris-HCl (pH 7.4), 10 mM MgSO₄ and 1 mM dithiothreitol, and 10 units of restriction endonuclease AccI (a product of Takara Shuzo) was added. The digestion reaction was run at 37° C. for 1 hour. After the reaction, polyacrylamide gel electrophoresis (gel concentration 8%) was conducted. A DNA fragment (NcoI - AccI) having a size of about 110 bp and containing part of the human TNF gene was recovered from the polyacrylamide gel in accordance with the method of Example 2.

In accordance with the method of Example 2, oligonucleotide having the base sequence shown in FIG. 19 was synthesized and purified. The terminals of the resulting two synthetic oligonucleotides in an amount of 0.5 microgram each were phosphorylated in accordance with the method of Example 3, followed by annealing.

After the annealing, the resulting doublestranded oligonucleotide was mixed with the DNA fragment (NcoI - HindIII) having a size of about 3.0 kbp and the DNA fragment (NcoI - AccI) having a size of about 110 bp and containing part of the TNF fragment, which were obtained above. After precipitation with ethanol, the ligation reaction with T4-DNA ligase was conducted in accordance with the method of Example 3. After the reaction, the ligation product was introduced into E. coli C600r-m- strain in accordance with the method of Example 3. Clones having the intended plasmid pTNF641 (about 3.2 kbp) were selected from the transformants. Said plasmid is a plasmid capable of expressing an antitumorally active polypeptide gene encoding an antitumorally active polypeptide having the following amino acid sequence

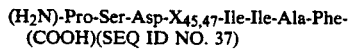
(H₂N)-Pro-Ser-Asp-X₄₅,₄₇-Ile-Ile-Ala-Phe-(COOH)(SEQ ID NO. 37)

wherein $X_{45,47}$ is as defined above, or a polypeptide with Met bound to the amino-terminus (SEQ ID NO. 38). A method of preparing same is shown in FIG. 19.

EXAMPLE 6

Determination of expression

E. coli ·C600r-m- strain having each of the human TNF gene expressing plasmid pTNF401A obtained in Example 4 and the expression plasmid pTNF471 or the expression plasmid pTNF616 obtained in Example 5, was inoculated in 250 ml of M9 medium containing 30 to 50 micrograms/ml of ampicillin, 0.2% of glucose and 4 mg/ml of casamino acid an aqueous solution (pH 7.4) of 0.6% NaHPO₄-0.3% K₂HPO₄-0.05% NaCl-0.1% NH₄Cl was sterilized in an autoclave, and an aqueous solution of MgSO₄ and an aqueous solution of CaCl₂, which had been separately sterilized in an autoclave, were added so that their final concentrations became 2 mM and 0.1 mM respectively], and cultivated at 37° C. with shaking until OD₆₀₀ reached 0.7 Then, 3-beta-indoleacrylic acid having a final concentration of 50 micrograms/ml was added to the culture broth, and the cultivation was continued further with shaking at 37° C. for 12 hours.

The E. coli cells were harvested by centrifugal separation, and washed with a PBS buffer (20 mM phosphate buffer containing 150 mM NaCl, pH 7.4). The washed cells were suspended in 10 ml of PBS buffer, and ruptured by using an ultrasonic generator (Model 200M, Kubota), and then the solid residues were removed by centrifugal separation.

Tris-HCl buffer (pH 6.8) SDS, 2-mercaptoethanol and glycerol were added to a portion of the resulting E. coli lysate so as to provide a final concentration of 60 mM, 2%, 4% and 10%, respectively, and SDS-polyacrylamide gel electrophoresis was performed (Suzuki, Iden (Genetics), 31, 43 (1977)). The concentration of the separating gel was adjusted to 15%, and an SDS, Tris-glycine system (U. K. Laemmli, Nature, 227, 680 (1970)) was used as an electrophoretic buffer. After the electrophoresis, the proteins in the gel were stained with Coumassie Brilliant Blue R-250 (Bio-Rad), and the expression of the human TNF gene and the novel antitumorally active polypeptide gene was determined. Some of the results were copied and shown in FIG. 20.

The stained gel was subjected to a chromatoscanner (Model CS-930, Shimadzu), and the proportion of the produced antitumorally active polypeptide in the E. coli cytoplasmic protein was calculated. It was found that in the E. coli having the human TNF gene expressing plasmid pTNF401A, about 19.4%, based on the total weight of the E. coli cytoplasmic protein, of the antitumorally active polypeptide was produced, in E. coli having the expression plasmid pTNF471 about 20.3%, based on the total amount of the cytoplasmic protein, of the antitumorally active polypeptide was produced, and in E. coli having the expression plasmid pTNF616, about 24.4% on the same basis, of the antitumorally active polypeptide was produced.

EXAMPLE 7

Evaluation of antitumor activity

The in vitro antitumor activity of the antitumorally active polypeptide was measured in accordance with the method of Ruff et al. cited hereinabove.

Specifically, the E. coli lysate containing the antitumorally active polypeptide obtained in Example 6 was diluted successively with a medium. The resulting sample (100 microliters) and 100 microliters of a suspension of mouse L-929 fibroblast cells (ATCC CCL-929) were mixed in a 96-well tissue-culture microtiter plate (Coaster). At this time, actinomycin D (Cosmegen, Banyu Pharmaceutical Co., Ltd.) was added to a final concentration of 1 microgram/ml. Eagle's minimum essential medium (produced by Nissui Seiyaku) containing 5% (vol/vol) bovine fetal serum was used as the medium. The microtiter plate was cultivated at 37° C. for 18 to 20 hours in air containing 5% carbon dioxide gas. Then, the living cells were stained with a crystal violet solution (prepared by dissolving 0.5% (wt/vol) of crystal violet in a 5% (vol/vol) aqueous solution of methanol). The excess of the crystal violet solution was washed off, and the microtiter plate was dried. The remaining crystal violet was extracted with 100 microliters of a 0.5% aqueous solution of SDS, and the absorbance of the extract at 595 nm was measured by an ELISA analyzer (model ETY-96, Toyo Sokki). This absorbance is proportional to the number of surviving cells. The dilution ratio of the E. coli lysate containing the antitumorally active polypeptide, which corresponds to 50% of the absorbance of the E. coli lysate to which no diluting solution was added, was determined from a graph (for example, FIG. 21), and this dilution ratio is defined as one unit. It is clear from FIG. 21 that 100 microliters of the E. coli lysate containing the human TNF protein encoded by the expression plasmid pTNF401A has an activity of about $7.6 \times 10^6$ units; 100 microliters of the E. coli lysate containing the antitumorally active polypeptide encoded by the expression plasmid pTNF471 has an activity of about $6.9 \times 10^7$ units; and 100 microliters of the E. coli lysate containing the antitumorally active polypeptide encoded by the expression plasmid pTNF616 has an activity of about $1.9 \times 10^8$ units.

The total amount of proteins contained in the E. coli lysates obtained in Example 6 was determined by using a protein assay kit, and calculated from a calibration curve prepared by using a bovine serum albumin. From the amounts of expression, the activity values and the amounts of proteins determined above, the specific activities of the antitumorally active polypeptide were calculated, and the results are shown in Table 1. Table 1 shows that the antitumorally active polypeptide encoded by pTNF616 has about 18 times as high a specific activity as the human TNF protein, and about twice as high a specific activity as the antitumorally active polypeptide encoded by pTNF471.

calculated. The results are shown in Tables 4 and 5. From said Tables 4 and 5, it followed that the antitumorally active polypeptide encoded by pTNF617 has about 12 times as high a specific activity as the human TNF protein, and about 1.4 times as high a specific activity as the antitumorally active polypeptide encoded by pTNF471.

TABLE 1

Comparison in antitumoractivity in vitro between human TNF protein and antitumorally active polypeptide of this invention

| Physiologically active polypeptide | Human TNF protein | Antitumorally active polypeptide | Antitumorally active polypeptide |
|---|---|---|---|
| Plasmid | pTNF 401A | pTNF 471 | pTNF 616 |
| $\frac{\text{Physiologically active polypeptide}}{\text{Total weight of } E.\ coli \text{ cytoplasmic protein}}$ (%) | 19.4 | 20.3 | 24.4 |
| Activity (units/100 microliters-lyoate) | $7.6 \times 10^6$ | $6.9 \times 10^7$ | $1.9 \times 10^8$ |
| Total weight of E. coli cytoplasmic protein (mg/ml-lysate) | 7.1 | 6.2 | 7.5 |
| Specific activity (units/mg-physiologically active polypeptide) | $5.5 \times 10^7$ | $5.5 \times 10^8$ | $1.0 \times 10^9$ |

EXAMPLE 8

Regarding E. coli having each of the plasmids prepared in Example 5, expression was determined and antitumor activity in vitro was evaluated in accordance with Examples 6 and 7. By the way, determination of expression and evaluation of antitumor activity were also conducted on E. coli having plasmid pTNF401 or pTNF471 for comparison as required.

Evaluation of the antitumorally active polypeptide encoded by pTNF617

The proportion of the antitumorally active polypeptide occupied in E. coli cytoplasmic protein of the antitumorally active polypeptide was calculated according to Example 6. Consequently, it was found that in E. coli having the human gene expressing plasmid pTNF401A, 16.2%, based on the total weight of the E. coli cytoplasmic protein, of the human TNF protein was produced; in E. coli having the expression plasmid pTNF471, about 23.2%, on the same basis, of the antitumorally active polypeptide was produced; and in E. coli having plasmid pTNF617 capable of expressing the antitumorally active polypeptide gene, about 18.7%, on the same basis, of the antitumorally active polypeptide was produced.

In accordance with Example 7, a dilution ratio of E. coli lysate corresponding to 50% of absorbance of E. coli lysate containing the antitumorally active polypeptide, etc., to which no diluting solution was added, was found by a graph (e.g. FIG. 22), and the very dilution ratio was defined as a unit. From FIG. 22, it became apparent that 100 microliters of the E. coli lysate containing the human TNF protein encoded by the expression plasmid pTNF401A has an activity of about $3.3 \times 10^6$ units, 100 microliters of E. coli lysate containing the antitumorally active polypeptide encoded by the expression plasmid pTNF471 has an activity of about $3.7 \times 10^7$ units, and 100 microliters of the E. coli lysate containing the antitumorally active polypeptide encoded by the expression plasmid pTNF617 has an activity of about $4.0 \times 10^7$ units.

The total amount of proteins contained in the E. coli lysates was determined by using a protein assay kit (made by Bio-Rad), and calculated from a calibration curve prepared by using a bovin serum albumin. From the amounts of expression, the activity values and the amounts of proteins determined above, the specific activities of the antitumorally active polypeptide were Evaluation of the antitumorally active polypeptide encoded by pTNF618

The proportion of the antitumorally active polypeptide occupied in the E. coli cytoplasmic protein was calculated in accordance with Example 6. It was consequently found that in E. coli having the human TNF gene expressing plasmid pTNF401A, 16.2%, based on the total weight of the cytoplasmic protein, of the human TNF gene was produced; in E. coli having the expression plasmid pTNF471, about 23.2%, on the same basis, of the antitumorally active polypeptide was produced; and in E. coli having the expression plasmid pTNF618, about 13.5%, on the same basis, of the antitumorally active polypeptide was produced.

In accordance with Example 7, a dilution ratio of the E. coli lysate corresponding to 50% of absorbance of E. coli lysate containing the antitumorally active polypeptide, etc. was found by a graph (e.g. FIG. 23), and the dilution ratio was defined as a unit. From FIG. 23, it became clear that 100 microliters of the E. coli lysate containing the human TNF protein encoded by the expression plasmid pTNF401A has an activity of about $3.8 \times 10^6$ units, 100 microliters of the E. coli lysate containing the antitumorally active polypeptide encoded by expression plasmid pTNF471 has an activity of about $3.6 \times 10^7$ units; and 100 microliters of the E. coli lysate containing the antitumorally active polypeptide encoded by the expression plasmid pTNF618 has an activity of about $3.9 \times 10^7$ units.

The total amount of proteins contained in the E. coli lysates was determined by using a protein assay kit (made by Bio-Rad), and calculated from a calibration curve prepared by using a bovin serum albumin. From the amounts of expression, the activity values and the amounts of proteins determined above, the specific activities of the antitumorally active polypeptide were calculated. The results are shown in Tables 4 and 5. Tables 4 and 5 revealed that the antitumorally active polypeptide encoded by pTNF618 has about 14 times as high a specific activity as the human TNF protein and about twice as high a specific activity as the antitumorally active polypeptide encoded by pTNF471.

Evaluation of the antitumorally active polypeptide encoded by pTNF619

The proportion of the antitumorally active polypeptide occupied in the *E. coli* cytoplasmic protein was calculated in accordance with Example 6. As a result, it was found that in *E. coli* having the human TNF gene expressing plasmid pTNF401A, about 16.3%, based on the total weight of the cytoplasmic protein, of the human TNF gene was produced; in *E. coli* having the expression plasmid pTNF471, about 18.3%, based on the total weight of the cytoplasmic protein, of the antitumorally active polypeptide was produced; and in *E. coli* having the expression plasmid pTNF619, about 20.3%, on the same basis, of the antitumorally active polypeptide was produced.

In accordance with Example 7, a dilution ratio of the *E. coli* lysate corresponding to 50% of absorbance of *E. coli* lysate containing the antitumorally active polypeptide, etc., to which no diluting solution was added, was found by a graph (e.g. FIG. 24), and the dilution ratio was defined as a unit. From FIG. 24, it was found that 100 microliters of the *E. coli* lysate containing the human TNF protein encoded by the expression plasmid pTNF401A has an activity of about $5.3 \times 10^6$ units, 100 microliters of the *E. coli* lysate containing the antitumorally active polypeptide encoded by the expression plasmid pTNF471 has an activity of about $5.8 \times 10^7$ units, and 100 microliters of the *E. coli* lysate containing the antitumorally active polypeptide encoded by the expression plasmid pTNF619 has an activity of about $1.3 \times 10^8$ units.

The total amount of the proteins contained in the *E. coli* lysates was determined by using a protein assay kit (made by Bio-Rad), and calculated from a calibration curve prepared by using a bovin serum albumin. From the amounts of expression, the activity values and the amounts of proteins determined above, the specific activities of the lysates containing the antitumorally active polypeptides were calculated. The results are shown in Tables 4 and 5. From Tables 4 and 5, it became apparent that the antitumorally active polypeptide encoded by pTNF619 has about 18 times as high a specific activity as the human TNF protein and about twice as high a specific activity as the antitumorally active polypeptide encoded by pTNF471.

Evaluation of the other antitumorally active polypeptides

One hundred microliters of the *E. coli* lysate containing the antitumorally active polypeptide encoded by the expression plasmid pTNF621 had an activity of about $10^8$ units, and was higher in activity than the *E. coli* lysate containing the human TNF protein. One hundred microliters of the *E. coli* lysate containing the antitumorally active polypeptide encoded by the expression plasmid pTNF637 had an activity of about $2 \times 10^3$ units.

The total amount of the proteins contained in the *E. coli* lysate having the antitumorally active polypeptide encoded by the expression plasmid pTNF637 was determined by using a protein assay kit (made by BioRad), and calculated from a calibration curve prepared by using a bovin serum albumin. From the amounts of expression, the activity values and the amounts of proteins determined above, the specific activity of the lysate containing the antitumorally active polypeptide was calculated, and found to be $8.3 \times 10^2$ (units/mg-protein).

Regarding pTNF's 620, 622, 624, 625, 626, 627, 628, 629, 630, 631, 632, 633, 634, 642, 643 and 641, determination of expression and evaluation of antitumor activity in vivo were likewise conducted in accordance with Examples 6 and 7. FIGS. 25 to 30 show survival rate vs. lysate dilution ratio.

As a result, the activity per 100 microliters of the *E. coli* lysate is shown in Table 1, the ratio of the antitumorally active polypeptide in the *E. coli* cytoplasmic protein in Table 2, the total concentration of the *E. coli* protein in the lysate in Table 3, the specific activity of the antitumorally active polypeptide in Table 4, and the specific activity of the antitumorally active polypeptide given when the intact TNF (encoded by pTNF401A) is taken as 1 in Table 5, respectively. It becomes clear that the antitumorally active polypeptide produced from *E. coli* having the plasmid pTNF616, 617, 618, 619, 620, 643 or 641 is higher in specific activity than the intact TNF.

EXAMPLE 9

Separation and purification of the antitumorally active polypeptide

Separation and purification of the antitumorally active polypeptides from the *E. coli* lysates having pTNF471, pTNF616 and pTNF619, which were obtained in Example 5, were carried out by using carboxymethylsepharose column chromatography (made by Pharmacia). First, the resin was packed in the column, and fully equilibrated with a 50 mN citrate buffer (pH 6.2). The lysate containing the antitumorally active polypeptide, obtained in Example 2, was then charged onto said column. After the resulting substance was thoroughly washed with PBS buffer 20 mM phosphate buffer (pH 7.4) containing 140 mM NaCl, the antitumorally active polypeptide was eluted with 20 mM phosphate buffer (pH 7.4) containing 420 mM NaCl. The eluted antitumorally active polypeptide was subjected to SDS-polyacrylamide gel electrophoresis (a concentration of a separation gel 15%). After the electrophoresis, protein bands in the gel were stained with a dye. Consequently, one band was observed only in a position of a molecular weight of about 15,000 to 17,000. It was confirmed that the antitumorally active polypeptide having a purity of 98% was obtained.

EXAMPLE 10

Evaluation of activity of the purified product

The antitumor activity in vitro of the antitumorally active polypeptides purified in Example 9 was evaluated as in Example 7 according to the Ruff's method. FIG. 31 revealed that 1 mg of the purified product of the antitumorally active polypeptide encoded by the expression plasmid pTNF471 has an activity of about $8.3 \times 10^8$ units, 1 mg of the purified product of the antituplasmid pTNF616 has an activity of about $1.2 \times 10^9$ units, and 1 mg of the purified product of the antitumorally active polypeptide encoded by the expression plasmid pTNF619 has an activity of about $1.6 \times 10^9$ units.

TABLE 2

Activity per 100 microliters of E. coli lysate
($10^7$ units/100 microliters of lysate)

| Plasmid | Test No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| pTNF 401A | 0.76 | 0.33 | 0.38 | 0.53 | 0.42 | | | | 0.11 | | | 1.3 |
| pTNF 471 | 6.9 | 3.7 | 3.6 | 5.8 | | | | | | | | |
| pTNF 616 | 19 | | | | | | | | | | | |
| pTNF 617 | | 4.0 | | | | | | | | | | |
| pTNF 618 | | | 3.9 | | | | | | | | | |
| pTNF 619 | | | | 13 | | | | | | | | |
| pTNF 620 | | | | | 4.6 | | | | | | | |
| pTNF 633 | | | | | | 9.6 | | | | | | |
| pTNF 634 | | | | | | | 0.59 | | | | | |
| pTNF 642 | | | | | | | | 0.05 | | | | |
| pTNF 643 | | | | | | | | | 0.28 | | | |
| pTNF 621 | | | | | | | | | | 10 | | |
| pTNF 637 | | | | | | | | | | | $2 \times 10^{-4}$ | |
| pTNF 641 | | | | | | | | | | | | 1.2 |

TABLE 3

Proportion of the antitumorally active polypeptide occupied
in the E. coli cytoplastic protein
(antitumorally active polypeptide/total weight of E. coli
cytoplastic protein; unit %)

| Plasmid | Test No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| pTNF 401A | 19.4 | 16.2 | 16.2 | 16.3 | 16.2 | | | | 13.7 | | | 17 |
| pTNF 471 | 20.3 | 23.2 | 23.2 | 18.3 | | | | | | | | |
| pTNF 616 | 24.4 | | | | | | | | | | | |
| pTNF 617 | | 18.7 | | | | | | | | | | |
| pTNF 618 | | | 13.5 | | | | | | | | | |
| pTNF 619 | | | | 20.3 | | | | | | | | |
| pTNF 620 | | | | | 26.6 | | | | | | | |
| pTNF 633 | | | | | | — | | | | | | |
| pTNF 634 | | | | | | | — | | | | | |
| pTNF 642 | | | | | | | | — | | | | |
| pTNF 643 | | | | | | | | | 13.9 | | | |
| pTNF 621 | | | | | | | | | | — | | |
| pTNF 637 | | | | | | | | | | | — | |
| pTNF 641 | | | | | | | | | | | | 10 |

TABLE 4

Total amount of E. coli proteins in lysates
(mg/ml-lysate)

| Plasmid | Test No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| pTNF 401A | 7.1 | 6.6 | 6.6 | 6.5 | | | | | 4.4 | | | 10.2 |
| pTNF 471 | 6.2 | 6.2 | 6.2 | 7.1 | | | | | | | | |
| pTNF 616 | 7.5 | | | | | | | | | | | |
| pTNF 617 | | 6.0 | | | | | | | | | | |
| pTNF 618 | | | 5.9 | | | | | | | | | |
| pTNF 619 | | | | 7.2 | | | | | | | | |
| pTNF 620 | | | | | 6.5 | | | | | | | |
| pTNF 633 | | | | | | — | | | | | | |
| pTNF 634 | | | | | | | — | | | | | |
| pTNF 642 | | | | | | | | — | | | | |
| pTNF 643 | | | | | | | | | 3.7 | | | |
| pTNF 621 | | | | | | | | | | | | |
| pTNF 637 | | | | | | | | | | | | |
| pTNF 641 | | | | | | | | | | | | 8.9 |

TABLE 5

Specific activity of the antitumorally active polypeptide
($10^8$ units/mg-antitumorally active polypeptide)

| Plasmid | Test No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| pTNF 401A | 0.55 | 0.31 | 0.35 | 0.50 | 0.39 | | | | 0.19 | | | 0.75 |
| pTNF 471 | 5.5 | 2.6 | 2.5 | 4.4 | | | | | | | | |
| pTNF 616 | 10 | | | | | | | | | | | |
| pTNF 617 | | 3.6 | | | | | | | | | | |
| pTNF 618 | | | 4.8 | | | | | | | | | |
| pTNF 619 | | | | 8.9 | | | | | | | | |

TABLE 5-continued

Specific activity of the antitumorally active polypeptide
($10^8$ units/mg-antitumorally active polypeptide)

| Plasmid | 1 | 2 | 3 | 4 | 5 | 6 | 7 | 8 | 9 | 10 | 11 | 12 |
|---|---|---|---|---|---|---|---|---|---|---|---|---|
| pTNF 620 | | | | | 2.7 | | | | | | | |
| pTNF 633 | | | | | | | | | | | | |
| pTNF 634 | | | | | | | | | | | | |
| pTNF 642 | | | | | | | | | | | | |
| pTNF 643 | | | | | | | | | | 0.54 | | |
| pTNF 621 | | | | | | | | | | — | | |
| pTNF 637 | | | | | | | | | | | $8.3 \times 10^{-6}$ | |
| pTNF 641 | | | | | | | | | | | | 1.3 |

TABLE 6

Specific activity of the antitumorally active polypeptide
when intact polypeptide (pTNF401A) is taken as 1

| Plasmid | 1 | 2 | 3 | 4 | 5 | 6 | 7 | 8 | 9 | 10 | 11 | 12 |
|---|---|---|---|---|---|---|---|---|---|---|---|---|
| pTNF 401A | 1 | 1 | 1 | 1 | 1 | — | — | — | — | — | — | 1 |
| pTNF 471 | 10 | 8.4 | 7.1 | 8.8 | | | | | | | | |
| pTNF 616 | 18.2 | | | | | | | | | | | |
| pTNF 617 | | 11.6 | | | | | | | | | | |
| pTNF 618 | | | 13.7 | | | | | | | | | |
| pTNF 619 | | | | 17.8 | | | | | | | | |
| pTNF 620 | | | | | 6.9 | | | | | | | |
| pTNF 633 | | | | | | — | | | | | | |
| pTNF 634 | | | | | | | — | | | | | |
| pTNF 642 | | | | | | | | — | | | | |
| pTNF 643 | | | | | | | | | 2.8 | | | |
| pTNF 621 | | | | | | | | | | — | | |
| pTNF 637 | | | | | | | | | | | — | |
| pTNF 641 | | | | | | | | | | | | 1.7 |

---

What we claim is:

1. A modified TNF polypeptide represented by formula (I)

$$(NH_2)-(Met)_n-A-X-B-(COOH) \quad (I)$$

wherein
n is 0 or 1,
A denotes -Arg-Lys-Arg-,
B denotes -Ile-Ile-Ala-Phe-, -Ile-Ile-Ala-Trp-, -Ile-Ile-Trp-Leu, or Ile-Ile-Phe-Leu-,
X denotes -Lys-Pro-Val-Ala-His-Val-Val-Ala-Asn-Pro-Gln-Ala-Glu-Gly-Gln-Leu-Gln-Trp-Leu-Asn-Arg-Arg-Ala-Asn-Ala-Leu-Leu-Ala-Asn-Gly-Val-Glu-Leu-Arg-Asp-Asn-Gln-Leu-Val-Val-Pro-Ser-Glu-Gly-Leu-Tyr-Leu-Ile-Tyr-Ser-Gln-Val-Leu-Phe-Lys-Gly-Gln-Gly-Cys-Pro-Ser-Thr-His-Val-Leu-Leu-Thr-His-Thr-Ile-Ser-Arg-Ile-Ala-Val-Ser-Tyr-Gln-Thr-Lys-Val-Asn-Leu-Leu-Ser- Ala-Ile-Lys-Ser-Pro-Cys-Gln-Arg-Glu-Thr-Pro-
Glu-Gly-Ala-Glu-Ala-Lys-Pro-Trp-Tyr-Glu-Pro-
Ile-Tyr-Leu-Gly-Gly-Val-Phe-Gln-Leu-Glu-Lys-
Gly-Asp-Arg-Leu-Ser-Ala-Glu-Ile-Asn-Arg-Pro-
Asp-Typ-Leu-Asp-Phe-Ala-Glu-Ser-Gly-Gln-Val-
Tyr-Phe-Gly-.

2. A recombinant plasmic comprising a DNA sequence encoding the polypeptide of formula (I)

$$(NH_2)\text{-}(Met)_n\text{-}A\text{-}X\text{-}B\text{-}(COOH) \qquad (I)$$

wherein
n is 0 or 1,
A denotes -Arg-Lys-Arg-,
B denotes -Ile-Ile-Ala-Phe-, -Ile-Ile-Ala-Trp-, -Ile-Ile-Trp-Leu, or Ile-Ile-Phe-Leu-,
X denotes -Lys-Pro-Val-Ala-His-Val-Val-Ala-Asn-
Pro-Gln-Ala-Glu-Gly-Gln-Leu-Gln-Trp-Leu-Asn-
Arg-Arg-Ala-Asn-Ala-Leu-Leu-Ala-Asn-Gly-
Val-Glu-Leu-Arg-Asp-Asn-Gln-Leu-Val-Val-Pro-
Ser-Glu-Gly-Leu-Tyr-Leu-Ile-Tyr-Ser-Gln-Val-
Leu-Phe-Lys-Gly-Gln-Gly-Cys-Pro-Ser-Thr-His-
Val-Leu-Leu-Thr-His-Thr-Ile-Ser-Arg-Ile-Ala-
Val-Ser-Tyr-Gln-Thr-Lys-Val-Asn-Leu-Leu-Ser-
Ala-Ile-Lys-Ser-Pro-Cys-Gln-Arg-Glu-Thr-Pro-
Glu-Gly-Ala-Glu-Ala-Lys-Pro-Trp-Tyr-Glu-Pro-
Ile-Tyr-Leu-Gly-Gly-Val-Phe-Gln-Leu-Glu-Lys-
Gly-Asp-Arg-Leu-Ser-Ala-Glu-Ile-Asn-Arg-Pro-
Asp-Tyr-Leu-Asp-Phe-Ala-Glu-Ser-Gly-Gln-Val-
Tyr-Phe-Gly-.

3. The plasmid of claim 1 which is pTNF616, pTNF617, pTNF618 or pTNF619.

4. The plasmid of claim 1 which is transformed with the recombinant plasmid having the DNA sequence encoding the modified TNF polypeptide of formula (I)

$$(NH_2)\text{-}(Met)_n\text{-}A\text{-}X\text{-}B\text{-}(COOH) \qquad (I)$$

wherein
n is 0 or 1,
A denotes -Arg-Lys-Arg-,
B denotes -Ile-Ile-Ala-Phe-, -Ile-Ile-Ala-Trp-, -Ile-Ile-Trp-Leu, or Ile-Ile-Phe-Leu-,
X denotes -Lys-Pro-val-Ala-His-Val-Val-Ala-Asn-
Pro-Gln-Ala-Glu-Gly-Gln-Leu-Gln-Trp-Leu-Asn-
Arg-Arg-Ala-Asn-Ala-Leu-Leu-Ala-Asn-Gly-
Val-Glu-Leu-Arg-Asp-Asn-Gln-Leu-Val-Val-Pro-
Ser-Glu-Gly-Leu-Tyr-Leu-Ile-Tyr-Ser-Gln-Val-
Leu-Phe-Lys-Gly-Gln-Gly-Cys-Pro-Ser-Thr-His-
Val-Leu-Leu-Thr-His-Thr-Ile-Ser-Arg-Ile-Ala-
Val-Ser-Tyr-Gln-Thr-Lys-Val-Asn-Leu-Leu-Ser-
Ala-Ile-Lys-Ser-Pro-Cys-Gln-Arg-Glu-Thr-Pro-
Glu-Gly-Ala-Glu-Ala-Lys-Pro-Trp-Tyr-Glu-Pro-
Ile-Tyr-Leu-Gly-Gly-Val-Phe-Gln-Leu-Glu-Lys-
Gly-Asp-Arg-Leu-Ser-Ala-Glu-Ile-Asn-Arg-Pro-
Asp-Tyr-Leu-Asp-Phe-Ala-Glu-Ser-Gly-Gln-Val-
Tyr-Phe-Gly-.

5. The unicellular microorganism of claim 4 which is *Escherichia coli.*

6. A process for producing the modified TNF polypeptide of formula (I)

$$(NH_2)\text{-}(Met)_n\text{-}A\text{-}X\text{-}B\text{-}(COOH) \qquad (I)$$

wherein
n is 0 or 1,
A denotes -Arg-Lys-Arg-,
B denotes -Ile-Ile-Ala-Phe-, -Ile-Ile-Ala-Trp-, -Ile-Ile-Trp-Leu, or Ile-Ile-Phe-Leu-,
X denotes -Lys-Pro-Val-Ala-His-Val-Val-Ala-Asn-
Pro-Gln-Ala-Glu-Gly-Gln-Leu-Gln-Trp-Leu-Asn-
Arg-Arg-Ala-Asn-Ala-Leu-Leu-Ala-Asn-Gly-
Val-Glu-Leu-Arg-Asp-Asn-Gln-Leu-Val-Val-Pro-
Ser-Glu-Gly-Leu-Tyr-Leu-Ile-Tyr-Ser-Gln-Val-
Leu-Phe-Lys-Gly-Gln-Gly-Cys-Pro-Ser-Thr-His-
Val-Leu-Leu-Thr-His-Thr-Ile-Ser-Arg-Ile-Ala-
Val-Ser-Tyr-Gln-Thr-Lys-Val-Asn-Leu-Leu-Ser-
Ala-Ile-Lys-Ser-Pro-Cys-Gln-Arg-Glu-Thr-Pro-
Glu-Gly-Ala-Glu-Ala-Lys-Pro-Trp-Tyr-Glu-Pro-
Ile-Tyr-Leu-Gly-Gly-Val-Phe-Gln-Leu-Glu-Lys-
Gly-Asp-Arg-Leu-Ser-Ala-Glu-Ile-Asn-Arg-Pro-
Asp-Typ-Leu-Asp-Phe-Ala-Glu-Ser-Gly-Gln-Val-
Tyr-Phe-Gly-,
which comprises cultivating an *Escherichia coli* which is transformed with a DNA sequence encoding the polypeptide of formula (I) to produce and accumulate the polypeptide of formula (I) in a culture broth, and separating the polypeptide from the resulting culture broth.

7. A pharmaceutical composition comprising an antitumorally effective amount of the modified TNF polypeptide of formula (I)

$$(NH_2)\text{-}(Met)_n\text{-}A\text{-}X\text{-}B\text{-}(COOH) \qquad (I)$$

wherein
n is 0 or 1,
A denotes -Arg-Lys-Arg-,
B denotes -Ile-Ile-Ala-Phe-, -Ile-Ile-Ala-Trp-, -Ile-Ile-Trp-Leu, or Ile-Ile-Phe-Leu-,
X denotes -Lys-Pro-Val-Ala-His-Val-Val-Ala-Asn-
Pro-Gln-Ala-Glu-Gly-Gln-Leu-Gln-Trp-Leu-Asn-
Arg-Arg-Ala-Asn-Ala-Leu-Leu-Ala-Asn-Gly-
Val-Glu-Leu-Arg-Asp-Asn-Gln-Leu-Val-Val-Pro-
Ser-Glu-Gly-Leu-Tyr-Leu-Ile-Tyr-Ser-Gln-Val-
Leu-Phe-Lys-Gly-Gln-Gly-Cys-Pro-Ser-Thr-His-
Val-Leu-Leu-Thr-His-Thr-Ile-Ser-Arg-Ile-Ala-
Val-Ser-Tyr-Gln-Thr-Lys-Val-Asn-Leu-Leu-Ser-
Ala-Ile-Lys-Ser-Pro-Cys-Gln-Arg-Glu-Thr-Pro-
Glu-Gly-Ala-Glu-Ala-Lys-Pro-Trp-Tyr-Glu-Pro-
Ile-Tyr-Leu-Gly-Gly-Val-Phe-Gln-Leu-Glu-Lys-
Gly-Asp-Arg-Leu-Ser-Ala-Glu-Ile-Asn-Arg-Pro-
Asp-Tyr-Leu-Asp-Phe-Ala-Glu-Ser-Gly-Gln-Val-
Tyr-Phe-Gly-,
and a pharmaceutically acceptable amount of a carrier.

* * * * *

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
( A ) LENGTH: 147 amino acids
( B ) TYPE: amino acid
( C ) STRANDEDNESS: single
( D ) TOPOLOGY: linear ( i x ) FEATURE:
( A ) NAME/KEY:
( B ) LOCATION:
( C ) IDENTIFICATION METHOD:
( D ) OTHER INFORMATION:

( x i ) SEQUENCE DESCRIPTION: SEQ ID NO:1:

```
Lys Pro Val Ala His Val Val Ala Asn Pro Gln Ala Glu Gly Gln
 1               5                  10                  15

Leu Gln Trp Leu Asn Arg Arg Ala Asn Ala Leu Leu Ala Asn Gly
                20                  25                  30

Val Glu Leu Arg Asp Asn Gln Leu Val Val Pro Ser Glu Gly Leu
                35                  40                  45

Tyr Leu Ile Tyr Ser Gln Val Leu Phe Lys Gly Gln Gly Cys Pro
                50                  55                  60

Ser Thr His Val Leu Leu Thr His Thr Ile Ser Arg Ile Ala Val
                65                  70                  75

Ser Tyr Gln Thr Lys Val Asn Leu Leu Ser Ala Ile Lys Ser Pro
                    80                  85                  90
```

```
Cys Gln Arg Glu Thr Pro Glu Gly Ala Glu Ala Lys Pro Trp Tyr
                95                  100                 105

Glu Pro Ile Tyr Leu Gly Gly Val Phe Gln Leu Glu Lys Gly Asp
                110                 115                 120

Arg Leu Ser Ala Glu Ile Asn Arg Pro Asp Tyr Leu Asp Phe Ala
                125                 130                 135

Glu Ser Gly Gln Val Tyr Phe Gly Ile Ile Ala Phe
                140                 145
```

( 2 ) INFORMATION FOR SEQ ID NO:2:

( i ) SEQUENCE CHARACTERISTICS:
    ( A ) LENGTH: 148 amino acids
    ( B ) TYPE: amino acid
    ( C ) STRANDEDNESS: single
    ( D ) TOPOLOGY: linear ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO:2:

```
Asp Lys Pro Val Ala His Val Val Ala Asn Pro Gln Ala Glu Gly
 1              5                   10                  15

Gln Leu Gln Trp Leu Asn Arg Arg Ala Asn Ala Leu Leu Ala Asn
                20                  25                  30

Gly Val Glu Leu Arg Asp Asn Gln Leu Val Val Pro Ser Glu Gly
                35                  40                  45

Leu Tyr Leu Ile Tyr Ser Gln Val Leu Phe Lys Gly Gln Gly Cys
                50                  55                  60

Pro Ser Thr His Val Leu Leu Thr His Thr Ile Ser Arg Ile Ala
                65                  70                  75

Val Ser Tyr Gln Thr Lys Val Asn Leu Leu Ser Ala Ile Lys Ser
                80                  85                  90

Pro Cys Gln Arg Glu Thr Pro Glu Gly Ala Glu Ala Lys Pro Trp
                95                  100                 105

Tyr Glu Pro Ile Tyr Leu Gly Gly Val Phe Gln Leu Glu Lys Gly
                110                 115                 120

Asp Arg Leu Ser Ala Glu Ile Asn Arg Pro Asp Tyr Leu Asp Phe
                125                 130                 135

Ala Glu Ser Gly Gln Val Tyr Phe Gly Ile Ile Ala Phe
                140                 145
```

( 2 ) INFORMATION FOR SEQ ID NO:3:

( i ) SEQUENCE CHARACTERISTICS:
    ( A ) LENGTH: 149 amino acids
    ( B ) TYPE: amino acid
    ( C ) STRANDEDNESS: single
    ( D ) TOPOLOGY: linear ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO:3:

```
Ser Asp Lys Pro Val Ala His Val Val Ala Asn Pro Gln Ala Glu
 1              5                   10                  15

Gly Gln Leu Gln Trp Leu Asn Arg Arg Ala Asn Ala Leu Leu Ala
                20                  25                  30
```

```
Asn  Gly  Val  Glu  Leu  Arg  Asp  Asn  Gln  Leu  Val  Val  Pro  Ser  Glu
               35                      40                         45

Gly  Leu  Tyr  Leu  Ile  Tyr  Ser  Gln  Val  Leu  Phe  Lys  Gly  Gln  Gly
               50                      55                         60

Cys  Pro  Ser  Thr  His  Val  Leu  Leu  Thr  His  Thr  Ile  Ser  Arg  Ile
               65                      70                         75

Ala  Val  Ser  Tyr  Gln  Thr  Lys  Val  Asn  Leu  Leu  Ser  Ala  Ile  Lys
               80                      85                         90

Ser  Pro  Cys  Gln  Arg  Glu  Thr  Pro  Glu  Gly  Ala  Glu  Ala  Lys  Pro
               95                     100                        105

Trp  Tyr  Glu  Pro  Ile  Tyr  Leu  Gly  Gly  Val  Phe  Gln  Leu  Glu  Lys
              110                     115                        120

Gly  Asp  Arg  Leu  Ser  Ala  Glu  Ile  Asn  Arg  Pro  Asp  Tyr  Leu  Asp
              125                     130                        135

Phe  Ala  Glu  Ser  Gly  Gln  Val  Tyr  Phe  Gly  Ile  Ile  Ala  Phe
              140                     145
```

( 2 ) INFORMATION FOR SEQ ID NO:4:

( i ) SEQUENCE CHARACTERISTICS:
    ( A ) LENGTH: 150 amino acids
    ( B ) TYPE: amino acid
    ( C ) STRANDEDNESS: single
    ( D ) TOPOLOGY: linear ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO:4:

```
Pro  Ser  Asp  Lys  Pro  Val  Ala  His  Val  Val  Ala  Asn  Pro  Gln  Ala
 1                 5                      10                         15

Glu  Gly  Gln  Leu  Gln  Trp  Leu  Asn  Arg  Arg  Ala  Asn  Ala  Leu  Leu
               20                      25                         30

Ala  Asn  Gly  Val  Glu  Leu  Arg  Asp  Asn  Gln  Leu  Val  Val  Pro  Ser
               35                      40                         45

Glu  Gly  Leu  Tyr  Leu  Ile  Tyr  Ser  Gln  Val  Leu  Phe  Lys  Gly  Gln
               50                      55                         60

Gly  Cys  Pro  Ser  Thr  His  Val  Leu  Leu  Thr  His  Thr  Ile  Ser  Arg
               65                      70                         75

Ile  Ala  Val  Ser  Tyr  Gln  Thr  Lys  Val  Asn  Leu  Leu  Ser  Ala  Ile
               80                      85                         90

Lys  Ser  Pro  Cys  Gln  Arg  Glu  Thr  Pro  Glu  Gly  Ala  Glu  Ala  Lys
               95                     100                        105

Pro  Trp  Tyr  Glu  Pro  Ile  Tyr  Leu  Gly  Gly  Val  Phe  Gln  Leu  Glu
              110                     115                        120

Lys  Gly  Asp  Arg  Leu  Ser  Ala  Glu  Ile  Asn  Arg  Pro  Asp  Tyr  Leu
              125                     130                        135

Asp  Phe  Ala  Glu  Ser  Gly  Gln  Val  Tyr  Phe  Gly  Ile  Ile  Ala  Phe
              140                     145                        150
```

( 2 ) INFORMATION FOR SEQ ID NO:5:

( i ) SEQUENCE CHARACTERISTICS:
    ( A ) LENGTH: 150 amino acids
    ( B ) TYPE: amino acid
    ( C ) STRANDEDNESS: single
    ( D ) TOPOLOGY: linear ( i x ) FEATURE:
    ( A ) NAME/KEY:

(B) LOCATION:
(C) IDENTIFICATION METHOD:
(D) OTHER INFORMATION:

(xi) SEQUENCE DESCRIPTION: SEQ ID NO:5:

| Arg | Lys | Arg | Lys | Pro | Val | Ala | His | Val | Val | Ala | Asn | Pro | Gln | Ala |
|---|---|---|---|---|---|---|---|---|---|---|---|---|---|---|
| 1 | | | | 5 | | | | | 10 | | | | | 15 |
| Glu | Gly | Gln | Leu | Gln | Trp | Leu | Asn | Arg | Arg | Ala | Asn | Ala | Leu | Leu |
| | | | | 20 | | | | | 25 | | | | | 30 |
| Ala | Asn | Gly | Val | Glu | Leu | Arg | Asp | Asn | Gln | Leu | Val | Val | Pro | Ser |
| | | | | 35 | | | | | 40 | | | | | 45 |
| Glu | Gly | Leu | Tyr | Leu | Ile | Tyr | Ser | Gln | Val | Leu | Phe | Lys | Gly | Gln |
| | | | | 50 | | | | | 55 | | | | | 60 |
| Gly | Cys | Pro | Ser | Thr | His | Val | Leu | Leu | Thr | His | Thr | Ile | Ser | Arg |
| | | | | 65 | | | | | 70 | | | | | 75 |
| Ile | Ala | Val | Ser | Tyr | Gln | Thr | Lys | Val | Asn | Leu | Leu | Ser | Ala | Ile |
| | | | | 80 | | | | | 85 | | | | | 90 |
| Lys | Ser | Pro | Cys | Gln | Arg | Glu | Thr | Pro | Glu | Gly | Ala | Glu | Ala | Lys |
| | | | | 95 | | | | | 100 | | | | | 105 |
| Pro | Trp | Tyr | Glu | Pro | Ile | Tyr | Leu | Gly | Gly | Val | Phe | Gln | Leu | Glu |
| | | | | 110 | | | | | 115 | | | | | 120 |
| Lys | Gly | Asp | Arg | Leu | Ser | Ala | Glu | Ile | Asn | Arg | Pro | Asp | Tyr | Leu |
| | | | | 125 | | | | | 130 | | | | | 135 |
| Asp | Phe | Ala | Glu | Ser | Gly | Gln | Val | Tyr | Phe | Gly | Ile | Ile | Ala | Phe |
| | | | | 140 | | | | | 145 | | | | | 150 |

(2) INFORMATION FOR SEQ ID NO:6:

(i) SEQUENCE CHARACTERISTICS:
(A) LENGTH: 150 amino acids
(B) TYPE: amino acid
(C) STRANDEDNESS: single
(D) TOPOLOGY: linear (ix) FEATURE:
(A) NAME/KEY:
(B) LOCATION:
(C) IDENTIFICATION METHOD:
(D) OTHER INFORMATION:

(xi) SEQUENCE DESCRIPTION: SEQ ID NO:6:

| Arg | Lys | Arg | Lys | Pro | Val | Ala | His | Val | Val | Ala | Asn | Pro | Gln | Ala |
|---|---|---|---|---|---|---|---|---|---|---|---|---|---|---|
| 1 | | | | 5 | | | | | 10 | | | | | 15 |
| Glu | Gly | Gln | Leu | Gln | Trp | Leu | Asn | Arg | Arg | Ala | Asn | Ala | Leu | Leu |
| | | | | 20 | | | | | 25 | | | | | 30 |
| Ala | Asn | Gly | Val | Glu | Leu | Arg | Asp | Asn | Gln | Leu | Val | Val | Pro | Ser |
| | | | | 35 | | | | | 40 | | | | | 45 |
| Glu | Gly | Leu | Tyr | Leu | Ile | Tyr | Ser | Gln | Val | Leu | Phe | Lys | Gly | Gln |
| | | | | 50 | | | | | 55 | | | | | 60 |
| Gly | Cys | Pro | Ser | Thr | His | Val | Leu | Leu | Thr | His | Thr | Ile | Ser | Arg |
| | | | | 65 | | | | | 70 | | | | | 75 |
| Ile | Ala | Val | Ser | Tyr | Gln | Thr | Lys | Val | Asn | Leu | Leu | Ser | Ala | Ile |
| | | | | 80 | | | | | 85 | | | | | 90 |
| Lys | Ser | Pro | Cys | Gln | Arg | Glu | Thr | Pro | Glu | Gly | Ala | Glu | Ala | Lys |
| | | | | 95 | | | | | 100 | | | | | 105 |
| Pro | Trp | Tyr | Glu | Pro | Ile | Tyr | Leu | Gly | Gly | Val | Phe | Gln | Leu | Glu |
| | | | | 110 | | | | | 115 | | | | | 120 |
| Lys | Gly | Asp | Arg | Leu | Ser | Ala | Glu | Ile | Asn | Arg | Pro | Asp | Tyr | Leu |
| | | | | 125 | | | | | 130 | | | | | 135 |
| Asp | Phe | Ala | Glu | Ser | Gly | Gln | Val | Tyr | Phe | Gly | Ile | Ile | Ala | Trp |
| | | | | 140 | | | | | 145 | | | | | 150 |

( 2 ) INFORMATION FOR SEQ ID NO:7:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:7:

```
Arg Lys Arg Lys Pro Val Ala His Val Val Ala Asn Pro Gln Ala
 1               5                  10                  15

Glu Gly Gln Leu Gln Trp Leu Asn Arg Arg Ala Asn Ala Leu Leu
                20                  25                  30

Ala Asn Gly Val Glu Leu Arg Asp Asn Gln Leu Val Val Pro Ser
                35                  40                  45

Glu Gly Leu Tyr Leu Ile Tyr Ser Gln Val Leu Phe Lys Gly Gln
                50                  55                  60

Gly Cys Pro Ser Thr His Val Leu Leu Thr His Thr Ile Ser Arg
                65                  70                  75

Ile Ala Val Ser Tyr Gln Thr Lys Val Asn Leu Leu Ser Ala Ile
                80                  85                  90

Lys Ser Pro Cys Gln Arg Glu Thr Pro Glu Gly Ala Glu Ala Lys
                95                 100                 105

Pro Trp Tyr Glu Pro Ile Tyr Leu Gly Gly Val Phe Gln Leu Glu
               110                 115                 120

Lys Gly Asp Arg Leu Ser Ala Glu Ile Asn Arg Pro Asp Tyr Leu
               125                 130                 135

Asp Phe Ala Glu Ser Gly Gln Val Tyr Phe Gly Ile Ile Ala Leu
               140                 145                 150

Phe
```

( 2 ) INFORMATION FOR SEQ ID NO:8:

( i ) SEQUENCE CHARACTERISTICS:
        ( A ) LENGTH: 150 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:8:

```
Arg Lys Arg Lys Pro Val Ala His Val Val Ala Asn Pro Gln Ala
 1               5                  10                  15

Glu Gly Gln Leu Gln Trp Leu Asn Arg Arg Ala Asn Ala Leu Leu
                20                  25                  30

Ala Asn Gly Val Glu Leu Arg Asp Asn Gln Leu Val Val Pro Ser
                35                  40                  45

Glu Gly Leu Tyr Leu Ile Tyr Ser Gln Val Leu Phe Lys Gly Gln
                50                  55                  60

Gly Cys Pro Ser Thr His Val Leu Leu Thr His Thr Ile Ser Arg
                65                  70                  75
```

```
Ile Ala Val Ser Tyr Gln Thr Lys Val Asn Leu Leu Ser Ala Ile
                80                      85                      90

Lys Ser Pro Cys Gln Arg Glu Thr Pro Glu Gly Ala Glu Ala Lys
                95                     100                     105

Pro Trp Tyr Glu Pro Ile Tyr Leu Gly Gly Val Phe Gln Leu Glu
               110                     115                     120

Lys Gly Asp Arg Leu Ser Ala Glu Ile Asn Arg Pro Asp Tyr Leu
               125                     130                     135

Asp Phe Ala Glu Ser Gly Gln Val Tyr Phe Gly Ile Ile Trp Leu
               140                     145                     150
```

( 2 ) INFORMATION FOR SEQ ID NO:9:

( i ) SEQUENCE CHARACTERISTICS:
        ( A ) LENGTH: 150 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:9:

```
Arg Lys Arg Lys Pro Val Ala His Val Val Ala Asn Pro Gln Ala
 1               5                      10                      15

Glu Gly Gln Leu Gln Trp Leu Asn Arg Arg Ala Asn Ala Leu Leu
                20                      25                      30

Ala Asn Gly Val Glu Leu Arg Asp Asn Gln Leu Val Val Pro Ser
                35                      40                      45

Glu Gly Leu Tyr Leu Ile Tyr Ser Gln Val Leu Phe Lys Gly Gln
                50                      55                      60

Gly Cys Pro Ser Thr His Val Leu Leu Thr His Thr Ile Ser Arg
                65                      70                      75

Ile Ala Val Ser Tyr Gln Thr Lys Val Asn Leu Leu Ser Ala Ile
                80                      85                      90

Lys Ser Pro Cys Gln Arg Glu Thr Pro Glu Gly Ala Glu Ala Lys
                95                     100                     105

Pro Trp Tyr Glu Pro Ile Tyr Leu Gly Gly Val Phe Gln Leu Glu
               110                     115                     120

Lys Gly Asp Arg Leu Ser Ala Glu Ile Asn Arg Pro Asp Tyr Leu
               125                     130                     135

Asp Phe Ala Glu Ser Gly Gln Val Tyr Phe Gly Ile Ile Phe Leu
               140                     145                     150
```

( 2 ) INFORMATION FOR SEQ ID NO:10:

( i ) SEQUENCE CHARACTERISTICS:
        ( A ) LENGTH: 150 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:10:

```
Arg Lys Arg Lys Pro Val Ala His Val Val Ala Asn Pro Gln Ala
 1               5                      10                      15
```

```
Glu Gly Gln Leu Gln Trp Leu Asn Arg Arg Ala Asn Ala Leu Leu
                 20                  25                  30

Ala Asn Gly Val Glu Leu Arg Asp Asn Gln Leu Val Val Pro Ser
                 35                  40                  45

Glu Gly Leu Tyr Leu Ile Tyr Ser Gln Val Leu Phe Lys Gly Gln
                 50                  55                  60

Gly Cys Pro Ser Thr His Val Leu Leu Thr His Thr Ile Ser Arg
                 65                  70                  75

Ile Ala Val Ser Tyr Gln Thr Lys Val Asn Leu Leu Ser Ala Ile
                 80                  85                  90

Lys Ser Pro Cys Gln Arg Glu Thr Pro Glu Gly Ala Glu Ala Lys
                 95                 100                 105

Pro Trp Tyr Glu Pro Ile Tyr Leu Gly Gly Val Phe Gln Leu Glu
                110                 115                 120

Lys Gly Asp Arg Leu Ser Ala Glu Ile Asn Arg Pro Asp Tyr Leu
                125                 130                 135

Asp Phe Ala Glu Ser Gly Gln Val Tyr Phe Gly Ile Ile Phe Phe
                140                 145                 150
```

( 2 ) INFORMATION FOR SEQ ID NO:11:

( i ) SEQUENCE CHARACTERISTICS:
    ( A ) LENGTH: 150 amino acids
    ( B ) TYPE: amino acid
    ( C ) STRANDEDNESS: single
    ( D ) TOPOLOGY: linear ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO:11:

```
Arg Lys Arg Lys Pro Val Ala His Val Val Ala Asn Pro Gln Ala
 1               5                  10                  15

Glu Gly Gln Leu Gln Trp Leu Asn Arg Arg Ala Asn Ala Leu Leu
                 20                  25                  30

Ala Asn Gly Val Glu Leu Arg Asp Asn Gln Leu Val Val Pro Ser
                 35                  40                  45

Glu Gly Leu Tyr Leu Ile Tyr Ser Gln Val Leu Phe Lys Gly Gln
                 50                  55                  60

Gly Cys Pro Ser Thr His Val Leu Leu Thr His Thr Ile Ser Arg
                 65                  70                  75

Ile Ala Val Ser Tyr Gln Thr Lys Val Asn Leu Leu Ser Ala Ile
                 80                  85                  90

Lys Ser Pro Cys Gln Arg Glu Thr Pro Glu Gly Ala Glu Ala Lys
                 95                 100                 105

Pro Trp Tyr Glu Pro Ile Tyr Leu Gly Gly Val Phe Gln Leu Glu
                110                 115                 120

Lys Gly Asp Arg Leu Ser Ala Glu Ile Asn Arg Pro Asp Tyr Leu
                125                 130                 135

Asp Phe Ala Glu Ser Gly Gln Val Tyr Phe Gly Ile Ile Trp Phe
                140                 145                 150
```

( 2 ) INFORMATION FOR SEQ ID NO:12:

( i ) SEQUENCE CHARACTERISTICS:
    ( A ) LENGTH: 150 amino acids
    ( B ) TYPE: amino acid
    ( C ) STRANDEDNESS: single
    ( D ) TOPOLOGY: linear (i x) FEATURE:
    (A) NAME/KEY:
    (B) LOCATION:
    (C) IDENTIFICATION METHOD:
    (D) OTHER INFORMATION:

(x i) SEQUENCE DESCRIPTION: SEQ ID NO:12:

| Arg | Lys | Arg | Lys | Pro | Val | Ala | His | Val | Val | Ala | Asn | Pro | Gln | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Glu | Gly | Gln | Leu | Gln | Trp | Leu | Asn | Arg | Arg | Ala | Asn | Ala | Leu | Leu |
|     |     |     |     | 20  |     |     |     |     | 25  |     |     |     |     | 30  |
| Ala | Asn | Gly | Val | Glu | Leu | Arg | Asp | Asn | Gln | Leu | Val | Val | Pro | Ser |
|     |     |     |     | 35  |     |     |     |     | 40  |     |     |     |     | 45  |
| Glu | Gly | Leu | Tyr | Leu | Ile | Tyr | Ser | Gln | Val | Leu | Phe | Lys | Gly | Gln |
|     |     |     |     | 50  |     |     |     |     | 55  |     |     |     |     | 60  |
| Gly | Cys | Pro | Ser | Thr | His | Val | Leu | Leu | Thr | His | Thr | Ile | Ser | Arg |
|     |     |     |     | 65  |     |     |     |     | 70  |     |     |     |     | 75  |
| Ile | Ala | Val | Ser | Tyr | Gln | Thr | Lys | Val | Asn | Leu | Leu | Ser | Ala | Ile |
|     |     |     |     | 80  |     |     |     |     | 85  |     |     |     |     | 90  |
| Lys | Ser | Pro | Cys | Gln | Arg | Glu | Thr | Pro | Glu | Gly | Ala | Glu | Ala | Lys |
|     |     |     |     | 95  |     |     |     |     | 100 |     |     |     |     | 105 |
| Pro | Trp | Tyr | Glu | Pro | Ile | Tyr | Leu | Gly | Gly | Val | Phe | Gln | Leu | Glu |
|     |     |     |     | 110 |     |     |     |     | 115 |     |     |     |     | 120 |
| Lys | Gly | Asp | Arg | Leu | Ser | Ala | Glu | Ile | Asn | Arg | Pro | Asp | Tyr | Leu |
|     |     |     |     | 125 |     |     |     |     | 130 |     |     |     |     | 135 |
| Asp | Phe | Ala | Glu | Ser | Gly | Gln | Val | Tyr | Phe | Gly | Ile | Phe | Ala | Leu |
|     |     |     |     | 140 |     |     |     |     | 145 |     |     |     |     | 150 |

(2) INFORMATION FOR SEQ ID NO:13:

(i) SEQUENCE CHARACTERISTICS:
       (A) LENGTH: 150 amino acids
       (B) TYPE: amino acid
       (C) STRANDEDNESS: single
       (D) TOPOLOGY: linear (i x) FEATURE:
       (A) NAME/KEY:
       (B) LOCATION:
       (C) IDENTIFICATION METHOD:
       (D) OTHER INFORMATION:

(x i) SEQUENCE DESCRIPTION: SEQ ID NO:13:

| Arg | Lys | Arg | Lys | Pro | Val | Ala | His | Val | Val | Ala | Asn | Pro | Gln | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Glu | Gly | Gln | Leu | Gln | Trp | Leu | Asn | Arg | Arg | Ala | Asn | Ala | Leu | Leu |
|     |     |     |     | 20  |     |     |     |     | 25  |     |     |     |     | 30  |
| Ala | Asn | Gly | Val | Glu | Leu | Arg | Asp | Asn | Gln | Leu | Val | Val | Pro | Ser |
|     |     |     |     | 35  |     |     |     |     | 40  |     |     |     |     | 45  |
| Glu | Gly | Leu | Tyr | Leu | Ile | Tyr | Ser | Gln | Val | Leu | Phe | Lys | Gly | Gln |
|     |     |     |     | 50  |     |     |     |     | 55  |     |     |     |     | 60  |
| Gly | Cys | Pro | Ser | Thr | His | Val | Leu | Leu | Thr | His | Thr | Ile | Ser | Arg |
|     |     |     |     | 65  |     |     |     |     | 70  |     |     |     |     | 75  |
| Ile | Ala | Val | Ser | Tyr | Gln | Thr | Lys | Val | Asn | Leu | Leu | Ser | Ala | Ile |
|     |     |     |     | 80  |     |     |     |     | 85  |     |     |     |     | 90  |
| Lys | Ser | Pro | Cys | Gln | Arg | Glu | Thr | Pro | Glu | Gly | Ala | Glu | Ala | Lys |
|     |     |     |     | 95  |     |     |     |     | 100 |     |     |     |     | 105 |
| Pro | Trp | Tyr | Glu | Pro | Ile | Tyr | Leu | Gly | Gly | Val | Phe | Gln | Leu | Glu |
|     |     |     |     | 110 |     |     |     |     | 115 |     |     |     |     | 120 |
| Lys | Gly | Asp | Arg | Leu | Ser | Ala | Glu | Ile | Asn | Arg | Pro | Asp | Tyr | Leu |
|     |     |     |     | 125 |     |     |     |     | 130 |     |     |     |     | 135 |

```
Asp  Phe  Ala  Glu  Ser  Gly  Gln  Val  Tyr  Phe  Gly  Phe  Ile  Ala  Leu
                    140                 145                           150
```

( 2 ) INFORMATION FOR SEQ ID NO:14:

( i ) SEQUENCE CHARACTERISTICS:
        ( A ) LENGTH: 150 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:14:

```
Arg  Lys  Arg  Lys  Pro  Val  Ala  His  Val  Val  Ala  Asn  Pro  Gln  Ala
 1                   5                       10                         15

Glu  Gly  Gln  Leu  Gln  Trp  Leu  Asn  Arg  Arg  Ala  Asn  Ala  Leu  Leu
                    20                       25                         30

Ala  Asn  Gly  Val  Glu  Leu  Arg  Asp  Asn  Gln  Leu  Val  Val  Pro  Ser
                    35                       40                         45

Glu  Gly  Leu  Tyr  Leu  Ile  Tyr  Ser  Gln  Val  Leu  Phe  Lys  Gly  Gln
                    50                       55                         60

Gly  Cys  Pro  Ser  Thr  His  Val  Leu  Leu  Thr  His  Thr  Ile  Ser  Arg
                    65                       70                         75

Ile  Ala  Val  Ser  Tyr  Gln  Thr  Lys  Val  Asn  Leu  Leu  Ser  Ala  Ile
                    80                       85                         90

Lys  Ser  Pro  Cys  Gln  Arg  Glu  Thr  Pro  Glu  Gly  Ala  Glu  Ala  Lys
                    95                       100                        105

Pro  Trp  Tyr  Glu  Pro  Ile  Tyr  Leu  Gly  Gly  Val  Phe  Gln  Leu  Glu
                    110                      115                        120

Lys  Gly  Asp  Arg  Leu  Ser  Ala  Glu  Ile  Asn  Arg  Pro  Asp  Tyr  Leu
                    125                      130                        135

Asp  Phe  Ala  Glu  Ser  Gly  Gln  Val  Tyr  Phe  Gly  Ile  Ile  Ala  Leu
                    140                      145                        150
```

( 2 ) INFORMATION FOR SEQ ID NO:15:

( i ) SEQUENCE CHARACTERISTICS:
        ( A ) LENGTH: 148 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:15:

```
Met  Lys  Pro  Val  Ala  His  Val  Val  Ala  Asn  Pro  Gln  Ala  Glu  Gly
 1                   5                       10                         15

Gln  Leu  Gln  Trp  Leu  Asn  Arg  Arg  Ala  Asn  Ala  Leu  Leu  Ala  Asn
                    20                       25                         30

Gly  Val  Glu  Leu  Arg  Asp  Asn  Gln  Leu  Val  Val  Pro  Ser  Glu  Gly
                    35                       40                         45

Leu  Tyr  Leu  Ile  Tyr  Ser  Gln  Val  Leu  Phe  Lys  Gly  Gln  Gly  Cys
                    50                       55                         60

Pro  Ser  Thr  His  Val  Leu  Leu  Thr  His  Thr  Ile  Ser  Arg  Ile  Ala
                    65                       70                         75
```

Val Ser Tyr Gln Thr Lys Val Asn Leu Leu Ser Ala Ile Lys Ser
              80                  85                  90

Pro Cys Gln Arg Glu Thr Pro Glu Gly Ala Glu Ala Lys Pro Trp
              95                 100                 105

Tyr Glu Pro Ile Tyr Leu Gly Gly Val Phe Gln Leu Glu Lys Gly
             110                 115                 120

Asp Arg Leu Ser Ala Glu Ile Asn Arg Pro Asp Tyr Leu Asp Phe
             125                 130                 135

Ala Glu Ser Gly Gln Val Tyr Phe Gly Ile Ile Ala Phe
             140                 145

( 2 ) INFORMATION FOR SEQ ID NO:16:

( i ) SEQUENCE CHARACTERISTICS:
        ( A ) LENGTH: 149 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:16:

Met Asp Lys Pro Val Ala His Val Val Ala Asn Pro Gln Ala Glu
 1               5                  10                  15

Gly Gln Leu Gln Trp Leu Asn Arg Arg Ala Asn Ala Leu Leu Ala
              20                  25                  30

Asn Gly Val Glu Leu Arg Asp Asn Gln Leu Val Val Pro Ser Glu
              35                  40                  45

Gly Leu Tyr Leu Ile Tyr Ser Gln Val Leu Phe Lys Gly Gln Gly
              50                  55                  60

Cys Pro Ser Thr His Val Leu Leu Thr His Thr Ile Ser Arg Ile
              65                  70                  75

Ala Val Ser Tyr Gln Thr Lys Val Asn Leu Leu Ser Ala Ile Lys
              80                  85                  90

Ser Pro Cys Gln Arg Glu Thr Pro Glu Gly Ala Glu Ala Lys Pro
              95                 100                 105

Trp Tyr Glu Pro Ile Tyr Leu Gly Gly Val Phe Gln Leu Glu Lys
             110                 115                 120

Gly Asp Arg Leu Ser Ala Glu Ile Asn Arg Pro Asp Tyr Leu Asp
             125                 130                 135

Phe Ala Glu Ser Gly Gln Val Tyr Phe Gly Ile Ile Ala Phe
             140                 145

( 2 ) INFORMATION FOR SEQ ID NO:17:

( i ) SEQUENCE CHARACTERISTICS:
        ( A ) LENGTH: 150 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:17:

Met Ser Asp Lys Pro Val Ala His Val Val Ala Asn Pro Gln Ala
 1               5                  10                  15

| | | | | | | | | | | | | | | |
|---|---|---|---|---|---|---|---|---|---|---|---|---|---|---|
|Glu|Gly|Gln|Leu|Gln|Trp|Leu|Asn|Arg|Arg|Ala|Asn|Ala|Leu|Leu|
| | | | |20| | | |25| | | | | |30|
|Ala|Asn|Gly|Val|Glu|Leu|Arg|Asp|Asn|Gln|Leu|Val|Val|Pro|Ser|
| | | | |35| | | |40| | | | | |45|
|Glu|Gly|Leu|Tyr|Leu|Ile|Tyr|Ser|Gln|Val|Leu|Phe|Lys|Gly|Gln|
| | | | |50| | | |55| | | | | |60|
|Gly|Cys|Pro|Ser|Thr|His|Val|Leu|Leu|Thr|His|Thr|Ile|Ser|Arg|
| | | | |65| | | |70| | | | | |75|
|Ile|Ala|Val|Ser|Tyr|Gln|Thr|Lys|Val|Asn|Leu|Leu|Ser|Ala|Ile|
| | | | |80| | | |85| | | | | |90|
|Lys|Ser|Pro|Cys|Gln|Arg|Glu|Thr|Pro|Glu|Gly|Ala|Glu|Ala|Lys|
| | | | |95| | | |100| | | | | |105|
|Pro|Trp|Tyr|Glu|Pro|Ile|Tyr|Leu|Gly|Gly|Val|Phe|Gln|Leu|Glu|
| | | | |110| | | |115| | | | | |120|
|Lys|Gly|Asp|Arg|Leu|Ser|Ala|Glu|Ile|Asn|Arg|Pro|Asp|Tyr|Leu|
| | | | |125| | | |130| | | | | |135|
|Asp|Phe|Ala|Glu|Ser|Gly|Gln|Val|Tyr|Phe|Gly|Ile|Ile|Ala|Phe|
| | | | |140| | | |145| | | | | |150|

( 2 ) INFORMATION FOR SEQ ID NO:18:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:18:

| | | | | | | | | | | | | | | |
|---|---|---|---|---|---|---|---|---|---|---|---|---|---|---|
|Met|Pro|Ser|Asp|Lys|Pro|Val|Ala|His|Val|Ala|Asn|Pro|Gln|
|1| | | |5| | | |10| | | | | |15|
|Ala|Glu|Gly|Gln|Leu|Gln|Trp|Leu|Asn|Arg|Arg|Ala|Asn|Ala|Leu|
| | | | |20| | | |25| | | | | |30|
|Leu|Ala|Asn|Gly|Val|Glu|Leu|Arg|Asp|Asn|Gln|Leu|Val|Val|Pro|
| | | | |35| | | |40| | | | | |45|
|Ser|Glu|Gly|Leu|Tyr|Leu|Ile|Tyr|Ser|Gln|Val|Leu|Phe|Lys|Gly|
| | | | |50| | | |55| | | | | |60|
|Gln|Gly|Cys|Pro|Ser|Thr|His|Val|Leu|Leu|Thr|His|Thr|Ile|Ser|
| | | | |65| | | |70| | | | | |75|
|Arg|Ile|Ala|Val|Ser|Tyr|Gln|Thr|Lys|Val|Asn|Leu|Leu|Ser|Ala|
| | | | |80| | | |85| | | | | |90|
|Ile|Lys|Ser|Pro|Cys|Gln|Arg|Glu|Thr|Pro|Glu|Gly|Ala|Glu|Ala|
| | | | |95| | | |100| | | | | |105|
|Lys|Pro|Trp|Tyr|Glu|Pro|Ile|Tyr|Leu|Gly|Gly|Val|Phe|Gln|Leu|
| | | | |110| | | |115| | | | | |120|
|Glu|Lys|Gly|Asp|Arg|Leu|Ser|Ala|Glu|Ile|Asn|Arg|Pro|Asp|Tyr|
| | | | |125| | | |130| | | | | |135|
|Leu|Asp|Phe|Ala|Glu|Ser|Gly|Gln|Val|Tyr|Phe|Gly|Ile|Ile|Ala|
| | | | |140| | | |145| | | | | |150|

Phe ( 2 ) INFORMATION FOR SEQ ID NO:19:

( i ) SEQUENCE CHARACTERISTICS:
        ( A ) LENGTH: 151 amino acids (B) TYPE: amino acid
(C) STRANDEDNESS: single
(D) TOPOLOGY: linear (ix) FEATURE:
(A) NAME/KEY:
(B) LOCATION:
(C) IDENTIFICATION METHOD:
(D) OTHER INFORMATION:

(xi) SEQUENCE DESCRIPTION: SEQ ID NO:19:

| Met | Arg | Lys | Arg | Lys | Pro | Val | Ala | His | Val | Val | Ala | Asn | Pro | Gln |
|---|---|---|---|---|---|---|---|---|---|---|---|---|---|---|
| 1 | | | | 5 | | | | | 10 | | | | | 15 |

| Ala | Glu | Gly | Gln | Leu | Gln | Trp | Leu | Asn | Arg | Arg | Ala | Asn | Ala | Leu |
|---|---|---|---|---|---|---|---|---|---|---|---|---|---|---|
| | | | | 20 | | | | | 25 | | | | | 30 |

| Leu | Ala | Asn | Gly | Val | Glu | Leu | Arg | Asp | Asn | Gln | Leu | Val | Val | Pro |
|---|---|---|---|---|---|---|---|---|---|---|---|---|---|---|
| | | | | 35 | | | | | 40 | | | | | 45 |

| Ser | Glu | Gly | Leu | Tyr | Leu | Ile | Tyr | Ser | Gln | Val | Leu | Phe | Lys | Gly |
|---|---|---|---|---|---|---|---|---|---|---|---|---|---|---|
| | | | | 50 | | | | | 55 | | | | | 60 |

| Gln | Gly | Cys | Pro | Ser | Thr | His | Val | Leu | Leu | Thr | His | Thr | Ile | Ser |
|---|---|---|---|---|---|---|---|---|---|---|---|---|---|---|
| | | | | 65 | | | | | 70 | | | | | 75 |

| Arg | Ile | Ala | Val | Ser | Tyr | Gln | Thr | Lys | Val | Asn | Leu | Leu | Ser | Ala |
|---|---|---|---|---|---|---|---|---|---|---|---|---|---|---|
| | | | | 80 | | | | | 85 | | | | | 90 |

| Ile | Lys | Ser | Pro | Cys | Gln | Arg | Glu | Thr | Pro | Glu | Gly | Ala | Glu | Ala |
|---|---|---|---|---|---|---|---|---|---|---|---|---|---|---|
| | | | | 95 | | | | | 100 | | | | | 105 |

| Lys | Pro | Trp | Tyr | Glu | Pro | Ile | Tyr | Leu | Gly | Gly | Val | Phe | Gln | Leu |
|---|---|---|---|---|---|---|---|---|---|---|---|---|---|---|
| | | | | 110 | | | | | 115 | | | | | 120 |

| Glu | Lys | Gly | Asp | Arg | Leu | Ser | Ala | Glu | Ile | Asn | Arg | Pro | Asp | Tyr |
|---|---|---|---|---|---|---|---|---|---|---|---|---|---|---|
| | | | | 125 | | | | | 130 | | | | | 135 |

| Leu | Asp | Phe | Ala | Glu | Ser | Gly | Gln | Val | Tyr | Phe | Gly | Ile | Ile | Ala |
|---|---|---|---|---|---|---|---|---|---|---|---|---|---|---|
| | | | | 140 | | | | | 145 | | | | | 150 |

Phe (2) INFORMATION FOR SEQ ID NO:20:

(i) SEQUENCE CHARACTERISTICS:
(A) LENGTH: 151 amino acids
(B) TYPE: amino acid
(C) STRANDEDNESS: single
(D) TOPOLOGY: linear (ix) FEATURE:
(A) NAME/KEY:
(B) LOCATION:
(C) IDENTIFICATION METHOD:
(D) OTHER INFORMATION:

(xi) SEQUENCE DESCRIPTION: SEQ ID NO:20:

| Met | Arg | Lys | Arg | Lys | Pro | Val | Ala | His | Val | Val | Ala | Asn | Pro | Gln |
|---|---|---|---|---|---|---|---|---|---|---|---|---|---|---|
| 1 | | | | 5 | | | | | 10 | | | | | 15 |

| Ala | Glu | Gly | Gln | Leu | Gln | Trp | Leu | Asn | Arg | Arg | Ala | Asn | Ala | Leu |
|---|---|---|---|---|---|---|---|---|---|---|---|---|---|---|
| | | | | 20 | | | | | 25 | | | | | 30 |

| Leu | Ala | Asn | Gly | Val | Glu | Leu | Arg | Asp | Asn | Gln | Leu | Val | Val | Pro |
|---|---|---|---|---|---|---|---|---|---|---|---|---|---|---|
| | | | | 35 | | | | | 40 | | | | | 45 |

| Ser | Glu | Gly | Leu | Tyr | Leu | Ile | Tyr | Ser | Gln | Val | Leu | Phe | Lys | Gly |
|---|---|---|---|---|---|---|---|---|---|---|---|---|---|---|
| | | | | 50 | | | | | 55 | | | | | 60 |

| Gln | Gly | Cys | Pro | Ser | Thr | His | Val | Leu | Leu | Thr | His | Thr | Ile | Ser |
|---|---|---|---|---|---|---|---|---|---|---|---|---|---|---|
| | | | | 65 | | | | | 70 | | | | | 75 |

| Arg | Ile | Ala | Val | Ser | Tyr | Gln | Thr | Lys | Val | Asn | Leu | Leu | Ser | Ala |
|---|---|---|---|---|---|---|---|---|---|---|---|---|---|---|
| | | | | 80 | | | | | 85 | | | | | 90 |

| Ile | Lys | Ser | Pro | Cys | Gln | Arg | Glu | Thr | Pro | Glu | Gly | Ala | Glu | Ala |
|---|---|---|---|---|---|---|---|---|---|---|---|---|---|---|
| | | | | 95 | | | | | 100 | | | | | 105 |

```
Lys Pro Trp Tyr Glu Pro Ile Tyr Leu Gly Gly Val Phe Gln Leu
            110                 115                 120

Glu Lys Gly Asp Arg Leu Ser Ala Glu Ile Asn Arg Pro Asp Tyr
            125                 130                 135

Leu Asp Phe Ala Glu Ser Gly Gln Val Tyr Phe Gly Ile Ile Ala
            140                 145                 150

Trp
```

( 2 ) INFORMATION FOR SEQ ID NO:21:

( i ) SEQUENCE CHARACTERISTICS:
        ( A ) LENGTH: 152 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:21:

```
Met Arg Lys Arg Lys Pro Val Ala His Val Ala Asn Pro Gln
 1              5                  10                  15

Ala Glu Gly Gln Leu Gln Trp Leu Asn Arg Arg Ala Asn Ala Leu
            20                  25                  30

Leu Ala Asn Gly Val Glu Leu Arg Asp Asn Gln Leu Val Val Pro
            35                  40                  45

Ser Glu Gly Leu Tyr Leu Ile Tyr Ser Gln Val Leu Phe Lys Gly
            50                  55                  60

Gln Gly Cys Pro Ser Thr His Val Leu Leu Thr His Thr Ile Ser
            65                  70                  75

Arg Ile Ala Val Ser Tyr Gln Thr Lys Val Asn Leu Leu Ser Ala
            80                  85                  90

Ile Lys Ser Pro Cys Gln Arg Glu Thr Pro Glu Gly Ala Glu Ala
            95                  100                 105

Lys Pro Trp Tyr Glu Pro Ile Tyr Leu Gly Gly Val Phe Gln Leu
            110                 115                 120

Glu Lys Gly Asp Arg Leu Ser Ala Glu Ile Asn Arg Pro Asp Tyr
            125                 130                 135

Leu Asp Phe Ala Glu Ser Gly Gln Val Tyr Phe Gly Ile Ile Ala
            140                 145                 150

Leu Phe
```

( 2 ) INFORMATION FOR SEQ ID NO:22:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:22:

```
Met Arg Lys Arg Lys Pro Val Ala His Val Ala Asn Pro Gln
 1              5                  10                  15

Ala Glu Gly Gln Leu Gln Trp Leu Asn Arg Arg Ala Asn Ala Leu
            20                  25                  30
```

```
Leu Ala Asn Gly Val Glu Leu Arg Asp Asn Gln Leu Val Val Pro
                35                  40                  45

Ser Glu Gly Leu Tyr Leu Ile Tyr Ser Gln Val Leu Phe Lys Gly
                50                  55                  60

Gln Gly Cys Pro Ser Thr His Val Leu Leu Thr His Thr Ile Ser
                65                  70                  75

Arg Ile Ala Val Ser Tyr Gln Thr Lys Val Asn Leu Leu Ser Ala
                80                  85                  90

Ile Lys Ser Pro Cys Gln Arg Glu Thr Pro Glu Gly Ala Glu Ala
                95                 100                 105

Lys Pro Trp Tyr Glu Pro Ile Tyr Leu Gly Gly Val Phe Gln Leu
               110                 115                 120

Glu Lys Gly Asp Arg Leu Ser Ala Glu Ile Asn Arg Pro Asp Tyr
               125                 130                 135

Leu Asp Phe Ala Glu Ser Gly Gln Val Tyr Phe Gly Ile Ile Trp
               140                 145                 150

Leu
```

(2) INFORMATION FOR SEQ ID NO:23:

(i) SEQUENCE CHARACTERISTICS:
        (A) LENGTH: 151 amino acids
        (B) TYPE: amino acid
        (C) STRANDEDNESS: single
        (D) TOPOLOGY: linear (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO:23:

```
Met Arg Lys Arg Lys Pro Val Ala His Val Val Ala Asn Pro Gln
 1               5                  10                  15

Ala Glu Gly Gln Leu Gln Trp Leu Asn Arg Arg Ala Asn Ala Leu
                20                  25                  30

Leu Ala Asn Gly Val Glu Leu Arg Asp Asn Gln Leu Val Val Pro
                35                  40                  45

Ser Glu Gly Leu Tyr Leu Ile Tyr Ser Gln Val Leu Phe Lys Gly
                50                  55                  60

Gln Gly Cys Pro Ser Thr His Val Leu Leu Thr His Thr Ile Ser
                65                  70                  75

Arg Ile Ala Val Ser Tyr Gln Thr Lys Val Asn Leu Leu Ser Ala
                80                  85                  90

Ile Lys Ser Pro Cys Gln Arg Glu Thr Pro Glu Gly Ala Glu Ala
                95                 100                 105

Lys Pro Trp Tyr Glu Pro Ile Tyr Leu Gly Gly Val Phe Gln Leu
               110                 115                 120

Glu Lys Gly Asp Arg Leu Ser Ala Glu Ile Asn Arg Pro Asp Tyr
               125                 130                 135

Leu Asp Phe Ala Glu Ser Gly Gln Val Tyr Phe Gly Ile Ile Phe
               140                 145                 150

Leu
```

(2) INFORMATION FOR SEQ ID NO:24:

(i) SEQUENCE CHARACTERISTICS:
        (A) LENGTH: 151 amino acids
        (B) TYPE: amino acid ( C ) STRANDEDNESS: single
( D ) TOPOLOGY: linear ( i x ) FEATURE:
   ( A ) NAME/KEY:
   ( B ) LOCATION:
   ( C ) IDENTIFICATION METHOD:
   ( D ) OTHER INFORMATION:

( x i ) SEQUENCE DESCRIPTION: SEQ ID NO:24:

```
Met Arg Lys Arg Lys Pro Val Ala His Val Val Ala Asn Pro Gln
 1               5                  10                  15

Ala Glu Gly Gln Leu Gln Trp Leu Asn Arg Arg Ala Asn Ala Leu
                20                  25                  30

Leu Ala Asn Gly Val Glu Leu Arg Asp Asn Gln Leu Val Val Pro
                35                  40                  45

Ser Glu Gly Leu Tyr Leu Ile Tyr Ser Gln Val Leu Phe Lys Gly
                50                  55                  60

Gln Gly Cys Pro Ser Thr His Val Leu Leu Thr His Thr Ile Ser
                65                  70                  75

Arg Ile Ala Val Ser Tyr Gln Thr Lys Val Asn Leu Leu Ser Ala
                80                  85                  90

Ile Lys Ser Pro Cys Gln Arg Glu Thr Pro Glu Gly Ala Glu Ala
                95                 100                 105

Lys Pro Trp Tyr Glu Pro Ile Tyr Leu Gly Gly Val Phe Gln Leu
               110                 115                 120

Glu Lys Gly Asp Arg Leu Ser Ala Glu Ile Asn Arg Pro Asp Tyr
               125                 130                 135

Leu Asp Phe Ala Glu Ser Gly Gln Val Tyr Phe Gly Ile Ile Phe
               140                 145                 150

Phe
```

( 2 ) INFORMATION FOR SEQ ID NO:25:

( i ) SEQUENCE CHARACTERISTICS:
      ( A ) LENGTH: 151 amino acids
      ( B ) TYPE: amino acid
      ( C ) STRANDEDNESS: single
      ( D ) TOPOLOGY: linear ( i x ) FEATURE:
      ( A ) NAME/KEY:
      ( B ) LOCATION:
      ( C ) IDENTIFICATION METHOD:
      ( D ) OTHER INFORMATION:

( x i ) SEQUENCE DESCRIPTION: SEQ ID NO:25:

```
Met Arg Lys Arg Lys Pro Val Ala His Val Val Ala Asn Pro Gln
 1               5                  10                  15

Ala Glu Gly Gln Leu Gln Trp Leu Asn Arg Arg Ala Asn Ala Leu
                20                  25                  30

Leu Ala Asn Gly Val Glu Leu Arg Asp Asn Gln Leu Val Val Pro
                35                  40                  45

Ser Glu Gly Leu Tyr Leu Ile Tyr Ser Gln Val Leu Phe Lys Gly
                50                  55                  60

Gln Gly Cys Pro Ser Thr His Val Leu Leu Thr His Thr Ile Ser
                65                  70                  75

Arg Ile Ala Val Ser Tyr Gln Thr Lys Val Asn Leu Leu Ser Ala
                80                  85                  90

Ile Lys Ser Pro Cys Gln Arg Glu Thr Pro Glu Gly Ala Glu Ala
                95                 100                 105

Lys Pro Trp Tyr Glu Pro Ile Tyr Leu Gly Gly Val Phe Gln Leu
```

|  | 110 |  |  |  |  | 115 |  |  |  |  | 120 |  |

Glu Lys Gly Asp Arg Leu Ser Ala Glu Ile Asn Arg Pro Asp Tyr
                    125                 130                 135

Leu Asp Phe Ala Glu Ser Gly Gln Val Tyr Phe Gly Ile Ile Trp
                140                 145                 150

Phe ( 2 ) INFORMATION FOR SEQ ID NO:26:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:26:

Met Arg Lys Arg Lys Pro Val Ala His Val Val Ala Asn Pro Gln
 1               5                  10                  15

Ala Glu Gly Gln Leu Gln Trp Leu Asn Arg Arg Ala Asn Ala Leu
                20                  25                  30

Leu Ala Asn Gly Val Glu Leu Arg Asp Asn Gln Leu Val Val Pro
                35                  40                  45

Ser Glu Gly Leu Tyr Leu Ile Tyr Ser Gln Val Leu Phe Lys Gly
                50                  55                  60

Gln Gly Cys Pro Ser Thr His Val Leu Leu Thr His Thr Ile Ser
                65                  70                  75

Arg Ile Ala Val Ser Tyr Gln Thr Lys Val Asn Leu Leu Ser Ala
                80                  85                  90

Ile Lys Ser Pro Cys Gln Arg Glu Thr Pro Glu Gly Ala Glu Ala
                95                 100                 105

Lys Pro Trp Tyr Glu Pro Ile Tyr Leu Gly Gly Val Phe Gln Leu
                110                 115                 120

Glu Lys Gly Asp Arg Leu Ser Ala Glu Ile Asn Arg Pro Asp Tyr
                125                 130                 135

Leu Asp Phe Ala Glu Ser Gly Gln Val Tyr Phe Gly Ile Phe Ala
                140                 145                 150

Leu ( 2 ) INFORMATION FOR SEQ ID NO:27:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:27:

Met Arg Lys Arg Lys Pro Val Ala His Val Val Ala Asn Pro Gln
 1               5                  10                  15

Ala Glu Gly Gln Leu Gln Trp Leu Asn Arg Arg Ala Asn Ala Leu
                20                  25                  30

```
Leu Ala Asn Gly Val Glu Leu Arg Asp Asn Gln Leu Val Val Pro
                 35                  40                  45

Ser Glu Gly Leu Tyr Leu Ile Tyr Ser Gln Val Leu Phe Lys Gly
                 50                  55                  60

Gln Gly Cys Pro Ser Thr His Val Leu Leu Thr His Thr Ile Ser
                 65                  70                  75

Arg Ile Ala Val Ser Tyr Gln Thr Lys Val Asn Leu Leu Ser Ala
                 80                  85                  90

Ile Lys Ser Pro Cys Gln Arg Glu Thr Pro Glu Gly Ala Glu Ala
                 95                 100                 105

Lys Pro Trp Tyr Glu Pro Ile Tyr Leu Gly Gly Val Phe Gln Leu
                110                 115                 120

Glu Lys Gly Asp Arg Leu Ser Ala Glu Ile Asn Arg Pro Asp Tyr
                125                 130                 135

Leu Asp Phe Ala Glu Ser Gly Gln Val Tyr Phe Gly Phe Ile Ala
                140                 145                 150

Leu
```

( 2 ) INFORMATION FOR SEQ ID NO:28:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:28:

```
Met Arg Lys Arg Lys Pro Val Ala His Val Val Ala Asn Pro Gln
 1               5                  10                  15

Ala Glu Gly Gln Leu Gln Trp Leu Asn Arg Arg Ala Asn Ala Leu
                 20                  25                  30

Leu Ala Asn Gly Val Glu Leu Arg Asp Asn Gln Leu Val Val Pro
                 35                  40                  45

Ser Glu Gly Leu Tyr Leu Ile Tyr Ser Gln Val Leu Phe Lys Gly
                 50                  55                  60

Gln Gly Cys Pro Ser Thr His Val Leu Leu Thr His Thr Ile Ser
                 65                  70                  75

Arg Ile Ala Val Ser Tyr Gln Thr Lys Val Asn Leu Leu Ser Ala
                 80                  85                  90

Ile Lys Ser Pro Cys Gln Arg Glu Thr Pro Glu Gly Ala Glu Ala
                 95                 100                 105

Lys Pro Trp Tyr Glu Pro Ile Tyr Leu Gly Gly Val Phe Gln Leu
                110                 115                 120

Glu Lys Gly Asp Arg Leu Ser Ala Glu Ile Asn Arg Pro Asp Tyr
                125                 130                 135

Leu Asp Phe Ala Glu Ser Gly Gln Val Tyr Phe Gly Ile Ile Ala
                140                 145                 150

Leu
```

( 2 ) INFORMATION FOR SEQ ID NO:29:

( i ) SEQUENCE CHARACTERISTICS:
        ( A ) LENGTH: 150 amino acids
        ( B ) TYPE: amino acid
        ( C ) STRANDEDNESS: single (D) TOPOLOGY: linear (ix) FEATURE:
    (A) NAME/KEY:
    (B) LOCATION:
    (C) IDENTIFICATION METHOD:
    (D) OTHER INFORMATION:

(xi) SEQUENCE DESCRIPTION: SEQ ID NO:29:

```
Pro Ser Asp Lys Pro Val Ala His Val Val Ala Asn Pro Gln Ala
 1           5                  10                  15

Glu Gly Gln Leu Gln Trp Leu Asn Arg Arg Ala Asn Ala Leu Leu
            20                  25                  30

Ala Asn Gly Val Glu Leu Arg Asp Asn Gln Leu Val Val Pro Ser
            35                  40                  45

Glu Asp Leu Tyr Leu Ile Tyr Ser Gln Val Leu Phe Lys Gly Gln
            50                  55                  60

Gly Cys Pro Ser Thr His Val Leu Leu Thr His Thr Ile Ser Arg
            65                  70                  75

Ile Ala Val Ser Tyr Gln Thr Lys Val Asn Leu Leu Ser Ala Ile
            80                  85                  90

Lys Ser Pro Cys Gln Arg Glu Thr Pro Glu Gly Ala Glu Ala Lys
            95                 100                 105

Pro Trp Tyr Glu Pro Ile Tyr Leu Gly Gly Val Phe Gln Leu Glu
           110                 115                 120

Lys Gly Asp Arg Leu Ser Ala Glu Ile Asn Arg Pro Asp Tyr Leu
           125                 130                 135

Asp Phe Ala Glu Ser Gly Gln Val Tyr Phe Gly Ile Ile Ala Leu
           140                 145                 150
```

(2) INFORMATION FOR SEQ ID NO:30:

(i) SEQUENCE CHARACTERISTICS:
        (A) LENGTH: 151 amino acids
        (B) TYPE: amino acid
        (C) STRANDEDNESS: single
        (D) TOPOLOGY: linear (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO:30:

```
Met Pro Ser Asp Lys Pro Val Ala His Val Val Ala Asn Pro Gln
 1           5                  10                  15

Ala Glu Gly Gln Leu Gln Trp Leu Asn Arg Arg Ala Asn Ala Leu
            20                  25                  30

Leu Ala Asn Gly Val Glu Leu Arg Asp Asn Gln Leu Val Val Pro
            35                  40                  45

Ser Glu Asp Leu Tyr Leu Ile Tyr Ser Gln Val Leu Phe Lys Gly
            50                  55                  60

Gln Gly Cys Pro Ser Thr His Val Leu Leu Thr His Thr Ile Ser
            65                  70                  75

Arg Ile Ala Val Ser Tyr Gln Thr Lys Val Asn Leu Leu Ser Ala
            80                  85                  90

Ile Lys Ser Pro Cys Gln Arg Glu Thr Pro Glu Gly Ala Glu Ala
            95                 100                 105

Lys Pro Trp Tyr Glu Pro Ile Tyr Leu Gly Gly Val Phe Gln Leu
           110                 115                 120

Glu Lys Gly Asp Arg Leu Ser Ala Glu Ile Asn Arg Pro Asp Tyr
```

5,262,309

-continued

```
                              125                     130                         135
Leu Asp Phe Ala Glu Ser Gly Gln Val Tyr Phe Gly Ile Ile Ala
                                  140                 145                         150

Leu
```

(2) INFORMATION FOR SEQ ID NO:31:

(i) SEQUENCE CHARACTERISTICS:
        (A) LENGTH: 150 amino acids
        (B) TYPE: amino acid
        (C) STRANDEDNESS: single
        (D) TOPOLOGY: linear (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO:31:

```
Pro Ser Asp Lys Pro Val Ala His Val Val Ala Asn Pro Gln Ala
1               5                   10                      15

Glu Gly Gln Leu Gln Trp Leu Asn Arg Arg Ala Asn Ala Leu Leu
                20                  25                      30

Ala Asn Gly Val Glu Leu Arg Asp Asn Gln Leu Val Val Pro Ser
                35                  40                      45

Glu Asp Leu Tyr Leu Ile Tyr Ser Gln Val Leu Phe Lys Gly Gln
                50                  55                      60

Gly Cys Pro Ser Thr His Val Leu Leu Thr His Thr Ile Ser Arg
                65                  70                      75

Ile Ala Val Ser Tyr Gln Thr Lys Val Asn Leu Leu Ser Ala Ile
                80                  85                      90

Lys Ser Pro Cys Gln Arg Glu Thr Pro Glu Gly Ala Glu Ala Lys
                95                  100                     105

Pro Trp Tyr Glu Pro Ile Tyr Leu Gly Gly Val Phe Gln Leu Glu
                110                 115                     120

Lys Gly Asp Arg Leu Ser Ala Glu Ile Asn Arg Pro Asp Tyr Leu
                125                 130                     135

Asp Phe Ala Glu Ser Gly Gln Val Tyr Phe Gly Ile Ile Ala Phe
                140                 145                     150
```

(2) INFORMATION FOR SEQ ID NO:32:

(i) SEQUENCE CHARACTERISTICS:
        (A) LENGTH: 151 amino acids
        (B) TYPE: amino acid
        (C) STRANDEDNESS: single
        (D) TOPOLOGY: linear (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO:32:

```
Met Pro Ser Asp Lys Pro Val Ala His Val Val Ala Asn Pro Gln
1               5                   10                      15

Ala Glu Gly Gln Leu Gln Trp Leu Asn Arg Arg Ala Asn Ala Leu
                20                  25                      30

Leu Ala Asn Gly Val Glu Leu Arg Asp Asn Gln Leu Val Val Pro
                35                  40                      45

Ser Glu Asp Leu Tyr Leu Ile Tyr Ser Gln Val Leu Phe Lys Gly
                50                  55                      60
```

```
Gln  Gly  Cys  Pro  Ser  Thr  His  Val  Leu  Leu  Thr  His  Thr  Ile  Ser
                65                  70                       75

Arg  Ile  Ala  Val  Ser  Tyr  Gln  Thr  Lys  Val  Asn  Leu  Leu  Ser  Ala
                80                       85                            90

Ile  Lys  Ser  Pro  Cys  Gln  Arg  Glu  Thr  Pro  Glu  Gly  Ala  Glu  Ala
                95                      100                           105

Lys  Pro  Trp  Tyr  Glu  Pro  Ile  Tyr  Leu  Gly  Gly  Val  Phe  Gln  Leu
               110                      115                           120

Glu  Lys  Gly  Asp  Arg  Leu  Ser  Ala  Glu  Ile  Asn  Arg  Pro  Asp  Tyr
               125                      130                           135

Leu  Asp  Phe  Ala  Glu  Ser  Gly  Gln  Val  Tyr  Phe  Gly  Ile  Ile  Ala
                140                     145                           150

Phe
```

(2) INFORMATION FOR SEQ ID NO:33:

(i) SEQUENCE CHARACTERISTICS:
        (A) LENGTH: 157 amino acids
        (B) TYPE: amino acid
        (C) STRANDEDNESS: single
        (D) TOPOLOGY: linear (ix) FEATURE:
        (A) NAME/KEY:
        (B) LOCATION:
        (C) IDENTIFICATION METHOD:
        (D) OTHER INFORMATION:

(xi) SEQUENCE DESCRIPTION: SEQ ID NO:33:

```
Val  Arg  Ser  Ser  Ser  Arg  Thr  Pro  Ser  Asp  Lys  Pro  Val  Ala  His
 1               5                      10                            15

Val  Val  Ala  Asn  Pro  Gln  Ala  Glu  Gly  Gln  Leu  Gln  Trp  Leu  Asn
                 20                      25                           30

Arg  Arg  Ala  Asn  Ala  Leu  Leu  Ala  Asn  Gly  Val  Glu  Leu  Arg  Asn
                 35                      40                           45

Asn  Ser  Leu  Val  Val  Pro  Ser  Glu  Gly  Leu  Tyr  Leu  Ile  Tyr  Ser
                 50                      55                           60

Gln  Val  Leu  Phe  Lys  Gly  Gln  Gly  Cys  Pro  Ser  Thr  His  Val  Leu
                  65                      70                           75

Leu  Thr  His  Thr  Ile  Ser  Arg  Ile  Ala  Val  Ser  Tyr  Gln  Thr  Lys
                 80                      85                           90

Val  Asn  Leu  Leu  Ser  Ala  Ile  Lys  Ser  Pro  Cys  Gln  Arg  Glu  Thr
                 95                     100                          105

Pro  Glu  Gly  Ala  Glu  Ala  Lys  Pro  Trp  Tyr  Glu  Pro  Ile  Tyr  Leu
                110                     115                          120

Gly  Gly  Val  Phe  Gln  Leu  Glu  Lys  Gly  Asp  Arg  Leu  Ser  Ala  Glu
                125                     130                          135

Ile  Asn  Arg  Pro  Asp  Tyr  Leu  Asp  Phe  Ala  Glu  Ser  Gly  Gln  Val
                140                     145                          150

Tyr  Phe  Gly  Ile  Ile  Ala  Leu
                155
```

(2) INFORMATION FOR SEQ ID NO:34:

(i) SEQUENCE CHARACTERISTICS:
        (A) LENGTH: 158 amino acids
        (B) TYPE: amino acid
        (C) STRANDEDNESS: single
        (D) TOPOLOGY: linear (ix) FEATURE:
        (A) NAME/KEY:

( B ) LOCATION:
( C ) IDENTIFICATION METHOD:
( D ) OTHER INFORMATION:

( x i ) SEQUENCE DESCRIPTION: SEQ ID NO:34:

| Met | Val | Arg | Ser | Ser | Ser | Arg | Thr | Pro | Ser | Asp | Lys | Pro | Val | Ala |
|---|---|---|---|---|---|---|---|---|---|---|---|---|---|---|
| 1 | | | | 5 | | | | | 10 | | | | | 15 |

| His | Val | Val | Ala | Asn | Pro | Gln | Ala | Glu | Gly | Gln | Leu | Gln | Trp | Leu |
|---|---|---|---|---|---|---|---|---|---|---|---|---|---|---|
| | | | | 20 | | | | | 25 | | | | | 30 |

| Asn | Arg | Arg | Ala | Asn | Ala | Leu | Leu | Ala | Asn | Gly | Val | Glu | Leu | Arg |
|---|---|---|---|---|---|---|---|---|---|---|---|---|---|---|
| | | | | 35 | | | | | 40 | | | | | 45 |

| Asn | Asn | Ser | Leu | Val | Val | Pro | Ser | Glu | Gly | Leu | Tyr | Leu | Ile | Tyr |
|---|---|---|---|---|---|---|---|---|---|---|---|---|---|---|
| | | | | 50 | | | | | 55 | | | | | 60 |

| Ser | Gln | Val | Leu | Phe | Lys | Gly | Gln | Gly | Cys | Pro | Ser | Thr | His | Val |
|---|---|---|---|---|---|---|---|---|---|---|---|---|---|---|
| | | | | 65 | | | | | 70 | | | | | 75 |

| Leu | Leu | Thr | His | Thr | Ile | Ser | Arg | Ile | Ala | Val | Ser | Tyr | Gln | Thr |
|---|---|---|---|---|---|---|---|---|---|---|---|---|---|---|
| | | | | 80 | | | | | 85 | | | | | 90 |

| Lys | Val | Asn | Leu | Leu | Ser | Ala | Ile | Lys | Ser | Pro | Cys | Gln | Arg | Glu |
|---|---|---|---|---|---|---|---|---|---|---|---|---|---|---|
| | | | | 95 | | | | | 100 | | | | | 105 |

| Thr | Pro | Glu | Gly | Ala | Glu | Ala | Lys | Pro | Trp | Tyr | Glu | Pro | Ile | Tyr |
|---|---|---|---|---|---|---|---|---|---|---|---|---|---|---|
| | | | | 110 | | | | | 115 | | | | | 120 |

| Leu | Gly | Gly | Val | Phe | Gln | Leu | Glu | Lys | Gly | Asp | Arg | Leu | Ser | Ala |
|---|---|---|---|---|---|---|---|---|---|---|---|---|---|---|
| | | | | 125 | | | | | 130 | | | | | 135 |

| Glu | Ile | Asn | Arg | Pro | Asp | Tyr | Leu | Asp | Phe | Ala | Glu | Ser | Gly | Gln |
|---|---|---|---|---|---|---|---|---|---|---|---|---|---|---|
| | | | | 140 | | | | | 145 | | | | | 150 |

| Val | Tyr | Phe | Gly | Ile | Ile | Ala | Leu |
|---|---|---|---|---|---|---|---|
| | | | | 155 | | | |

( 2 ) INFORMATION FOR SEQ ID NO:35:

( i ) SEQUENCE CHARACTERISTICS:
( A ) LENGTH: 150 amino acids
( B ) TYPE: amino acid
( C ) STRANDEDNESS: single
( D ) TOPOLOGY: linear ( i x ) FEATURE:
( A ) NAME/KEY:
( B ) LOCATION:
( C ) IDENTIFICATION METHOD:
( D ) OTHER INFORMATION:

( x i ) SEQUENCE DESCRIPTION: SEQ ID NO:35:

| Pro | Ser | Asp | Lys | Pro | Val | Ala | His | Val | Val | Ala | Asn | Pro | Gln | Ala |
|---|---|---|---|---|---|---|---|---|---|---|---|---|---|---|
| 1 | | | | 5 | | | | | 10 | | | | | 15 |

| Glu | Gly | Gln | Leu | Gln | Trp | Leu | Asn | Arg | Arg | Ala | Asn | Ala | Leu | Leu |
|---|---|---|---|---|---|---|---|---|---|---|---|---|---|---|
| | | | | 20 | | | | | 25 | | | | | 30 |

| Ala | Asn | Gly | Val | Glu | Leu | Arg | Asn | Asn | Ser | Leu | Val | Val | Pro | Ser |
|---|---|---|---|---|---|---|---|---|---|---|---|---|---|---|
| | | | | 35 | | | | | 40 | | | | | 45 |

| Glu | Gly | Leu | Tyr | Leu | Ile | Tyr | Ser | Gln | Val | Leu | Phe | Lys | Gly | Gln |
|---|---|---|---|---|---|---|---|---|---|---|---|---|---|---|
| | | | | 50 | | | | | 55 | | | | | 60 |

| Gly | Cys | Pro | Ser | Thr | His | Val | Leu | Leu | Thr | His | Thr | Ile | Ser | Arg |
|---|---|---|---|---|---|---|---|---|---|---|---|---|---|---|
| | | | | 65 | | | | | 70 | | | | | 75 |

| Ile | Ala | Val | Ser | Tyr | Gln | Thr | Lys | Val | Asn | Leu | Leu | Ser | Ala | Ile |
|---|---|---|---|---|---|---|---|---|---|---|---|---|---|---|
| | | | | 80 | | | | | 85 | | | | | 90 |

| Lys | Ser | Pro | Cys | Gln | Arg | Glu | Thr | Pro | Glu | Gly | Ala | Glu | Ala | Lys |
|---|---|---|---|---|---|---|---|---|---|---|---|---|---|---|
| | | | | 95 | | | | | 100 | | | | | 105 |

| Pro | Trp | Tyr | Glu | Pro | Ile | Tyr | Leu | Gly | Gly | Val | Phe | Gln | Leu | Glu |
|---|---|---|---|---|---|---|---|---|---|---|---|---|---|---|
| | | | | 110 | | | | | 115 | | | | | 120 |

| Lys | Gly | Asp | Arg | Leu | Ser | Ala | Glu | Ile | Asn | Arg | Pro | Asp | Tyr | Leu |
|---|---|---|---|---|---|---|---|---|---|---|---|---|---|---|
| | | | | 125 | | | | | 130 | | | | | 135 |

```
Asp Phe Ala Glu Ser Gly Gln Val Tyr Phe Gly Ile Ile Ala Leu
            140                 145                 150
```

( 2 ) INFORMATION FOR SEQ ID NO:36:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:36:

```
Met Pro Ser Asp Lys Pro Val Ala His Val Val Ala Asn Pro Gln
 1               5                  10                  15

Ala Glu Gly Gln Leu Gln Trp Leu Asn Arg Arg Ala Asn Ala Leu
                20                  25                  30

Leu Ala Asn Gly Val Glu Leu Arg Asn Asn Ser Leu Val Val Pro
                35                  40                  45

Ser Glu Gly Leu Tyr Leu Ile Tyr Ser Gln Val Leu Phe Lys Gly
                50                  55                  60

Gln Gly Cys Pro Ser Thr His Val Leu Leu Thr His Thr Ile Ser
                65                  70                  75

Arg Ile Ala Val Ser Tyr Gln Thr Lys Val Asn Leu Leu Ser Ala
                80                  85                  90

Ile Lys Ser Pro Cys Gln Arg Glu Thr Pro Glu Gly Ala Glu Ala
                95                  100                 105

Lys Pro Trp Tyr Glu Pro Ile Tyr Leu Gly Gly Val Phe Gln Leu
                110                 115                 120

Glu Lys Gly Asp Arg Leu Ser Ala Glu Ile Asn Arg Pro Asp Tyr
                125                 130                 135

Leu Asp Phe Ala Glu Ser Gly Gln Val Tyr Phe Gly Ile Ile Ala
                 140                 145                 150

Leu
```

( 2 ) INFORMATION FOR SEQ ID NO:37:

( i ) SEQUENCE CHARACTERISTICS:
        ( A ) LENGTH: 150 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:37:

```
Pro Ser Asp Lys Pro Val Ala His Val Val Ala Asn Pro Gln Ala
 1               5                  10                  15

Glu Gly Gln Leu Gln Trp Leu Asn Arg Arg Ala Asn Ala Leu Leu
                20                  25                  30

Ala Asn Gly Val Glu Leu Arg Asn Asn Ser Leu Val Val Pro Ser
                35                  40                  45

Glu Gly Leu Tyr Leu Ile Tyr Ser Gln Val Leu Phe Lys Gly Gln
                50                  55                  60
```

```
Gly Cys Pro Ser Thr His Val Leu Leu Thr His Thr Ile Ser Arg
             65                  70                  75

Ile Ala Val Ser Tyr Gln Thr Lys Val Asn Leu Leu Ser Ala Ile
             80                  85                  90

Lys Ser Pro Cys Gln Arg Glu Thr Pro Glu Gly Ala Glu Ala Lys
             95                 100                 105

Pro Trp Tyr Glu Pro Ile Tyr Leu Gly Gly Val Phe Gln Leu Glu
            110                 115                 120

Lys Gly Asp Arg Leu Ser Ala Glu Ile Asn Arg Pro Asp Tyr Leu
            125                 130                 135

Asp Phe Ala Glu Ser Gly Gln Val Tyr Phe Gly Ile Ile Ala Phe
            140                 145                 150
```

( 2 ) INFORMATION FOR SEQ ID NO:38:

( i ) SEQUENCE CHARACTERISTICS:
        ( A ) LENGTH: 151 amino acids
        ( B ) TYPE: amino acid
        ( C ) STRANDEDNESS: single
        ( D ) TOPOLOGY: linear ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:38:

```
Met Pro Ser Asp Lys Pro Val Ala His Val Val Ala Asn Pro Gln
 1               5                  10                  15

Ala Glu Gly Gln Leu Gln Trp Leu Asn Arg Arg Ala Asn Ala Leu
             20                  25                  30

Leu Ala Asn Gly Val Glu Leu Arg Asn Asn Ser Leu Val Val Pro
             35                  40                  45

Ser Glu Gly Leu Tyr Leu Ile Tyr Ser Gln Val Leu Phe Lys Gly
             50                  55                  60

Gln Gly Cys Pro Ser Thr His Val Leu Leu Thr His Thr Ile Ser
             65                  70                  75

Arg Ile Ala Val Ser Tyr Gln Thr Lys Val Asn Leu Leu Ser Ala
             80                  85                  90

Ile Lys Ser Pro Cys Gln Arg Glu Thr Pro Glu Gly Ala Glu Ala
             95                 100                 105

Lys Pro Trp Tyr Glu Pro Ile Tyr Leu Gly Gly Val Phe Gln Leu
            110                 115                 120

Glu Lys Gly Asp Arg Leu Ser Ala Glu Ile Asn Arg Pro Asp Tyr
            125                 130                 135

Leu Asp Phe Ala Glu Ser Gly Gln Val Tyr Phe Gly Ile Ile Ala
            140                 145                 150

Phe
```

( 2 ) INFORMATION FOR SEQ ID NO:39:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: circular ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:39:

ATTATTGCCT TC                    12

( 2 ) INFORMATION FOR SEQ ID NO:40:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: circular ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:40:

ATTATTGCCT GG                    12

( 2 ) INFORMATION FOR SEQ ID NO:41:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: circular ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:41:

ATTATTGCCC TGTTC                    15

( 2 ) INFORMATION FOR SEQ ID NO:42:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: circular ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:42:

ATTATTTGGC TG                    12

( 2 ) INFORMATION FOR SEQ ID NO:43:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: circular ( i x ) FEATURE:
        ( A ) NAME/KEY:
        ( B ) LOCATION:
        ( C ) IDENTIFICATION METHOD:
        ( D ) OTHER INFORMATION:

( x i ) SEQUENCE DESCRIPTION: SEQ ID NO:43:

ATTATTTTCC TG                    12

( 2 ) INFORMATION FOR SEQ ID NO:44:

( i ) SEQUENCE CHARACTERISTICS:
( A ) LENGTH: 12 base pairs
( B ) TYPE: nucleic acid
( C ) STRANDEDNESS: double
( D ) TOPOLOGY: circular ( i x ) FEATURE:
( A ) NAME/KEY:
( B ) LOCATION:
( C ) IDENTIFICATION METHOD:
( D ) OTHER INFORMATION:

( x i ) SEQUENCE DESCRIPTION: SEQ ID NO:44:

ATTATTTTCT TC                    12

( 2 ) INFORMATION FOR SEQ ID NO:45:

( i ) SEQUENCE CHARACTERISTICS:
( A ) LENGTH: 12 base pairs
( B ) TYPE: nucleic acid
( C ) STRANDEDNESS: double
( D ) TOPOLOGY: circular ( i x ) FEATURE:
( A ) NAME/KEY:
( B ) LOCATION:
( C ) IDENTIFICATION METHOD:
( D ) OTHER INFORMATION:

( x i ) SEQUENCE DESCRIPTION: SEQ ID NO:45:

ATTATTTGGT TC                    12

( 2 ) INFORMATION FOR SEQ ID NO:46:

( i ) SEQUENCE CHARACTERISTICS:
( A ) LENGTH: 12 base pairs
( B ) TYPE: nucleic acid
( C ) STRANDEDNESS: double
( D ) TOPOLOGY: circular ( i x ) FEATURE:
( A ) NAME/KEY:
( B ) LOCATION:
( C ) IDENTIFICATION METHOD:
( D ) OTHER INFORMATION:

( x i ) SEQUENCE DESCRIPTION: SEQ ID NO:46:

ATTTTCGCCC TG                    12

( 2 ) INFORMATION FOR SEQ ID NO:47:

( i ) SEQUENCE CHARACTERISTICS:
( A ) LENGTH: 12 base pairs
( B ) TYPE: nucleic acid
( C ) STRANDEDNESS: double
( D ) TOPOLOGY: circular ( i x ) FEATURE:
( A ) NAME/KEY:
( B ) LOCATION:
( C ) IDENTIFICATION METHOD:
( D ) OTHER INFORMATION:

( x i ) SEQUENCE DESCRIPTION: SEQ ID NO:47:

TTCATTGCCC TG                    12

( 2 ) INFORMATION FOR SEQ ID NO:48:

( i ) SEQUENCE CHARACTERISTICS:
( A ) LENGTH: 429 base pairs
( B ) TYPE: nucleic acid
( C ) STRANDEDNESS: double
( D ) TOPOLOGY: circular ( i x ) FEATURE:
  ( A ) NAME/KEY:
  ( B ) LOCATION:
  ( C ) IDENTIFICATION METHOD:
  ( D ) OTHER INFORMATION:

( x i ) SEQUENCE DESCRIPTION: SEQ ID NO:48:

```
AAGCCTGTAG CCCATGTTGT AGCAAACCCT CAAGCTGAGG GGCAGCTCCA      50
GTGGCTGAAC CGCCGGGCCA ATGCCCTGCT GGCCAATGGC GTGGAGCTGA     100
GAGATAACCA GCTGGTGGTA CCATCAGAGG GCCTGTACCT CATCTACTCC     150
CAGGTCCTCT TCAAGGGCCA AGGCTGCCCG TCGACCCATG TGCTCCTCAC     200
CCACACCATC AGCCGCATCG CCGTCTCCTA CCAGACCAAG GTCAACCTCC     250
TCTCTGCGAT CAAGAGCCCC TGCCAGAGGG AGACCCAGA  GGGGGCTGAG     300
GCCAAGCCAT GGTATGAGCC CATCTATCTG GGAGGGGTCT TCCAGCTGGA     350
GAAGGGTGAC CGACTCAGCG CTGAAATCAA TCGGCCCGAC TATCTCGACT     400
TTGCCGAGTC TGGGCAGGTC TACTTTGGG                            429
```

( 2 ) INFORMATION FOR SEQ ID NO:49:

( i ) SEQUENCE CHARACTERISTICS:
    ( A ) LENGTH: 103 base pairs
    ( B ) TYPE: nucleic acid
    ( C ) STRANDEDNESS: double
    ( D ) TOPOLOGY: circular ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO:49:

```
CATCATAACG GTTCTGGCAA ATATTCTGAA ATGAGCTGTT GACAATTAAT      50
CATCGAACTA GTTAACTAGT ACGCAAGTTC ACGTAAAAAG GGTATCGATA     100
ATG                                                        103
```

( 2 ) INFORMATION FOR SEQ ID NO:50:

( i ) SEQUENCE CHARACTERISTICS:
    ( A ) LENGTH: 38 base pairs
    ( B ) TYPE: nucleic acid
    ( C ) STRANDEDNESS: double
    ( D ) TOPOLOGY: circular ( i x ) FEATURE:
    ( A ) NAME/KEY:
    ( B ) LOCATION:
    ( C ) IDENTIFICATION METHOD:
    ( D ) OTHER INFORMATION:

( x i ) SEQUENCE DESCRIPTION: SEQ ID NO:50:

```
TGATAAGCTT AGCCCGCCTA ATGAGCGGGC TTTTTTT                    38
```